(12) United States Patent
Griffin et al.

(10) Patent No.: US 12,344,615 B2
(45) Date of Patent: *Jul. 1, 2025

(54) SUBSTITUTED PYRIDINES AS ION CHANNEL MODULATORS

(71) Applicant: PRAXIS PRECISION MEDICINES, INC., Boston, MA (US)

(72) Inventors: Andrew Mark Griffin, L'Ile Bizard (CA); Brian Edward Marron, Ada, MI (US); Gabriel Martinez Botella, Wayland, MA (US); Kiran Reddy, Boston, MA (US)

(73) Assignee: Praxis Precision Medicines, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/968,465

(22) Filed: Oct. 18, 2022

(65) Prior Publication Data

US 2023/0286984 A1 Sep. 14, 2023

Related U.S. Application Data

(63) Continuation of application No. 16/887,906, filed on May 29, 2020, now Pat. No. 11,505,554.

(60) Provisional application No. 62/855,298, filed on May 31, 2019.

(51) Int. Cl.
*C07D 213/64* (2006.01)
*C07D 487/04* (2006.01)

(52) U.S. Cl.
CPC .................. *C07D 487/04* (2013.01)

(58) Field of Classification Search
CPC .................................................. C07D 213/64
USPC ........................................................ 546/290
See application file for complete search history.

(56) References Cited

U.S. PATENT DOCUMENTS

| | | | |
|---|---|---|---|
| 3,845,770 A | 11/1974 | Theeuwes et al. |
| 4,112,095 A | 9/1978 | Allen, Jr. et al. |
| 4,230,705 A | 10/1980 | Allen, Jr. et al. |
| 4,242,515 A | 12/1980 | Trust et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,616,345 A | 4/1997 | Geoghegan et al. |
| 5,905,079 A | 5/1999 | Sargent et al. |
| 6,589,952 B2 | 7/2003 | Bakthavatchalam et al. |
| 7,863,279 B2 | 1/2011 | Even et al. |
| 8,030,305 B2 | 10/2011 | Lu et al. |
| 8,173,654 B2 | 5/2012 | Lu et al. |
| 8,198,448 B2 | 6/2012 | Albrecht et al. |
| 8,212,041 B2 | 7/2012 | Albrecht et al. |
| 8,217,177 B2 | 7/2012 | Albrecht et al. |
| 8,524,900 B2 | 9/2013 | Albrecht et al. |
| 8,937,060 B2 | 1/2015 | Cid-Nunez et al. |
| 8,952,034 B2 | 2/2015 | Corkey et al. |
| 9,066,954 B2 | 6/2015 | Albrecht et al. |
| 9,371,329 B2 | 6/2016 | Corkey et al. |
| 10,280,184 B2 | 5/2019 | Friedman et al. |
| 11,014,931 B2 | 5/2021 | Griffin et al. |
| 11,261,188 B2 | 3/2022 | Reddy et al. |
| 11,278,535 B2 | 3/2022 | Reddy et al. |
| 11,279,700 B2 | 3/2022 | Griffin et al. |
| 11,505,554 B2 | 11/2022 | Griffin et al. |
| 11,629,146 B2 | 4/2023 | Reddy et al. |
| 2002/0049208 A1 | 4/2002 | Bakthavatchalam et al. |
| 2009/0124609 A1 | 5/2009 | Albrecht et al. |
| 2009/0203707 A1 | 8/2009 | Rajamani et al. |
| 2010/0088778 A1 | 4/2010 | Mulley et al. |
| 2011/0021521 A1 | 1/2011 | Corkey et al. |
| 2012/0010192 A1 | 1/2012 | Kobayashi et al. |
| 2012/0065191 A1 | 3/2012 | Kiss et al. |
| 2012/0245164 A1 | 9/2012 | Auger et al. |
| 2013/0315895 A1 | 11/2013 | Farrell et al. |
| 2014/0066443 A1 | 3/2014 | Beshore et al. |

(Continued)

FOREIGN PATENT DOCUMENTS

| | | |
|---|---|---|
| CA | 1080712 A | 7/1980 |
| JP | S5340798 A | 4/1978 |

(Continued)

OTHER PUBLICATIONS

US 8,754,103 B2, 06/2014, Corkey et al. (withdrawn)

(Continued)

*Primary Examiner* — Douglas M Willis

(74) *Attorney, Agent, or Firm* — McCarter & English, LLP; Jonathan M. Sparks

(57) ABSTRACT

Provided, in part, are compounds of Formula I.

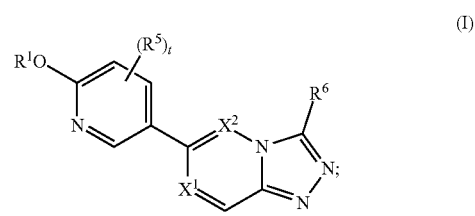

pharmaceutically acceptable salts thereof, and pharmaceutical compositions thereof, which are useful in the treatment of conditions associated with the activity of sodium channels. Methods of treating a disease or condition relating to aberrant function of a sodium ion channel including neurological disorders (e.g., Dravet syndrome, epilepsy), pain, and neuromuscular disorders are also provided herein.

12 Claims, No Drawings

(56) References Cited

U.S. PATENT DOCUMENTS

| | | |
|---|---|---|
| 2014/0303158 A1 | 10/2014 | Corkey et al. |
| 2015/0038503 A1 | 2/2015 | Bourotte et al. |
| 2015/0344457 A1 | 12/2015 | Duncan et al. |
| 2016/0159801 A1 | 6/2016 | Quinn et al. |
| 2016/0235718 A1 | 8/2016 | Baraban |
| 2016/0297799 A1 | 10/2016 | Brookings et al. |
| 2016/0317536 A1 | 11/2016 | Reich et al. |
| 2019/0308938 A1 | 10/2019 | McCormack et al. |
| 2019/0389868 A1 | 12/2019 | Reddy et al. |
| 2020/0179358 A1 | 6/2020 | Reddy et al. |
| 2020/0247793 A1 | 8/2020 | Reddy et al. |
| 2020/0377499 A1 | 12/2020 | Griffin et al. |
| 2020/0377506 A1 | 12/2020 | Reddy et al. |
| 2021/0087197 A1 | 3/2021 | Griffin et al. |
| 2021/0163488 A1 | 6/2021 | Griffin et al. |
| 2021/0171530 A1 | 6/2021 | Reddy et al. |
| 2021/0188839 A1 | 6/2021 | Reddy et al. |
| 2021/0355118 A1 | 11/2021 | Reddy et al. |
| 2021/0403476 A1 | 12/2021 | Reddy et al. |
| 2022/0024930 A1 | 1/2022 | Griffin et al. |

FOREIGN PATENT DOCUMENTS

| | | |
|---|---|---|
| JP | 2017-1991 A | 1/2017 |
| WO | WO-2006/061428 A2 | 6/2006 |
| WO | WO-2007/075567 A1 | 7/2007 |
| WO | WO-2008/008539 A2 | 1/2008 |
| WO | WO-2010/053757 A1 | 5/2010 |
| WO | WO-2010/056865 A1 | 5/2010 |
| WO | WO-2010/074807 A1 | 7/2010 |
| WO | WO-2011/014462 A1 | 2/2011 |
| WO | WO-2011/056985 A2 | 5/2011 |
| WO | WO-2012/003392 A1 | 1/2012 |
| WO | WO-2012/065546 A1 | 5/2012 |
| WO | WO-2012/154760 A1 | 11/2012 |
| WO | WO-2013/006463 A1 | 1/2013 |
| WO | WO-2013/043925 A1 | 3/2013 |
| WO | WO-2014/179492 A1 | 11/2014 |
| WO | WO-2015/095370 A1 | 6/2015 |
| WO | WO-2015/158283 A1 | 10/2015 |
| WO | WO-2015/194670 A1 | 12/2015 |
| WO | WO-2015/197567 A1 | 12/2015 |
| WO | WO-2018/067786 A1 | 4/2018 |
| WO | WO-2018/098491 A1 | 5/2018 |
| WO | WO-2018/098499 A1 | 5/2018 |
| WO | WO-2018/098500 A1 | 5/2018 |
| WO | WO-2018/148745 A1 | 8/2018 |
| WO | WO-2018/187480 A1 | 10/2018 |
| WO | WO-2019/035951 A1 | 2/2019 |
| WO | WO-2019/232209 A1 | 12/2019 |
| WO | WO-2020/069322 A1 | 4/2020 |
| WO | WO-2021/108513 A1 | 6/2021 |
| WO | WO-2021/108625 A1 | 6/2021 |

OTHER PUBLICATIONS

Albright et al., Synthesis and anxiolytic activity of 6-(substituted-phenyl)-1,2,4-triazolo[4,3-b]pyridazines. J Med Chem. May 1981;24(5):592-600.

Anderson et al., Antiepileptic activity of preferential inhibitors of persistent sodium current. Epilepsia. Aug. 2014;55(8):1274-83.

Anderson et al., Unexpected Efficacy of a Novel Sodium Channel Modulator in Dravet Syndrome. Sci Rep. May 10, 2017;7(1):1682, 9 pages.

Baker et al., The novel sodium channel modulator GS-458967 (GS967) is an effective treatment in a mouse model of SCN8A encephalopathy. Epilepsia. Jun. 2018;59(6):1166-1176.

Barbieri et al., Late sodium current blocker GS967 inhibits persistent currents induced by familial hemiplegic migraine type 3 mutations of the SCN1A gene. J Headache Pain. Nov. 15, 2019;20(1):107, 13 pages.

Belardinelli et al., A novel, potent, and selective inhibitor of cardiac late sodium current suppresses experimental arrhythmias. J Pharmacol Exp Ther. Jan. 2013;344(1):23-32.

Berge et al., Pharmaceutical salts. J Pharm Sci. Jan. 1977;66(1):1-19.

Burbano et al., Characterization of a Novel Knock-in Mouse Model of KCNT1 Epileptic Encephalopathy. Neurology. Apr. 10, 2018;90(Suppl 15). Abstract P2.273.

Cannon, Analog Design. Burger's Medicinal Chemistry and Drug Discovery, Fifth Edition, vol. I: Principles and Practice. Manfred E. Wolff (Ed.). John Wiley & Sons, Inc., New York. Chapter 19, pp. 783-802, (1995).

Chaplan et al., Quantitative assessment of tactile allodynia in the rat paw. J Neurosci Methods. Jul. 1994;53(1):55-63.

Dorwald, Side Reactions in Organic Synthesis, a Guide to Successful Synthesis Design. Wiley-VCH Verlag GmbH & Co. KGaA. 37 pages, (2005).

Flynn et al., Correlation and prediction of mass transport across membranes. I. Influence of alkyl chain length on flux-determining properties of barrier and diffusant. J Pharm Sci. Jun. 1972;61(6):838-52.

Fukaya et al., Identification of a novel benzoxazolone derivative as a selective, orally active 18 kDa translocator protein (TSPO) ligand. J Med Chem. Oct. 24, 2013;56(20):8191-5.

Guan et al., Synthesis and anticonvulsant activity of a new 6-alkoxy-[1,2,4]triazolo[4,3-b]pyridazine. Eur J Med Chem. May 2010;45(5):1746-52.

Hackam et al., Translation of research evidence from animals to humans. JAMA. Oct. 11, 2006;296(14):1731-2.

Jordan, Tamoxifen: a most unlikely pioneering medicine. Nat Rev Drug Discov. Mar. 2003;2(3):205-13.

Kearney et al., A gain-of-function mutation in the sodium channel gene Scn2a results in seizures and behavioral abnormalities. Neuroscience. Feb. 2001;102(2):307-17.

Kim et al., An experimental model for peripheral neuropathy produced by segmental spinal nerve ligation in the rat. Pain. Sep. 1992;50(3):355-363.

Koltun et al., Discovery of triazolopyridinone GS-462808, a late sodium current inhibitor (Late INai) of the cardiac Nav1.5 channel with improved efficacy and potency relative to ranolazine. Bioorg Med Chem Lett. Jul. 1, 2016;26(13):3207-3211.

Li et al., Antisense oligonucleotide therapy for SCN2A gain-of-function epilepsies. AES, American Epilepsy Society. 28 pages, (2018).

Patel et al., Neuropathy following spinal nerve injury shares features with the irritable nociceptor phenotype: A back-translational study of oxcarbazepine. Eur J Pain. Jan. 2019;23(1):183-197.

Petrou et al., Antisense oligonucleotide therapy for SCN2A gain-of-function epilepsies. AES, American Epilepsy Society. Retrieved online at: https://www.aesnet.org/abstractslisting/antisense-oligonucleotide-therapy-for-scn2a-gain-of-function-epilepsies. Abstract 1.466, 2 pages, (2018).

PubChem CID 58763997, 5-Phenylpyrazolo[1,5-A]pyridine. 14 pages, Mar. 10, 2018.

PubChem CID 597467, 5-Phenyl-2H-benzotriazole, 15 pages, May 12, 2018.

PubChem CID 82381512, Tuijeduithxzgl-Uhfffaoysa-N, 10 pages, Sep. 29, 2018.

PubChem CID 89077556, SCHEMBL13387345, 11 pages, Jan. 6, 2018.

STN Chemical Structure Search Results, 102 pages, May 18, 2016.
STN Chemical Structure Search Results, 107 pages, Nov. 1, 2017.
STN Chemical Structure Search Results, 123 pages, Nov. 6, 2017.
STN Chemical Structure Search Results, 22 pages, Jan. 15, 2020.
STN Chemical Structure Search Results, 23 pages, Jan. 2018.
STN Chemical Structure Search Results, 264 pages, Mar. 20, 2018.
STN Chemical Structure Search Results, 29 pages, Feb. 2018.
STN Chemical Structure Search Results, 36 pages, Apr. 14, 2019.
STN Chemical Structure Search Results, 45 pages, Apr. 23, 2019.
STN Chemical Structure Search Results, 480 pages, Mar. 6, 2017.
STN Chemical Structure Search Results, 511 pages, Mar. 6, 2017.
STN Chemical Structure Search Results, 55 pages, Apr. 2018.
STN Chemical Structure Search Results, 57 pages, Nov. 3, 2017.
STN Chemical Structure Search Results, 7 pages, Nov. 6, 2017.

(56) References Cited

OTHER PUBLICATIONS

STN Chemical Structure Search Results, 83 pages, Mar. 20, 2018.
STN Chemical Structure Search Results, 85 pages, Nov. 21, 2017.
STN RN 1347643-11-1, 1,2,4-Triazolo(4,3-b)pyridazine, 7-methyl-6-(4-[3-(3-piperidinyl)propoxy]phenyl). 1 page, dated Dec. 2, 2011.
Venkatesh et al., Role of the development scientist in compound lead selection and optimization. J Pharm Sci. Feb. 2000;89(2):145-54.
Wagnon et al., Convulsive seizures and SUDEP in a mouse model of SCN8A epileptic encephalopathy. Hum Mol Genet. Jan. 15, 2015;24(2):506-15.
Wengert et al., Prax330 reduces persistent and resurgent sodium channel currents and neuronal hyperexcitability of subiculum neurons in a mouse model of SCN8A epileptic encephalopathy. Neuropharmacology. Nov. 1, 2019;158:107699, 26 pages.
Wilen et al., Strategies in optical resolutions. Tetrahedron. 1977;33(21):2725-2736.
Woodland et al., Discovery of Inhibitors of Trypanosoma brucei by Phenotypic Screening of a Focused Protein Kinase Library. ChemMedChem. Nov. 2015; 10(11):1809-20.
Zablocki et al., Discovery of Dihydrobenzoxazepinone (GS-6615) Late Sodium Current Inhibitor (Late INai), a Phase II Agent with Demonstrated Preclinical Anti-Ischemic and Antiarrhythmic Properties. J Med Chem. Oct. 13, 2016;59(19):9005-9017.
Zaza et al., Pathophysiology and pharmacology of the cardiac "late sodium current.". Pharmacol Ther. Sep. 2008;119(3):326-39.
International Preliminary Report on Patentability for Application No. PCT/US2017/063507, dated Jun. 6, 2019, 7 pages.
International Preliminary Report on Patentability for Application No. PCT/US2017/063534, dated Jun. 6, 2019, 9 pages.
International Preliminary Report on Patentability for Application No. PCT/US2018/000224, dated Feb. 27, 2020, 7 pages.
International Preliminary Report on Patentability for Application No. PCT/US2018/018044, dated Aug. 22, 2019, 8 pages.
International Preliminary Report on Patentability for Application No. PCT/US2018/026099, dated Oct. 17, 2019, 7 pages.
International Preliminary Report on Patentability for Application No. PCT/US2020/062179, dated Jun. 9, 2022, 6 pages.
International Search Report and Written Opinion for Application No. PCT/US2017/063507, dated Mar. 29, 2019, 9 pages.
International Search Report and Written Opinion for Application No. PCT/US2017/063533, dated Mar. 29, 2019, 10 pages.
International Search Report and Written Opinion for Application No. PCT/US2017/063534, dated Mar. 29, 2019, 11 pages.
International Search Report and Written Opinion for Application No. PCT/US2018/000224, dated Nov. 5, 2018, 8 pages.
International Search Report and Written Opinion for Application No. PCT/US2018/018044, dated May 24, 2018, 10 pages.
International Search Report and Written Opinion for Application No. PCT/US2018/026099, dated Aug. 10, 2018, 9 pages.
International Search Report and Written Opinion for Application No. PCT/US2019/034653, dated Aug. 9, 2019, 9 pages.
International Search Report and Written Opinion for Application No. PCT/US2019/053467, dated Jan. 14, 2020, 9 pages.
International Search Report and Written Opinion for Application No. PCT/US2020/062179, dated Feb. 25, 2021, 7 pages.
International Search Report and Written Opinion for Application No. PCT/US2020/062317, dated Apr. 6, 2021, 14 pages.
U.S. Pat. No. 8,754,103 B2, 06/2014, Corkey et al. (withdrawn).
US Notice of Allowance for U.S. Appl. No. 16/464,483, dated Oct. 14, 2021, 9 pages.
US Notice of Allowance for U.S. Appl. No. 16/485,581, dated Dec. 15, 2021, 7 pages.
US Notice of Allowance for U.S. Appl. No. 16/485,581, dated Sep. 3, 2021, 7 pages.
US Notice of Allowance for U.S. Appl. No. 16/638,725, dated Jul. 26, 2021, 8 pages.
US Notice of Allowance for U.S. Appl. No. 16/638,725, dated Nov. 18, 2021, 8 pages.
US Notice of Allowance for U.S. Appl. No. 16/887,897, dated Jul. 23, 2021, 13 pages.
US Notice of Allowance for U.S. Appl. No. 16/887,897, dated Nov. 22, 2021, 8 pages.
US Notice of Allowance for U.S. Appl. No. 17/102,586, dated Mar. 8, 2021, 8 pages.
US Office Action for U.S. Appl. No. 16/464,483, dated Jun. 30, 2021, 22 pages.
US Office Action for U.S. Appl. No. 16/485,581, dated Mar. 10, 2021, 8 pages.
US Office Action for U.S. Appl. No. 16/500,795, dated Apr. 13, 2022, 18 pages.
US Office Action for U.S. Appl. No. 16/638,725, dated Apr. 2, 2021, 8 pages.
US Office Action for U.S. Appl. No. 16/638,725, dated Dec. 11, 2020, 16 pages.
US Office Action for U.S. Appl. No. 16/885,605, dated Jan. 28, 2022, 10 pages.
US Office Action for U.S. Appl. No. 17/102,586, dated Jan. 26, 2021, 14 pages.
US Restriction Requirement for U.S. Appl. No. 16/464,467, dated Nov. 4, 2021, 14 pages.
US Restriction Requirement for U.S. Appl. No. 16/464,468, dated Oct. 15, 2021, 11 pages.
US Restriction Requirement for U.S. Appl. No. 16/464,483, dated Oct. 9, 2020, 8 pages.
US Restriction Requirement for U.S. Appl. No. 16/485,581, dated Sep. 16, 2020, 5 pages.
US Restriction Requirement for U.S. Appl. No. 16/500,795, dated Dec. 16, 2021, 11 pages.
US Restriction Requirement for U.S. Appl. No. 16/638,725, dated Aug. 25, 2020, 8 pages.
US Restriction Requirement for U.S. Appl. No. 16/885,605, dated Sep. 21, 2021, 8 pages.
US Restriction Requirement for U.S. Appl. No. 16/887,897, dated Apr. 30, 2021, 9 pages.
U.S. Appl. No. 16/887,906, filed May 29, 2020, U.S. Pat. No. 11,505,554.

SUBSTITUTED PYRIDINES AS ION CHANNEL MODULATORS

CROSS REFERENCE TO RELATED APPLICATIONS

This application is a continuation of U.S. patent application Ser. No. 16/887,906, filed on May 29, 2020; which claims priority to and the benefit of U.S. Provisional Patent Application No. 62/855,298 filed on May 31, 2019. The entire contents of each of the foregoing applications are hereby incorporated herein by reference.

BACKGROUND

Sodium ion (Na+) channels primarily open in a transient manner and are quickly inactivated, thereby generating a fast Na+ current to initiate the action potential. The late or persistent sodium current (INaL) is a sustained component of the fast Na+ current of cardiac myocytes and neurons. Many common neurological and cardiac conditions are associated with abnormal INaL enhancement, which contributes to the pathogenesis of both electrical and contractile dysfunction in mammals (see, e.g., *Pharmacol Ther* (2008) 119:326-339). Accordingly, pharmaceutical compounds that selectively modulate sodium channel activity, e.g., abnormal INaL, are useful in treating such disease states.

SUMMARY

Described herein are fused heteroaryl compounds and compositions useful for preventing and/or treating a disease, disorder, or condition, e.g., a disease, disorder, or condition relating to aberrant function of a sodium ion channel, e.g., abnormal late sodium current (INaL).

In one aspect, the present disclosure features compounds of Formula I:

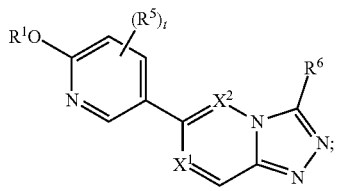

(I)

or a pharmaceutically acceptable salt thereof, wherein
  $X^1$ is N and $X^2$ is $CR^d$, or $X^1$ is $CR^d$ and $X^2$ is N;
  $R^1$ is selected from the group consisting of —$CR^2R^3R^4$, monocyclic $C_{3-6}$ cycloalkyl, and 4- to 7-membered monocyclic heterocyclyl, wherein said cycloalkyl and heterocyclyl are optionally substituted with one or more $R^a$;
  $R^2$ is $C_{1-4}$haloalkyl or monocyclic $C_{3-6}$ cycloalkyl optionally substituted with one or more $R^b$;
  $R^3$ is selected from the group consisting of hydrogen, $C_{1-4}$alkyl, and $C_{1-4}$haloalkyl;
  $R^4$ is selected from the group consisting of hydrogen, $C_{1-4}$alkyl, and $C_{1-4}$haloalkyl;
  $R^5$ is halo;
  $R^6$ is $C_1$-$C_4$haloalkyl or $C_{3-6}$ monocyclic cycloalkyl, wherein said cycloalkyl for $R^6$ is optionally substituted with one or more $R^c$;
  t is selected from the group consisting of 0, 1, and 2;
  $R^a$, $R^b$, and $R^c$ are each independently selected from the group consisting of halo, $C_{1-4}$alkyl, $C_{1-4}$haloalkyl, $C_{1-4}$alkoxy, and $C_{1-4}$haloalkoxy; and
  $R^d$ is selected from the group consisting of hydrogen, halo, and $C_{1-4}$ alkyl;
  provided that:
    when $R^3$ and $R^4$ are each hydrogen, then $R^6$ is not difluorocyclobutyl, fluorocyclopropyl, difluorocyclopropyl, cyclopropyl, or $CF_2Cl$;
    when $R^6$ is $CF_3$ or $CHF_2$, then $R^1$ is not difluorocyclobutyl;
    when $R^6$ is $CF_3$ or $CHF_2$ and $R^3$ and $R^4$ are each hydrogen, then $R^2$ is not $CF_3$;
    when $R^6$ is $CF_3$ or $CHF_2$, $X^1$ is N, $X^2$ is CH, and one of $R^3$ or $R^4$ is hydrogen, then $R^2$ is not $CF_3$; and
    when $R^6$ is $CF_3$, $X^2$ is N, $X^1$ is CH, and one of $R^3$ or $R^4$ is hydrogen, then $R_2$ is not $CF^3$.

In some embodiments, the compound of Formula I is of the Formula II or III:

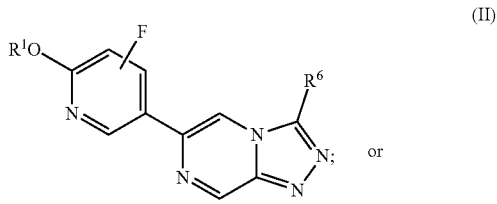

(II)

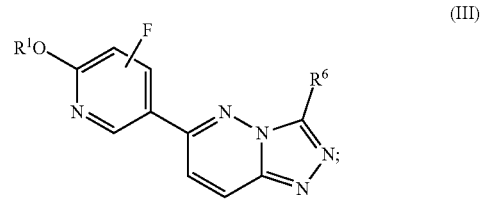

(III)

or a pharmaceutically acceptable salt thereof, wherein the variables are as defined herein.

In some embodiments, the compound of Formula I is of the Formula IV or V:

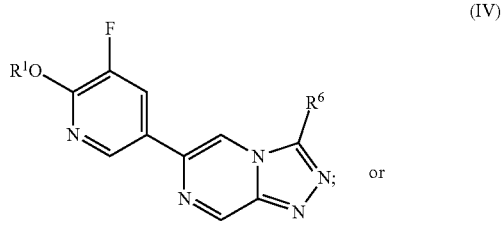

(IV)

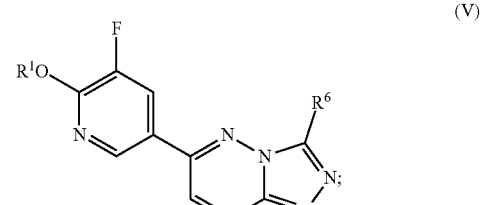

(V)

or a pharmaceutically acceptable salt thereof, wherein the variables are as defined herein.

In some embodiments, the compound of Formula I is of the Formula VI or VII:

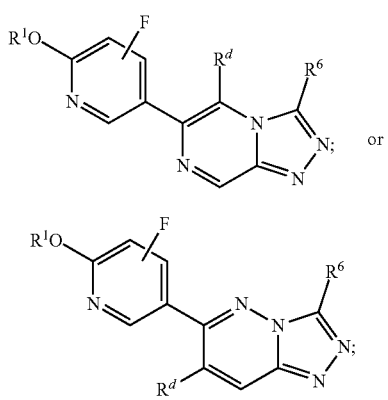

(VI)

(VII)

or a pharmaceutically acceptable salt thereof, wherein the variables are as defined herein.

In some embodiments, the compound of Formula I is of the Formula VIII or IX:

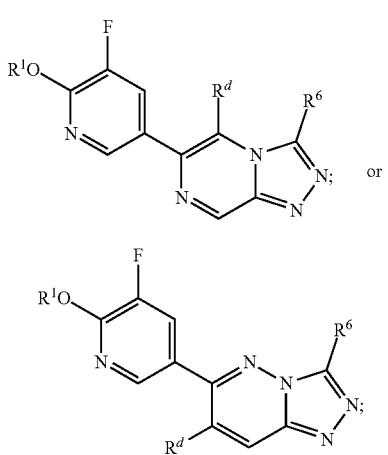

(VIII)

(IX)

or a pharmaceutically acceptable salt thereof, wherein the variables are as defined herein.

In some embodiments, the compound of Formula I is of the Formula X or XI:

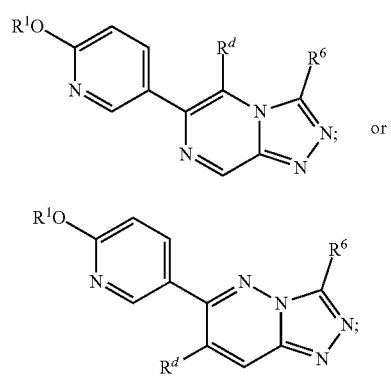

(X)

(XI)

or a pharmaceutically acceptable salt thereof, wherein the variables are as defined herein.

In another aspect, a pharmaceutical composition comprising a compound disclosed herein, or a pharmaceutically acceptable salt thereof, and a pharmaceutically acceptable carrier is provided.

In another aspect, provided herein is a method of treating a condition relating to aberrant function of a sodium ion channel in a subject, comprising administering to the subject a therapeutically effective amount of a compound disclosed herein (e.g., a compound of Formula I, II, III, IV, V, VI, VII, VIII, IX, X, or XI), or a pharmaceutically acceptable salt thereof, or a pharmaceutical composition disclosed herein.

In another aspect, provided herein is a method of treating a neurological disorder or a psychiatric disorder, wherein the method comprises administering to a subject in need thereof a compound disclosed herein (e.g., a compound of Formula I, II, III, IV, V, VI, VII, VIII, IX, X, or XI), or a pharmaceutically acceptable salt thereof, or a pharmaceutical composition disclosed herein.

Other objects and advantages will become apparent to those skilled in the art from a consideration of the ensuing Detailed Description, Examples, and Claims.

DETAILED DESCRIPTION

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include a neurological disorder (e.g., epilepsy or an epilepsy syndrome, a neurodevelopmental disorder or a neuromuscular disorder), a psychiatric disorder, pain, or a gastrointestinal disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

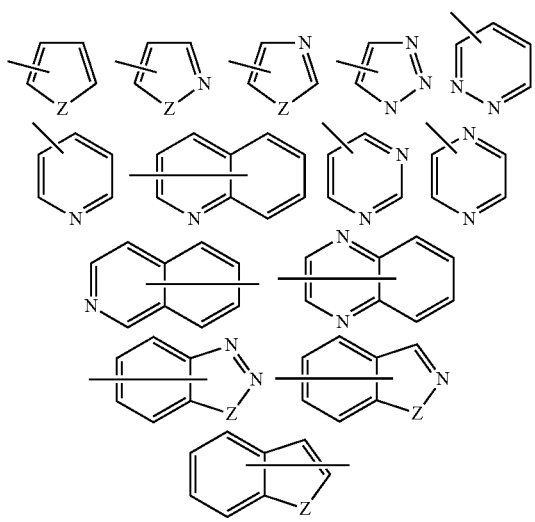

wherein each Z is selected from carbonyl, N, NR$^{65}$, O, and S; and R$^{65}$ is independently hydrogen, $C_{1-8}$ alkyl, $C_{3-10}$ carbocyclyl, 4-10 membered heterocyclyl, $C_6$-$C_{10}$ aryl, and 5-10 membered heteroaryl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocycyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

As used herein, "$C_{3-6}$ monocyclic cycloalkyl" or "monocyclic $C_{3-6}$ cycloalkyl" refers to a 3- to 7-membered monocyclic hydrocarbon ring system that is saturated. 3- to 7-membered monocyclic cycloalkyl groups include, without limitation, cyclopropyl, cyclobutyl, cyclopentyl, and cyclohexyl. Where specified as being optionally substituted or substituted, substituents on a cycloalkyl (e.g., in the case of an optionally substituted cycloalkyl) may be present on any substitutable position and, include, e.g., the position at which the cycloalkyl group is attached.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

In some embodiments, a heterocyclyl group is a 4-7 membered non-aromatic ring system having ring carbon atoms and 1-4 ring heteroatoms, wherein each heteroatom is independently selected from nitrogen, oxygen, and sulfur ("4-7 membered heterocyclyl"). In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Examples of saturated or partially unsaturated heterocyclic radicals include, without limitation, tetrahydrofuranyl, tetrahydrothienyl, tetrahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. Where specified as being optionally substituted or substituted, substituents on a heterocyclyl (e.g., in the case of an optionally substituted heterocyclyl) may be present on any substitutable position and, include, e.g., the position at which the heterocyclyl group is attached.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

As used herein, "cyano" refers to —CN.

The terms "halo" and "halogen" as used herein refer to an atom selected from fluorine (fluoro, —F), chlorine (chloro, —Cl), bromine (bromo, —Br), and iodine (iodo, —I). In certain embodiments, the halo group is either fluoro or chloro.

The term "alkoxy," as used herein, refers to an alkyl group which is attached to another moiety via an oxygen atom (—O(alkyl)). Non-limiting examples include e.g., methoxy, ethoxy, propoxy, and butoxy.

"Haloalkoxy" is a haloalkyl group which is attached to another moiety via an oxygen atom such as, e.g., but are not limited to —OCHCF$_2$ or —OCF$_3$.

The term "haloalkyl" includes mono, poly, and perhaloalkyl groups substituted with one or more halogen atoms where the halogens are independently selected from fluorine, chlorine, bromine, and iodine. For the group $C_{1-4}$haloalkyl-O—$C_{1-4}$alkyl, the point of attachment occurs on the alkyl moiety which is halogenated.

As used herein, "nitro" refers to —NO$_2$.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{bb}$)R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R$^{aa}$, —P(═O)(R$^{aa}$)$_2$, —P(═O)$_2$N(R$^{cc}$)$_2$, —P(═O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J.*

Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (also "therapeutic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternate embodiment, the present invention contemplates administration of the compounds of the present invention or a pharmaceutically acceptable salt or a pharmaceutically acceptable composition thereof, as a prophylactic before a subject begins to suffer from the specified disease, disorder or condition. As used herein, "prophylactic treatment" contemplates an action that occurs before a subject begins to suffer from the specified disease, disorder or condition. As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Compounds

In one aspect, the present invention features a compound of Formula I:

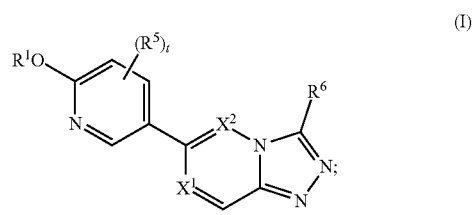

or a pharmaceutically acceptable salt thereof, wherein
$X^1$ is N and $X^2$ is $CR^d$, or $X^1$ is $CR^d$ and $X^2$ is N;
$R^1$ is selected from the group consisting of $—CR^2R^3R^4$, monocyclic $C_{3-6}$ cycloalkyl, and 4- to 7-membered monocyclic heterocyclyl, wherein said cycloalkyl and heterocyclyl are optionally substituted with one or more $R^a$;
$R^2$ is $C_{1-4}$haloalkyl or monocyclic $C_{3-6}$ cycloalkyl optionally substituted with one or more $R^b$;
$R^3$ is selected from the group consisting of hydrogen, $C_{1-4}$alkyl, and $C_{1-4}$haloalkyl;
$R^4$ is selected from the group consisting of hydrogen, $C_{1-4}$alkyl, and $C_{1-4}$haloalkyl;
$R^5$ is halo;
$R^6$ is $C_1$-$C_4$haloalkyl or $C_{3-6}$ monocyclic cycloalkyl, wherein said cycloalkyl for $R^6$ is optionally substituted with one or more $R^c$;
t is selected from the group consisting of 0, 1, and 2;
$R^a$, $R^b$, and $R^c$ are each independently selected from the group consisting of halo, $C_{1-4}$alkyl, $C_{1-4}$haloalkyl, $C_{1-4}$alkoxy, and $C_{1-4}$haloalkoxy; and
$R^d$ is selected from the group consisting of hydrogen, halo, and $C_{1-4}$ alkyl;

provided that:

when $R^3$ and $R^4$ are each hydrogen, then $R^6$ is not difluorocyclobutyl, fluorocyclopropyl, difluorocyclopropyl, cyclopropyl, or $CF_2Cl$;

when $R^6$ is $CF_3$ or $CHF_2$, then $R^1$ is not difluorocyclobutyl;

when $R^6$ is $CF_3$ or $CHF_2$ and $R^3$ and $R^4$ are each hydrogen, then $R^2$ is not $CF_3$;

when $R^6$ is $CF_3$ or $CHF_2$, $X^1$ is N, $X^2$ is CH, and one of $R^3$ or $R^4$ is hydrogen, then $R^2$ is not $CF_3$; and when $R^6$ is $CF_3$, $X^2$ is N, $X^1$ is CH, and one of $R^3$ or $R^4$ is hydrogen, then $R_2$ is not $CF^3$.

In some embodiments, the compound of Formula I is of the Formula II or III:

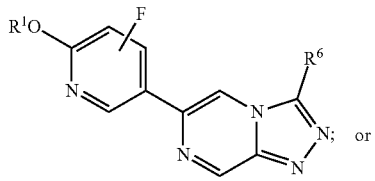
(II)

or

(III)

or a pharmaceutically acceptable salt thereof, wherein the variables are as described above for Formula I.

In some embodiments, the compound of Formula I is of the Formula IV or V:

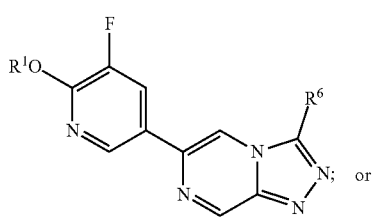
(IV)

or

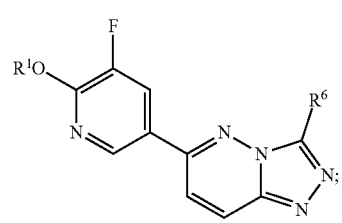
(V)

or a pharmaceutically acceptable salt thereof, wherein the variables are as described above for Formula I.

In some embodiments, the compound of Formula I is of the Formula VI or VII:

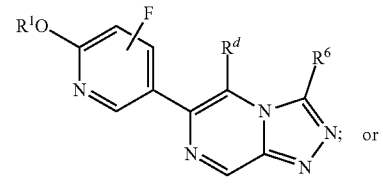
(VI)

or

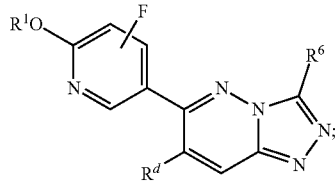
(VII)

or a pharmaceutically acceptable salt thereof, wherein the variables are as described above for Formula I.

In some embodiments, the compound of Formula I is of the Formula VIII or IX:

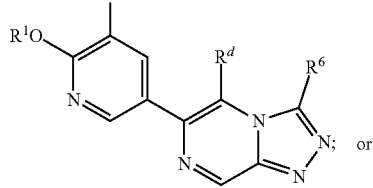
(VIII)

or

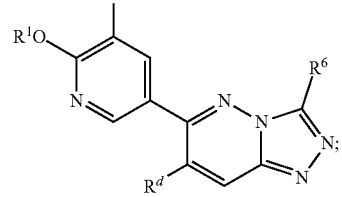
(IX)

or a pharmaceutically acceptable salt thereof, wherein the variables are as described above for Formula I.

In some embodiments, the compound of Formula I is of the Formula X or XI:

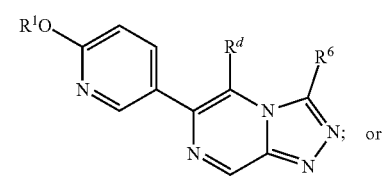
(X)

or

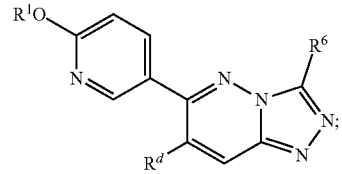
(XI)

or a pharmaceutically acceptable salt thereof, wherein the variables are as described above for Formula I.

In some embodiments, $R^1$ in the compound of Formula I, II, III, IV, V, VI, VII, VIII, IX, X, or XI is $-CR^2R^3R^4$. In some embodiments, $R^1$ in the compound of Formula I, II, III, IV, V, VI, VII, VIII, IX, X, or XI is oxetanyl or cyclobutyl, wherein said oxetanyl and cyclobutyl are each optionally substituted with one or more $R^a$.

In some embodiments, $R^2$ in the compound of Formula I, II, III, IV, V, VI, VII, VIII, IX, X, or XI is $C_{1-4}$haloalkyl or cyclopropyl optionally substituted with one or more $R^b$. In some embodiments, $R^2$ in the compound of Formula I, II, III, IV, V, VI, VII, VIII, IX, X, or XI is $C_{1-4}$haloalkyl. In some embodiments, $R^2$ in the compound of Formula I, II, III, IV, V, VI, VII, VIII, IX, X, or XI is $CF_3$.

In some embodiments, $R^3$ in the compound of Formula I, II, III, IV, V, VI, VII, VIII, IX, X, or XI is $C_{1-4}$alkyl and $R^4$ in the compound of Formula I, II, III, IV, V, VI, VII, VIII, IX, X, or XI is hydrogen or $C_{1-4}$alkyl. In some embodiments, $R^3$ and $R^4$ in the compound of Formula I, II, III, IV, V, VI, VII, VIII, IX, X, or XI are each $C_{1-4}$alkyl. In some embodiments, $R^3$ and $R^4$ in the compound of Formula I, II, III, IV, V, VI, VII, VIII, IX, X, or XI are each methyl. In some embodiments, $R^3$ in the compound of Formula I, II, III, IV, V, VI, VII, VIII, IX, X, or XI is methyl and $R^4$ in the compound of Formula I, II, III, IV, V, VI, VII, VIII, IX, X, or XI is hydrogen. In some embodiments, $R^3$ and $R^4$ in the compound of Formula I, II, III, IV, V, VI, VII, VIII, IX, X, or XI are each hydrogen. In some embodiments, $R^3$ in the compound of Formula I, II, III, IV, V, VI, VII, VIII, IX, X, or XI is $C_{1-4}$alkyl or $C_{1-4}$haloalkyl.

In some embodiments, $R^6$ in the compound of Formula I, II, III, IV, V, VI, VII, VIII, IX, X, or XI is selected from the group consisting of $C_{1-4}$haloalkyl, cyclopropyl, and cyclobutyl, wherein said cyclopropyl and cyclobutyl are each optionally substituted with one or more $R^c$. In some embodiments, $R^6$ in the compound of Formula I, II, III, IV, V, VI, VII, VIII, IX, X, or XI is selected from the group consisting of $CF_3$, $CHF_2$, 1,1-difluorocyclopropyl, and 1,1-difluorocyclobutyl. In some embodiments, $R^6$ in the compound of Formula I, II, III, IV, V, VI, VII, VIII, IX, X, or XI is $CF_3$ or $CHF_2$.

In some embodiments, $R^a$ in the compound of Formula I, II, III, IV, V, VI, VII, VIII, IX, X, or XI is halo or $C_{1-4}$haloalkyl. In some embodiments, $R^a$ in the compound of Formula I, II, III, IV, V, VI, VII, VIII, IX, X, or XI is $CF_3$ or fluoro.

In some embodiments, $R^b$ in the compound of Formula I, II, III, IV, V, VI, VII, VIII, IX, X, or XI is halo. In some embodiments, $R^b$ in the compound of Formula I, II, III, IV, V, VI, VII, VIII, IX, X, or XI is fluoro.

In some embodiments, $R^c$ in the compound of Formula I, II, III, IV, V, VI, VII, VIII, IX, X, or XI is halo. In some embodiments, $R^c$ in the compound of Formula I, II, III, IV, V, VI, VII, VIII, IX, X, or XI is fluoro.

In some embodiments, $R^d$ in the compound of Formula I, VI, VII, VIII, IX, X, or XI is methyl. In some embodiments, $R^d$ in the compound of Formula I, VI, VII, VIII, IX, X, or XI is chloro. In some embodiments, $R^d$ in the compound of Formula I, VI, VII, VIII, IX, X, or XI is hydrogen.

In some embodiments, t in the compound of Formula I is 0.

In some embodiments, t in the compound of Formula I is 1.

In some embodiments, $R^5$ in the compound of Formula I is fluoro.

In any and all aspects and embodiments, the compound of Formula I is selected from the group consisting of:

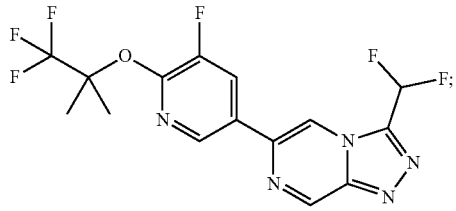

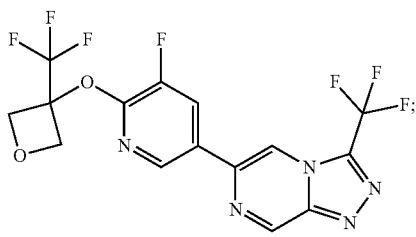

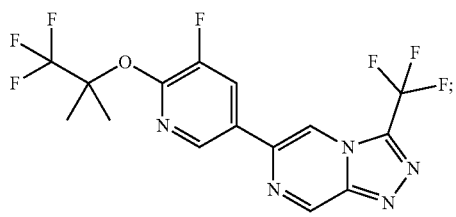

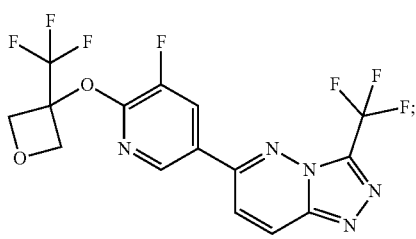

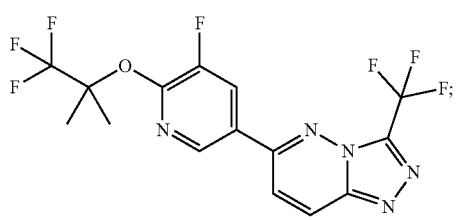

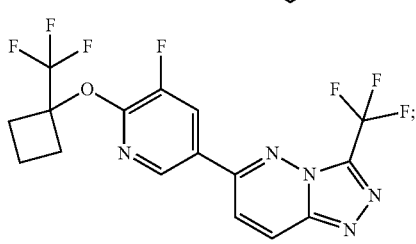

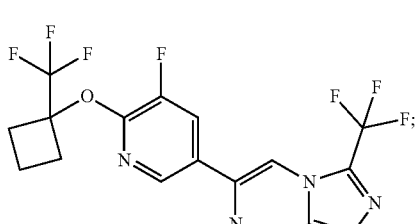

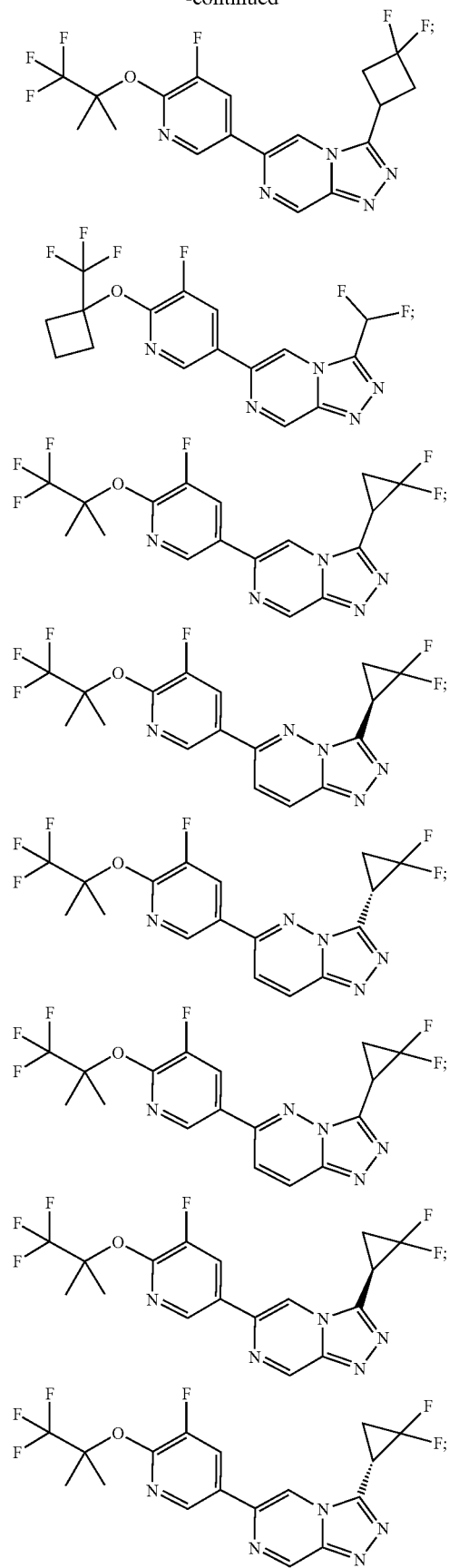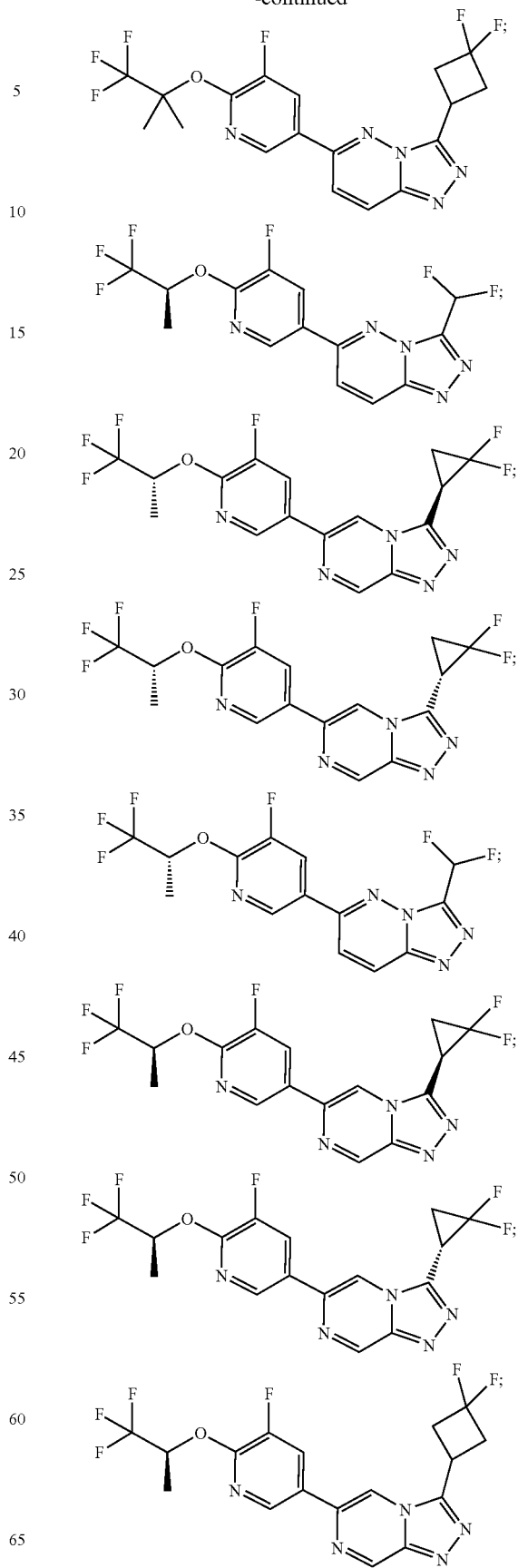

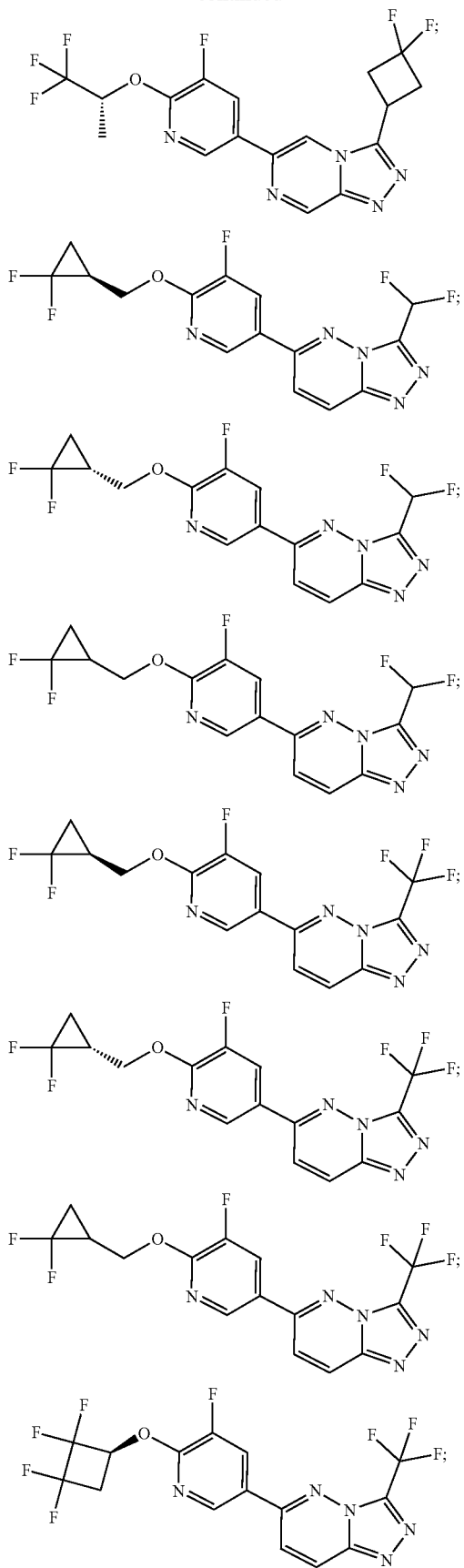
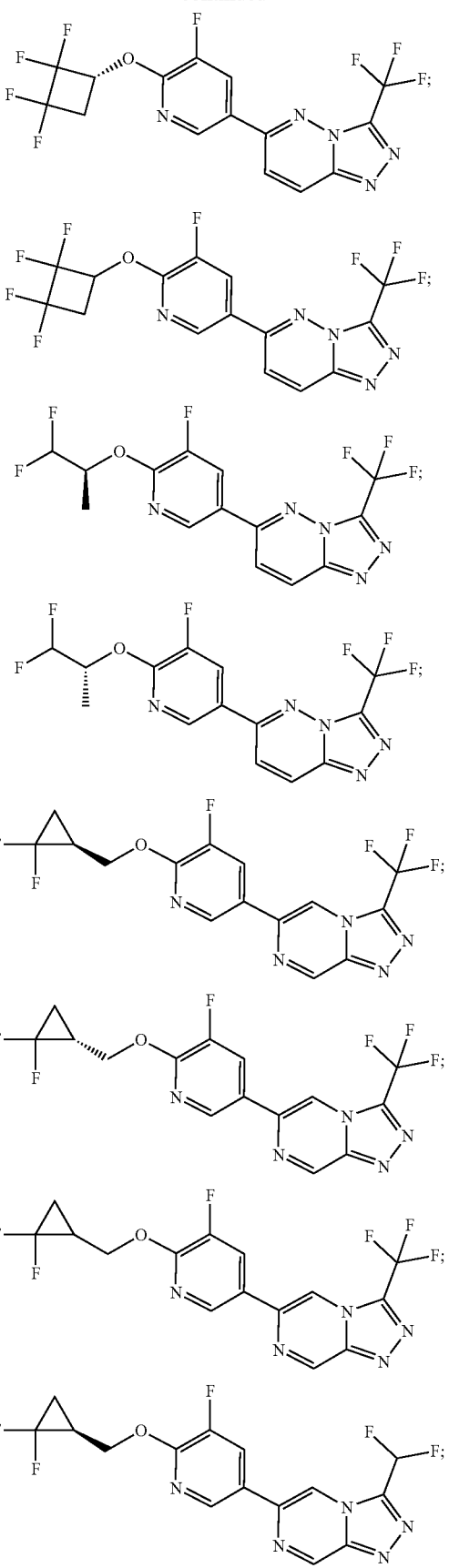

-continued
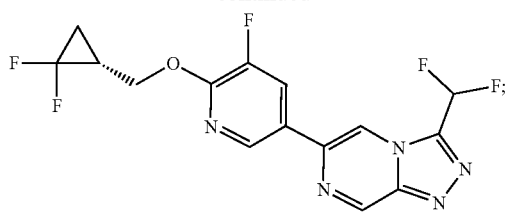
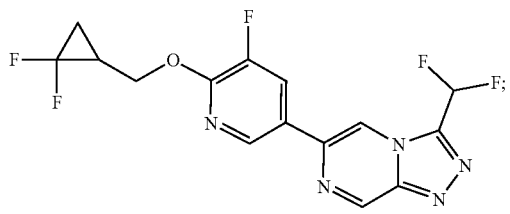
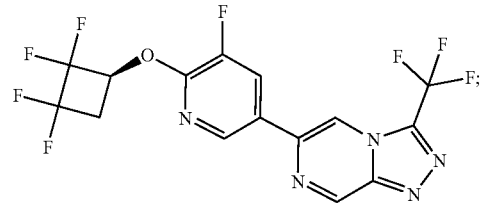
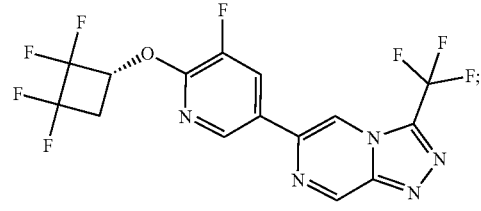
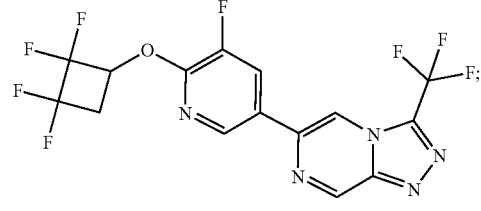
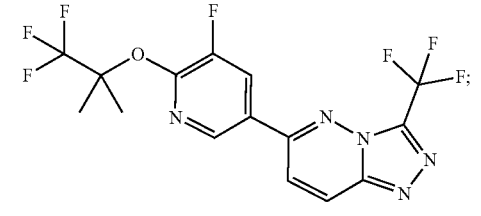
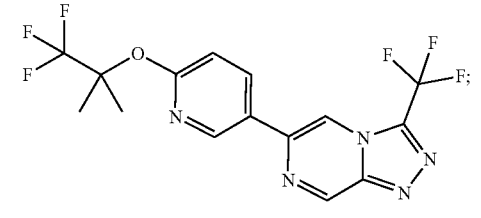
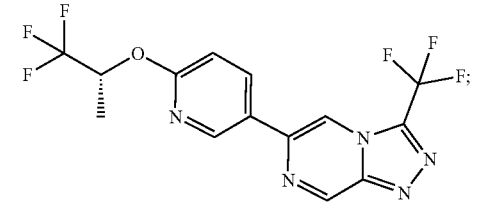
-continued
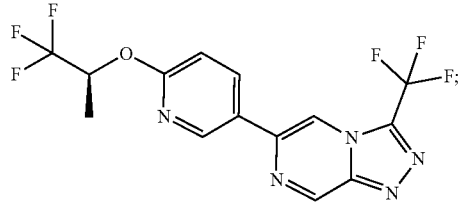
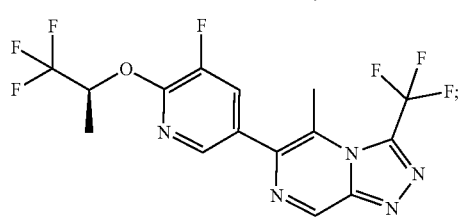
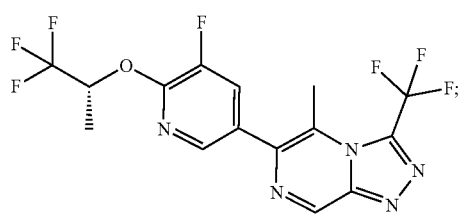
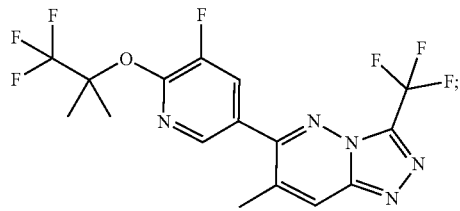
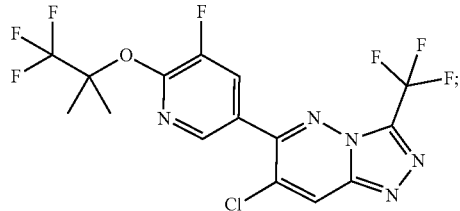
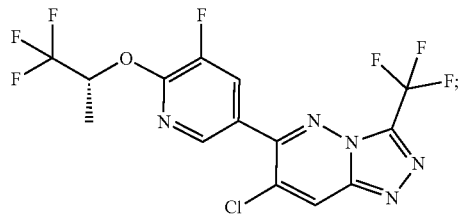
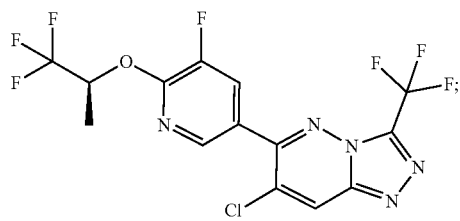
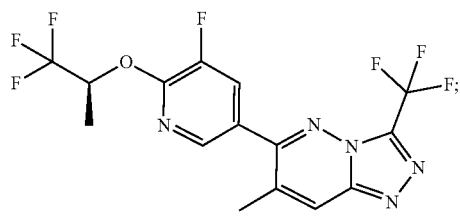

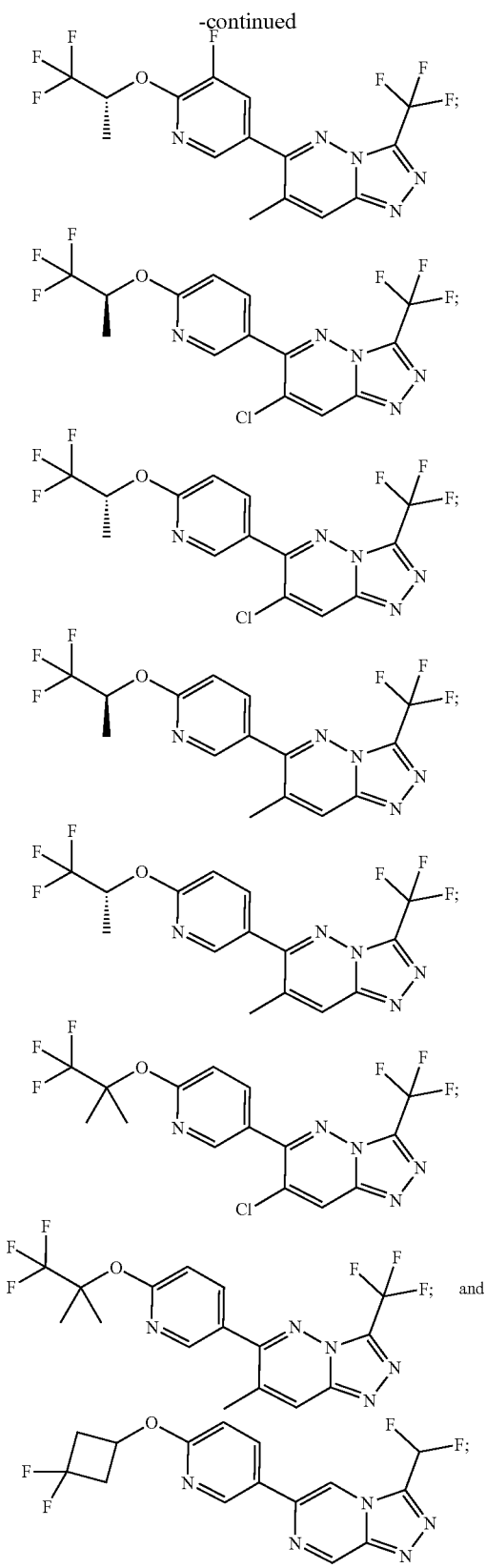

or a pharmaceutically acceptable salt thereof.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprising a disclosed compound, or pharmaceutically acceptable salt thereof, and a pharmaceutically acceptable carrier.

Methods of Use

Compounds and compositions described herein are generally useful for the modulating the activity of sodium channels and are useful in treating conditions relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. A provided compound, pharmaceutically acceptable salt thereof, or composition may also modulate all sodium ion channels, or may be specific to only one or a plurality of sodium ion channels, e.g., $Na_V$ 1.1, 1.2, 1.3, 1.4, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula I, II, III, IV, V, VI, VII, VIII, IX, X, or XI).

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and may actually turn blue. The return to consciousness is gradual and the person maybe confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein (e.g., a compound of Formula I, II, III, IV, V, VI, VII, VIII, IX, X, or XI) may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden unexpected death in epilepsy (SUDEP), KCNQ2 epileptic encephalopathy, or KCNT1 epileptic encephalopathy) prior to administration of a compound described herein (e.g., a compound of Formula I, II, III, IV, V, VI, VII, VIII, IX, X, or XI).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound of Formula (I):

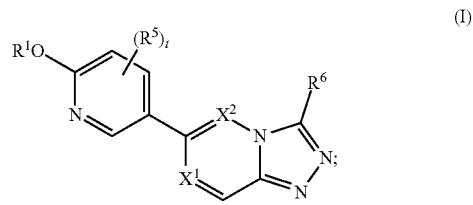

or a pharmaceutically acceptable salt thereof, wherein the variables are as defined herein.

A compound of the present invention (e.g., a compound of Formula I, II, III, IV, V, VI, VII, VIII, IX, X, or XI) may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula I, II, III, IV, V, VI, VII, VIII, IX, X, or XI).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula I, II, III, IV, V, VI, VII, VIII, IX, X, or XI).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound of Formula (I):

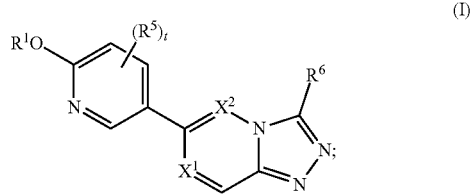

(I)

or a pharmaceutically acceptable salt thereof, wherein the variables are as defined herein.

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) prior to administration of a compound described herein (e.g., a compound of Formula I, II, III, IV, V, VI, VII, VIII, IX, X, or XI).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) comprising administering to a subject in need thereof a compound of Formula (I):

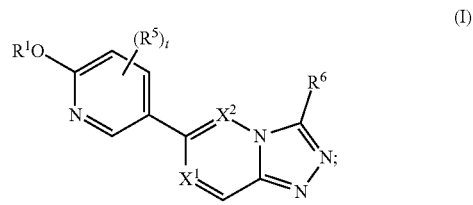

(I)

or a pharmaceutically acceptable salt thereof, wherein the variables are as defined herein.

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula I, II, III, IV, V, VI, VII, VIII, IX, X, or XI).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound of Formula (I):

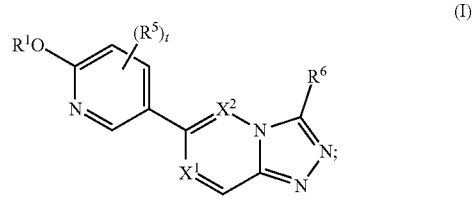

(I)

or a pharmaceutically acceptable salt thereof, wherein the variables are as defined herein.

Other Disorders

In some embodiments, a compound of the present invention (e.g., a compound of Formula I, II, III, IV, V, VI, VII, VIII, IX, X, or XI) may have appropriate pharmacokinetic properties such that they may be active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, recurrent ischemia, cerebral ischemia, stroke, renal ischemia, ischemia associated with organ transplant, acute coronary syndrome, peripheral arterial disease, intermittent claudication, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy.

In some embodiments, a disclosed method comprises administering the pharmaceutical composition.

In some embodiments, provided herein is a method of treating a neurological disorder or a psychiatric disorder, wherein the method comprises administering to a subject in need thereof a compound disclosed herein, or a pharmaceutically acceptable salt thereof or a pharmaceutical composition disclosed herein.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide, and cannabidiol.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra). Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics-platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amioarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol;

NSAIDs, and COX-2 inhibitors. Given the ability of the sodium channel blockers of the invention to treat neuropathic pain via inhibition of the $Na_V$ 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; benzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban). Antidepressant and anti-anxiety agents may include neuroactive steroid and ketamine and related NMDA receptor antagonists.

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel blockers of the invention and therapeutic agent or agents, essentially contemporaneous administration of more than one formulation comprising the sodium channel blocker of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXEMPLIFICATION

The representative examples that follow are intended to help illustrate the invention, and are not intended to, nor should they be construed to, limit the scope of the invention.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate $C_{18}$ (2.1 mm×30 mm, 3 µm); A=$H_2O$ (0.04% TFA) and B=$CH_3CN$ (0.02% TFA); 50° C.; 1.2 mL/min; 10-80% B over 0.9 minutes, then 80% B for 0.6 minutes) and Method B (Chromolith Flash RP-18 endcapped $C_{18}$ (2 mm×25 mm); A=$H_2O$ (0.04% TFA) and B=$CH_3CN$ (0.02% TFA); 50° C.; 1.5 mL/min; 5-95% B over 0.7 minutes, then 95% B for 0.4 minutes).

LIST OF ABBREVIATIONS $Pd(dppf)Cl_2$ [1,1'-bis(diphenylphosphino)ferrocene]palladium(II) dichloride
$Et_3N$ triethylamine
THF tetrahydrofuran
EtOAc ethyl acetate
PE petroleum ether
KOAc potassium acetate
$Pd(t-Bu_3P)_2$ bis(tri-tert-butylphosphine)palladium(0)
DMF N,N-dimethylformamide
MeOH methanol
NBS N-bromosuccinimide
DCM dichloromethane
EtOH ethanol
MeCN acetonitrile
TBAF tetrabutylammonium fluoride
DMSO dimethyl sulfoxide
EDCI 1-ethyl-3-(3-dimethylaminopropyl)carbodiimide
HOBt hydroxybenzotriazole
DIPEA N,N-diisopropylethylamine
DEA diethanolamine
$Cy_3PH^+BF_4^-$ tricyclohexylphosphine tetrafluroborate
$Pd(OAc)_2$ palladium(II) acetate
$KO^tBu$ potassium tert-butoxide
TFA trifluoroacetic acid
AcOH acetic acid Example 1: 3-(difluoromethyl)-6-[5-fluoro-6-(2,2,2-trifluoro-1,1-dimethyl-ethoxy)-3-pyridyl]-[1,2,4]triazolo[4,3-a]pyrazine

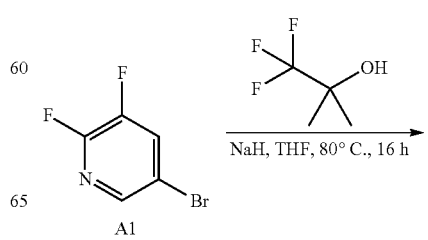

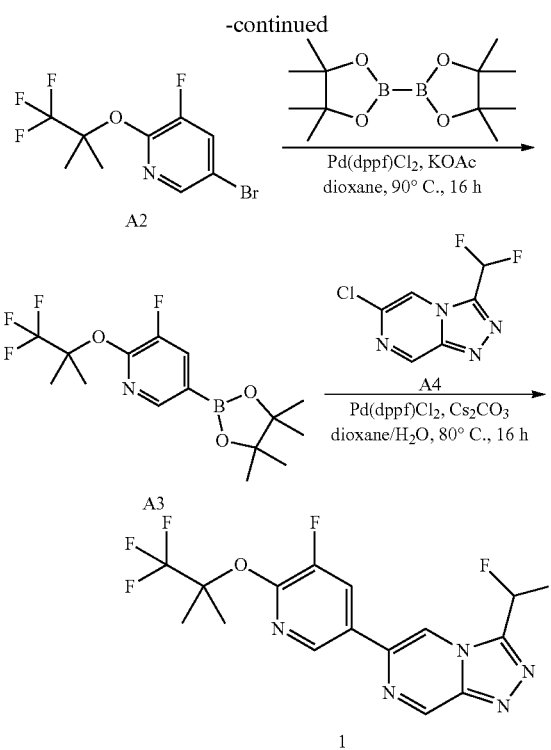

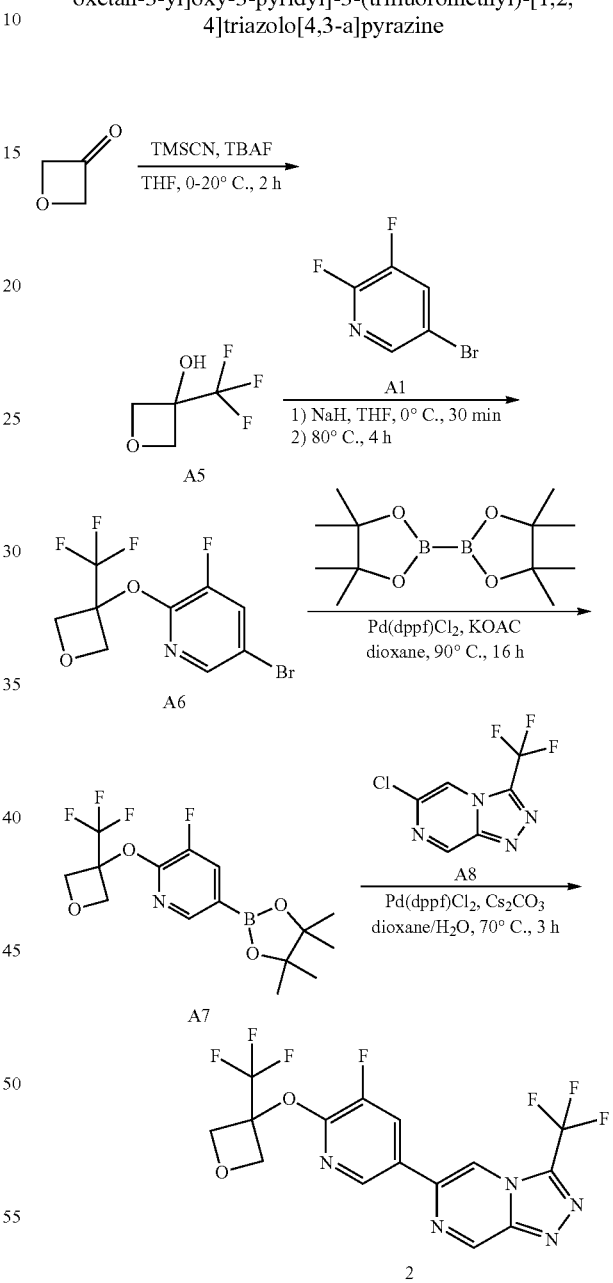

Synthesis of A2: To a solution of 1,1,1-trifluoro-2-methyl-propan-2-ol (3 g, 23.42 mmol) in THF (10 mL) was added NaH (936.84 mg, 23.42 mmol). Then to the mixture was added 5-bromo-2,3-difluoro-pyridine (4.54 g, 23.42 mmol), and the mixture was stirred at 80° C. for 16 hours. After cooling to room temperature, the mixture was diluted with H₂O (10 mL) and extracted with EtOAc (10 mL×2). The combined organic phase was washed with brine (10 mL), dried over Na₂SO₄, filtered and concentrated to give the crude product. The crude product was purified by flash chromatography on silica gel (EtOAc in PE=0% to 2%) to give the product (2800 mg, 9.27 mmol, 39.58% yield) as an oil. ¹H NMR (400 MHz, CDCl₃) $\delta_H$=7.99 (d, 1H), 7.54 (dd, 1H), 1.80 (d, 6H).

Synthesis of A3: A mixture of 5-bromo-3-fluoro-2-(2,2,2-trifluoro-1,1-dimethyl-ethoxy)pyridine (1.5 g, 4.97 mmol), 4,4,5,5-tetramethyl-2-(4,4,5,5-tetramethyl-1,3,2-dioxaborolan-2-yl)-1,3,2-dioxaborolane (1.89 g, 7.45 mmol), Pd(dppf)Cl₂ (545.03 mg, 0.74 mmol) and KOAc (974.71 mg, 9.93 mmol) in 1,4-Dioxane (20 mL) was stirred at 90° C. for 16 hours. After cooling to room temperature, the suspension was diluted with EtOAc (10 mL), filtered through silica gel, eluted with EtOAc (20 mL). The filtrate was concentrated to give the crude product. The crude product was purified by flash chromatography on silica gel (EtOAc in PE=0% to 10%) to give the product (1000 mg, 2.86 mmol, 58% yield) as a solid. ¹H NMR (400 MHz, CDCl₃) $\delta_H$=8.26 (d, 1H), 7.67 (dd, 1H), 1.83 (s, 6H), 1.34 (s, 12H).

Synthesis of Compound 1: A mixture of 6-chloro-3-(difluoromethyl)-[1,2,4]triazolo[4,3-a]pyrazine (100 mg, 0.49 mmol), Pd(dppf)Cl₂ (53.65 mg, 0.07 mmol), Cs₂CO₃, with EtOAc (20 mL×2). The combined organic phase was washed with brine (10 mL), dried over Na₂SO₄, filtered and concentrated to give the crude product. The crude product was purified by Prep-HPLC (Waters Xbridge (150 mm×25 mm, 10 μm) μA=H₂O (10 mM NH₄HCO₃) and B=CH₃CN; 48-78% B over 6 minutes) to give the product (74.73 mg, 0.19 mmol) as a solid. ¹H NMR (400 MHz, DMSO-d₆) $\delta_H$=9.69 (d, 1H), 9.29 (d, 1H), 8.78 (d, 1H), 8.47 (dd, 1H), 7.82 (t, 1H), 1.83 (s, 6H). LCMS R$_t$=1.14 min in 2 min chromatography, MS ESI calcd. for C₁₅H₁₂F₆N₅O [M+H]⁺ 392.1, found 392.0.

Example 2: 6-[5-fluoro-6-[3-(trifluoromethyl)oxetan-3-yl]oxy-3-pyridyl]-3-(trifluoromethyl)-[1,2,4]triazolo[4,3-a]pyrazine Synthesis of A5: To a colorless mixture of trimethyl(trifluoromethyl)silane (2.57 g, 18.04 mmol) and oxetan-3-one (1 g, 13.88 mmol) in THF (10 mL) was added TBAF (0.14 mL, 0.14 mmol) at 0° C., then the mixture was stirred at 20° C. for 2 hours. The mixture was neutralized with 1M HCl (20 mL), and the mixture was stirred at 20° C. for 2 hours. The mixture was extracted with DCM (30 mL×2). The combined organic phase was washed with water (10 mL) and brine (10 mL), dried over Na$_2$SO$_4$, filtered and concentrated to give the crude product (1000 mg, 7.04 mmol, 51% yield) as an oil. $^1$H NMR (400 MHz, CDCl$_3$) $\delta_H$=4.83 (d, 2H), 4.66 (d, 2H), 3.53 (s, 1H).

Synthesis of A6: To a solution of 3-(trifluoromethyl) oxetan-3-ol (1 g, 7.04 mmol) in THF (50 mL) was added NaH (206.21 mg, 5.16 mmol) at 0° C., and the mixture was stirred for 30 min. Then to the mixture was added 5-bromo-2,3-difluoro-pyridine (1 g, 5.16 mmol), and the mixture was stirred at 80° C. for 4 hours. After cooling to room temperature, the mixture was poured into ice water and stirred for 30 min. Then the mixture was diluted with sat. NH$_4$Cl (20 mL) and extracted with EtOAc (50 mL×2). The combined organic phase was washed with brine (20 mL), dried over Na$_2$SO$_4$, filtered and concentrated to give the crude product (750 mg, 2.37 mmol, 46% yield) as an oil. $^1$H NMR (400 MHz, CDCl$_3$) $\delta_H$=7.94 (d, 1H), 7.60 (dd, 1H), 5.13-5.07 (m, 2H), 5.0-4.95 (m, 2H).

Synthesis of A7: A mixture of 5-bromo-3-fluoro-2-[3-(trifluoromethyl)oxetan-3-yl]oxy-pyridine (600 mg, 1.9 mmol), 4,4,5,5-tetramethyl-2-(4,4,5,5-tetramethyl-1,3,2-dioxaborolan-2-yl)-1,3,2-dioxaborolane (482.09 mg, 1.9 mmol), Pd(dppf)Cl$_2$ (208.36 mg, 0.28 mmol) and KOAc (372.62 mg, 3.8 mmol) in 1,4-Dioxane (20 mL) was stirred at 90° C. for 16 hours under N$_2$. The mixture was cooled to room temperature and concentrated to give a residue. The residue was diluted with EtOAc/PE (1:10, 20 mL), filtered with silica gel, eluted with EtOAc/PE (1:10, 50 mL) and concentrated to give the crude product (500 mg, 1.38 mmol, 73% yield) as an oil. $^1$H NMR (400 MHz, CDCl$_3$) $\delta_H$=8.20 (d, 1H), 7.74 (dd, 1H), 5.15-5.10 (m, 2H), 5.01-4.97 (m, 2H), 1.34 (s, 12H).

Synthesis of Compound 2: A mixture of 6-chloro-3-(trifluoromethyl)-[1,2,4]triazolo[4,3-a]pyrazine (80 mg, 0.36 mmol), Pd(dppf)Cl$_2$ (39.45 mg, 0.05 mmol), Cs$_2$CO$_3$ (234.22 mg, 0.72 mmol), and 3-fluoro-5-(4,4,5,5-tetramethyl-1,3,2-dioxaborolan-2-yl)-2-[3-(trifluoromethyl) oxetan-3-yl]oxy-pyridine (130.52 mg, 0.36 mmol) in 1,4-Dioxane (2 mL) and Water (0.20 mL) was stirred at 70° C. for 3 hours. The residue was diluted with H$_2$O (20 mL) and extracted with EtOAc (20 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 47-67% B over 6 minutes) to give the product (13.26 mg, 31.2 μmol) as a solid. $^1$H NMR (400 MHz, CDCl$_3$) $\delta_H$=9.60 (d, 1H), 8.47 (d, 1H), 8.42 (s, 1H), 8.13 (dd, 1H), 5.17 (d, 2H), 5.04 (d, 2H). LCMS R$_t$=1.04 min in 2.0 min chromatography, MS ESI calcd. for C$_{15}$H$_9$F$_7$N$_5$O$_2$ [M+H]$^+$ 424.1, found 423.9.

Example 3: 6-[5-fluoro-6-(2,2,2-trifluoro-1,1-dimethyl-ethoxy)-3-pyridyl]-3-(trifluoromethyl)-[1,2,4]triazolo[4,3-a]pyrazine

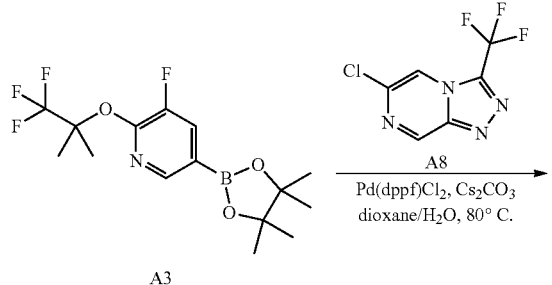

A3

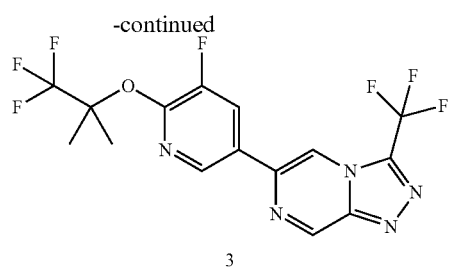

3

A mixture of 6-chloro-3-(trifluoromethyl)-[1,2,4]triazolo[4,3-a]pyrazine (100 mg, 0.45 mmol), Pd(dppf)Cl$_2$ (49.31 mg, 0.07 mmol), Cs$_2$CO$_3$ (292.77 mg, 0.90 mmol) and 3-fluoro-5-(4,4,5,5-tetramethyl-1,3,2-dioxaborolan-2-yl)-2-(2,2,2-trifluoro-1,1-dimethyl-ethoxy)pyridine (235.31 mg, 0.67 mmol) in 1,4-Dioxane (2 mL) and Water (0.20 mL) was stirred at 80° C. for 16 hours. After cooling to room temperature, the mixture was concentrated to a residue. The residue was diluted with H$_2$O (20 mL) and extracted with EtOAc (20 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 10 μm) A=H$_2$O (10 mM NH$_4$HCO$_3$) and B=CH$_3$CN; 55-75% B over 6 minutes) to give the product (81.74 mg, 0.20 mmol) as a solid. $^1$H NMR (400 MHz, CDCl$_3$) $\delta_H$=9.59 (d, 1H), 8.53 (d, 1H), 8.40 (s, 1H), 8.03 (dd, 1H), 1.89 (s, 6H). LCMS R$_t$=1.09 min in 2 min chromatography, MS ESI calcd. for C$_{15}$H$_{11}$F$_7$N$_5$O [M+H]$^+$ 410.1, found 410.0.

Example 4: 6-[5-fluoro-6-[3-(trifluoromethyl) oxetan-3-yl]oxy-3-pyridyl]-3-(trifluoromethyl)-[1,2,4]triazolo[4,3-b]pyridazine

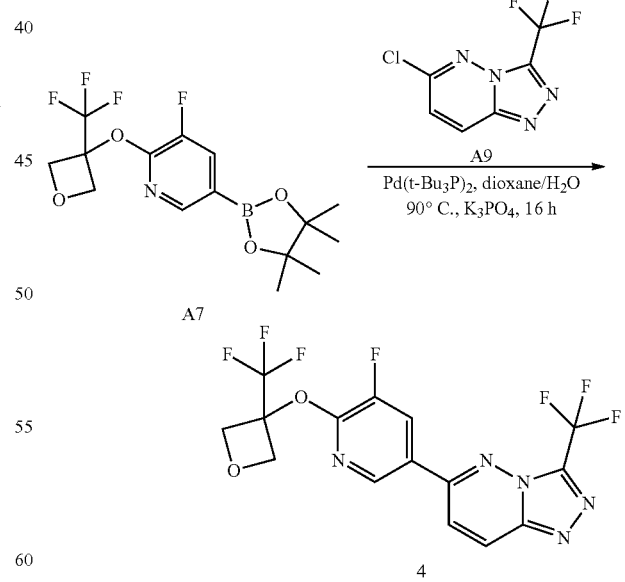

A mixture of 3-fluoro-5-(4,4,5,5-tetramethyl-1,3,2-dioxaborolan-2-yl)-2-[3-(trifluoromethyl)oxetan-3-yl]oxy-pyridine (130.52 mg, 0.36 mmol), Pd(t-Bu$_3$P)$_2$ (27.55 mg, 0.05 mmol), K$_3$PO$_4$ (152.62 mg, 0.72 mmol), and 6-chloro-3-(trifluoromethyl)-[1,2,4]triazolo[4,3-b]pyridazine (80 mg, 0.36 mmol) in 1,4-Dioxane (2 mL) and Water (0.20 mL) was stirred at 90° C. for 16 hours. After cooling to room temperature, the mixture was concentrated to a residue. The residue was diluted with H₂O (20 mL) and extracted with EtOAc (20 mL×2). The combined organic phase was washed with brine (10 mL), dried over Na₂SO₄, filtered and concentrated to give the crude product. The crude product was purified by Prep-HPLC (Waters Xbridge (150 mm×25 mm, 5 μm), A=H₂O (10 mM NH₄HCO₃) and B=CH₃CN; 47-67% B over 6 minutes) to give the product (27.05 mg, 63.6 μmol) as a solid. $^1$H NMR (400 MHz, CDCl₃) $\delta_H$=8.52 (d, 1H), 8.37 (d, 1H), 8.17 (dd, 1H), 7.72 (d, 1H), 5.17 (d, 2H), 5.05 (d, 2H). LCMS $R_t$=1.05 min in 2.0 min chromatography, MS ESI calcd. for $C_{15}H_9F_7N_5O_2$ [M+H]⁺ 424.0, found 424.0.

Example 5: 3-(difluoromethyl)-6-[5-fluoro-6-(2,2,2-trifluoro-1,1-dimethyl-ethoxy)-3-pyridyl]-[1,2,4]triazolo[4,3-b]pyridazine

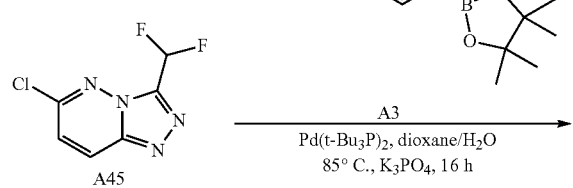

A mixture of 3-fluoro-5-(4,4,5,5-tetramethyl-1,3,2-dioxaborolan-2-yl)-2-(2,2,2-trifluoro-1,1-dimethyl-ethoxy)pyridine (409.62 mg, 1.17 mmol), 6-chloro-3-(difluoromethyl)-[1,2,4]triazolo[4,3-b]pyridazine (200 mg, 0.98 mmol), Pd(t-Bu₃P)₂ (74.95 mg, 0.15 mmol), and K₃PO₄ (415.13 mg, 1.96 mmol) in 1,4-Dioxane (10 mL) and water (1 mL) was stirred at 85° C. for 16 hours. After cooling to room temperature, the suspension was diluted with EtOAc (10 mL), filtered through silica gel and eluted with EtOAc (20 mL). The combined filtrates were concentrated to afford crude product. The crude product was purified by Prep-HPLC (Waters Xbridge (150 mm×25 mm, 5 μm) A=H₂O (10 mM NH₄HCO₃) and B=CH₃CN; 47-60% B over 9 minutes) to give the product (89 mg, 0.23 mmol) as a solid. $^1$H NMR (400 MHz, DMSO-d₆) $\delta_H$=8.86 (d, 1H), 8.67 (d, 1H), 8.53 (dd, 1H), 8.20 (d, 1H), 7.99-7.68 (t, 1H), 1.86 (s, 6H). LCMS $R_t$=1.30 min in 2 min chromatography, MS ESI calcd. for $C_{15}H_{12}F_6N_5O$ [M+H]⁺ 392.1, found 392.0.

Example 6: 6-[5-fluoro-6-[1-(trifluoromethyl)cyclobutoxy]-3-pyridyl]-3-(trifluoromethyl)-[1,2,4]triazolo[4,3-b]pyridazine

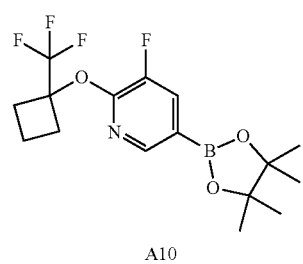
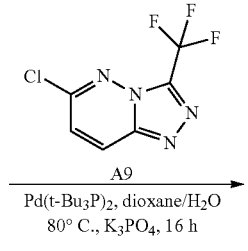
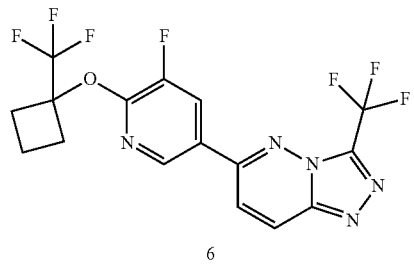

A mixture of 6-chloro-3-(trifluoromethyl)-[1,2,4]triazolo[4,3-b]pyridazine (80 mg, 0.36 mmol), Pd(t-Bu₃P)₂ (27.55 mg, 0.05 mmol), K₃PO₄ (152.62 mg, 0.72 mmol), and 3-fluoro-5-(4,4,5,5-tetramethyl-1,3,2-dioxaborolan-2-yl)-2-[1-(trifluoromethyl)cyclobutoxy]pyridine (155.78 mg, 0.43 mmol) in 1,4-Dioxane (2 mL) and Water (0.20 mL) was stirred under N₂ at 80° C. for 16 hours. The mixture was cooled to room temperature, diluted with EtOAc (10 mL), filtered through silica gel, eluted with EtOAc (10 mL) and concentrated to give the crude product. The crude product was purified by Prep-HPLC (Waters Xbridge (150 mm×25 mm, 5 μm), A=H₂O (10 mM NH₄HCO₃) and B=CH₃CN; 55-75% B over 7 minutes) to give the product (8.01 mg, 18.8 mmol) as a solid. $^1$H NMR (400 MHz, CDCl₃) $\delta_H$=8.56 (d, 1H), 8.35 (d, 1H), 8.11 (dd, 1H), 7.73 (d, 1H), 2.97-2.86 (m, 2H), 2.85-2.75 (m, 2H), 2.10-1.95 (m, 2H). LCMS $R_t$=1.16 min in 2.0 min chromatography, MS ESI calcd. for $C_{16}H_{11}F_7N_5O$ [M+H]⁺ 422.1, found 422.0.

Example 7: 6-[5-fluoro-6-[1-(trifluoromethyl)cyclobutoxy]-3-pyridyl]-3-(trifluoromethyl)-[1,2,4]triazolo[4,3-a]pyrazine

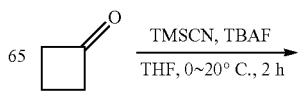

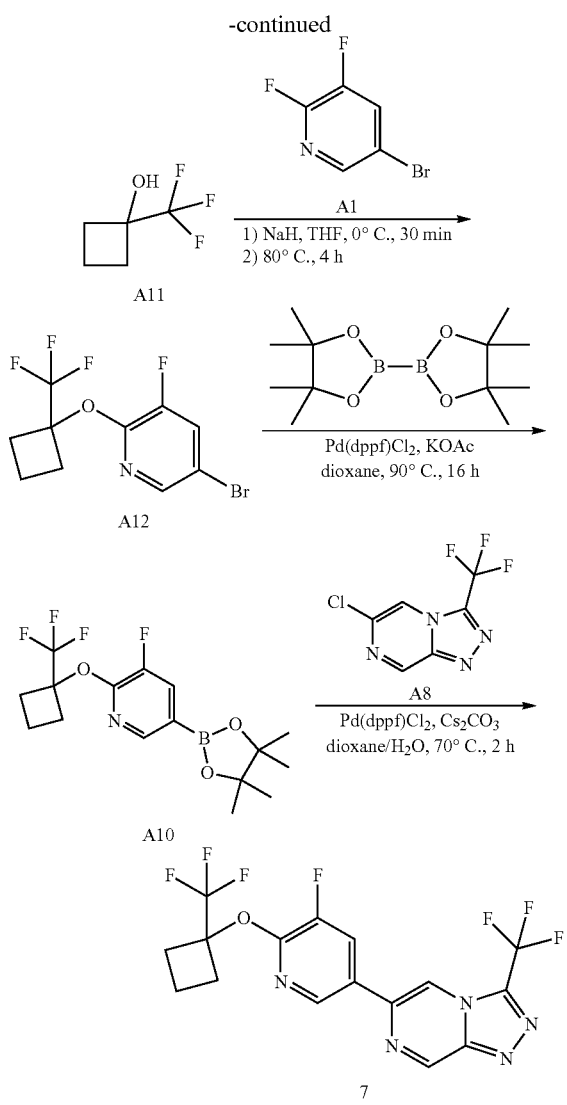

the crude product. $^1$H NMR (400 MHz, DMSO-$d_6$) $\delta_H$=8.21 (dd, 1H), 8.16 (d, 1H), 2.88-2.76 (m, 2H), 2.65-2.56 (m, 2H), 1.97-1.88 (m, 1H), 1.87-1.76 (m, 1H).

Synthesis of A10: A mixture of 5-bromo-3-fluoro-2-[1-(trifluoromethyl)cyclobutoxy]pyridine (400 mg, 1.27 mmol), 4,4,5,5-tetramethyl-2-(4,4,5,5-tetramethyl-1,3,2-dioxaborolan-2-yl)-1,3,2-dioxaborolane (323.42 mg, 1.27 mmol), Pd(dppf)Cl$_2$ (139.78 mg, 0.19 mmol) and KOAc (249.98 mg, 2.55 mmol) in 1,4-Dioxane (20 mL) was stirred at 90° C. for 16 hours under N$_2$. The mixture was cooled to room temperature and concentrated to give a residue. The residue was diluted with EtOAc/PE (1:10, 20 mL), filtered through silica gel, eluted with EtOAc/PE (1:10, 50 mL) and concentrated to give the crude product (500 mg, crude) as an oil. $^1$H NMR (400 MHz, CDCl$_3$) $\delta_H$=8.27 (d, 1H), 7.68 (dd, 1H), 2.99-2.84 (m, 2H), 2.77-2.64 (m, 2H), 2.02-1.91 (m, 2H), 1.36-1.33 (m, 12H).

Synthesis of Compound 7: A mixture of 6-chloro-3-(trifluoromethyl)-[1,2,4]triazolo[4,3-a]pyrazine (80 mg, 0.36 mmol), Pd(dppf)Cl$_2$ (39.45 mg, 0.05 mmol), Cs$_2$CO$_3$ (234.22 mg, 0.72 mmol), and 3-fluoro-5-(4,4,5,5-tetramethyl-1,3,2-dioxaborolan-2-yl)-2-[1-(trifluoromethyl)cyclobutoxy]pyridine (155.78 mg, 0.43 mmol) in 1,4-Dioxane (2 mL) and Water (0.20 mL) was stirred under N$_2$ at 70° C. for 2 hours. The mixture was cooled to room temperature, diluted with EtOAc (10 mL), filtered through silica gel, eluted with EtOAc (10 mL) and concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 52-72% B over 7 minutes) to give the product (28.31 mg, 67.2 μmol) as a solid. $^1$H NMR (400 MHz, CDCl$_3$) $\delta_H$=9.59 (d, 1H), 8.51 (d, 1H), 8.41 (s, 1H), 8.06 (dd, 1H), 2.98-2.87 (m, 2H), 2.82-2.72 (m, 2H), 2.10-1.93 (m, 2H). LCMS R$_t$=1.14 min in 2.0 min chromatography, MS ESI calcd. for C$_{16}$H$_{11}$F$_7$N$_5$O [M+H]$^+$ 422.1, found 422.0.

Example 8: 3-(3,3-difluorocyclobutyl)-6-[5-fluoro-6-(2,2,2-trifluoro-1,1-dimethyl-ethoxy)-3-pyridyl]-[1,2,4]triazolo[4,3-a]pyrazine

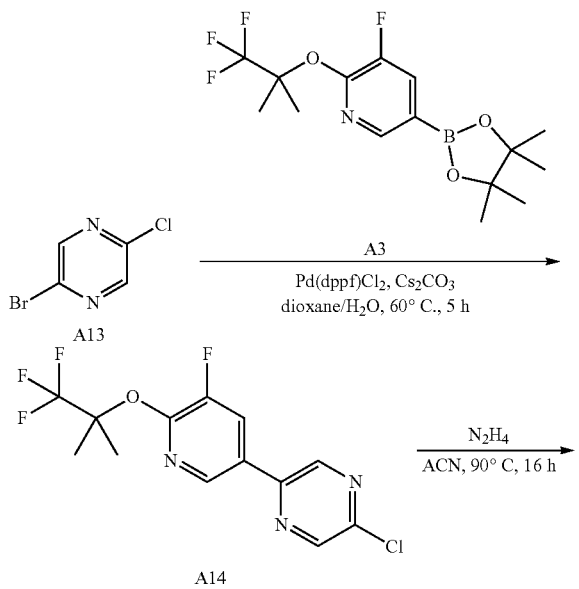

Synthesis of A11: To a mixture of cyclobutanone (500 mg, 7.13 mmol) and trimethyl(trifluoromethyl)silane (1.32 g, 9.27 mmol) in THF (10 mL) was added TBAF (0.07 mL, 0.07 mmol) at 0° C., then the mixture was stirred at 20° C. for 2 hours. The mixture was neutralized with 1M HCl (10 mL), then the mixture was stirred at 20° C. for 1 hour. The mixture was extracted with DCM (30 mL×2). The combined organic phase was washed with water (10 mL) and brine (10 mL), dried over Na$_2$SO$_4$, filtered and concentrated to give the crude product (450 mg, 3.21 mmol, 45% yield) as an oil. $^1$H NMR (400 MHz, DMSO-$d_6$) $\delta_H$=6.40 (s, 1H), 2.38-2.27 (m, 2H), 2.18-2.04 (m, 2H), 1.90-1.79 (m, 1H), 1.74-1.60 (m, 1H).

Synthesis of A12: To a solution of 1-(trifluoromethyl)cyclobutanol (216.67 mg, 1.55 mmol) in THF (10 mL) was added NaH (61.86 mg, 1.55 mmol) at 0° C., and the mixture was stirred for 30 min. Then to the mixture was added 5-bromo-2,3-difluoro-pyridine (300.mg, 1.55 mmol), and the mixture was stirred at 80° C. for 4 hours. After cooling to room temperature, the mixture was pour into ice water and stirred for 30 mins. Then the mixture was diluted with sat. NH$_4$Cl (20 mL) and extracted with EtOAc (50 mL×2). The combined organic phase was washed with brine (20 mL), dried over Na$_2$SO$_4$, filtered and concentrated to give

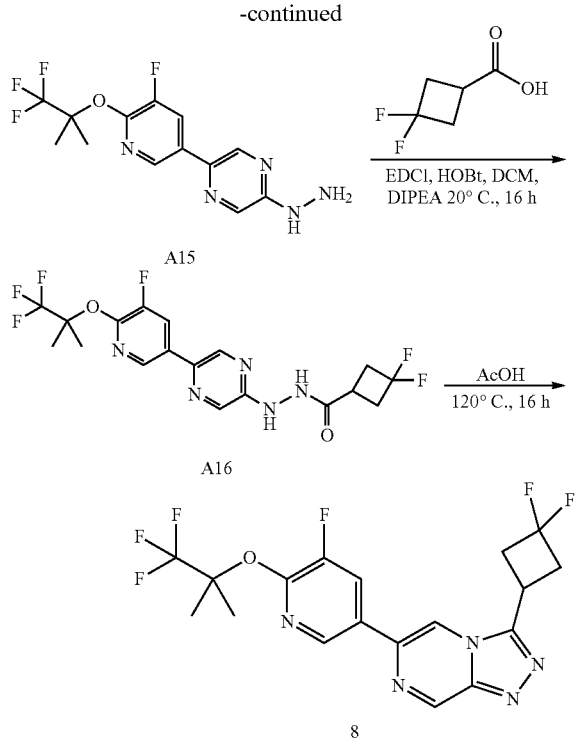

Synthesis of A14: A mixture of 2-bromo-5-chloro-pyrazine (2 g, 10.34 mmol), 3-fluoro-5-(4,4,5,5-tetramethyl-1,3,2-dioxaborolan-2-yl)-2-(2,2,2-trifluoro-1,1-dimethyl-ethoxy)pyridine (3.61 g, 10.34 mmol), $Cs_2CO_3$ (6.74 g, 20.68 mmol) and $Pd(dppf)Cl_2$ (1.13 g, 1.55 mmol) in 1,4-Dioxane (80 mL) and Water (8 mL) was stirred at 55° C. under $N_2$ for 5 hours. The mixture was cooled to room temperature and concentrated to give a residue. To the residue was added water (50 mL) and extracted with EtOAc (50 mL×2). The combined organic phase was washed with water (50 mL), brine (50 mL×2), dried over anhydrous $Na_2SO_4$, filtered and concentrated to give the crude product. The crude product was purified by flash chromatography column on silica gel (EtOAc in PE=0% to 5% to 10%) to give the product (2.3 g, 5.45 mmol) as a solid. $^1$H NMR (400 MHz, $CDCl_3$) $δ_H$=8.77 (d, 1H), 8.64 (d, 1H), 8.53 (d, 1H), 8.05 (dd, 1H), 1.88 (s, 6H). LCMS $R_t$=0.96 min in 1.5 min chromatography, MS ESI calcd. for $C_{13}H_{11}ClF_4N_3O$ $[M+H]^+$ 336.0, found 335.9.

Synthesis of A15: A solution of 2-chloro-5-[5-fluoro-6-(2,2,2-trifluoro-1,1-dimethyl-ethoxy)-3-pyridyl]pyrazine (2.3 g, 6.85 mmol) and hydrazine (2.20 g, 68.52 mmol) in MeCN (50 mL) was stirred at 90° C. under $N_2$ for 16 hours to give a solution. After cooling to room temperature, the solution was concentrated to give a residue. To the residue was added water (50 mL) and extracted with EtOAc (50 mL×2). The combined organic phase was washed with brine (50 mL×2), dried over anhydrous $Na_2SO_4$, filtered and concentrated to give the product (2.1 g, 6.34 mmol, 93% yield) as a solid. $^1$H NMR (400 MHz, $CDCl_3$) $δ_H$=8.42 (d, 2H), 8.29 (s, 1H), 7.94 (d, 1H), 6.12 (s, 1H), 3.92 (s, 2H), 1.84 (s, 6H). LCMS $R_t$=0.77 min in 1.5 min chromatography, MS ESI calcd. for $C_{13}H_{14}F_4N_5O$ $[M+H]^+$ 332.1, found 331.9.

Synthesis of A16: To a mixture of 3,3-difluorocyclobutanecarboxylic acid (129.42 mg, 0.95 mmol), HOBT (244.75 mg, 1.81 mmol) in DCM (20 mL) was added EDCI (260.41 mg, 1.36 mmol), DIPEA (0.47 mL, 2.72 mmol) and then [5-[5-fluoro-6-(2,2,2-trifluoro-1,1-dimethyl-ethoxy)-3-pyridyl]pyrazin-2-yl]hydrazine (300 mg, 0.91 mmol). The resulting mixture was stirred at 20° C. for 16 hours. The mixture was concentrated to give a residue. Water (50 mL) was added to the residue and extracted with EtOAc (50 mL×2). The combined organic phase was washed with brine (50 mL×2), dried over anhydrous $Na_2SO_4$, filtered and concentrated to give the product (350 mg, 0.63 mmol) as a solid. LCMS $R_t$=1.11 min in 2.0 min chromatography, MS ESI calcd. for $C_{18}H_{18}F_6N_5O_2[M+H]^+$ 450.1, found 450.1.

Synthesis of Compound 8: A solution of 3,3-difluoro-N'-[5-[5-fluoro-6-(2,2,2-trifluoro-1,1-dimethyl-ethoxy)-3-pyridyl]pyrazin-2-yl]cyclobutanecarbohydrazide (350 mg, 0.78 mmol) in acetic acid (20 mL, 0.78 mmol) was stirred at 120° C. for 16 hours to give a solution. The mixture was cooled to room temperature, and concentrated to give a residue. The residue was diluted with EtOAc (50 mL), then basified with sat. $NaHCO_3$ to pH=8-9, and extracted with EtOAc (50 mL×2). The combined organic phase was washed with water (50 mL) and brine (50 mL), dried over $Na_2SO_4$, filtered and concentrated to give the crude product. The crude product was purified by Prep-HPLC (Xbridge BEH C18, 250×50 mm, 10 μm), A=$H_2O$ (0.04% $NH_3·H_2O$+ 10 mM $NH_4HCO_3$) and B=$CH_3CN$; 50-70% B over 9 minutes) to give the product (150.32 mg, 348.5 μmol) as a solid. $^1$H NMR (400 MHz, $CDCl_3$) $δ_H$=9.44 (d, 1H), 8.49 (d, 1H), 8.06-7.97 (m, 2H), 3.86-3.70 (m, 1H), 3.43-3.19 (m, 4H), 1.88 (s, 6H). LCMS $R_t$=1.13 min in 2.0 min chromatography, MS ESI calcd. for $C_{18}H_{16}F_6N_5O$ $[M+H]^+$ 432.1, found 432.0.

Example 9: 3-(difluoromethyl)-6-[5-fluoro-6-[1-(trifluoromethyl)cyclobutoxy]-3-pyridyl]-[1,2,4]triazolo[4,3-a]pyrazine

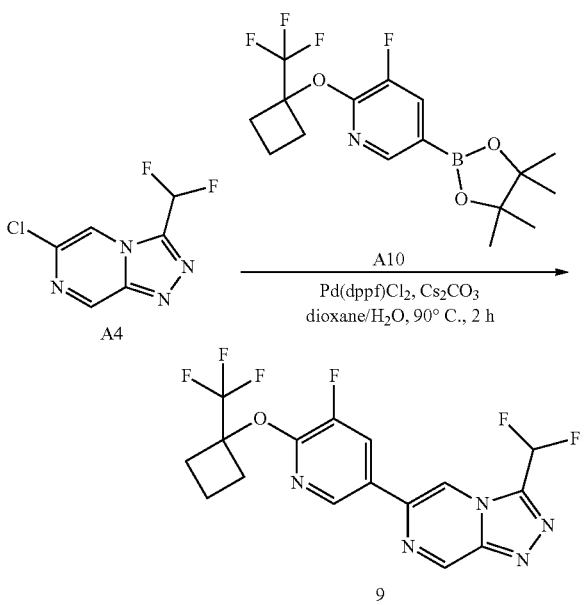

A mixture of 3-fluoro-5-(4,4,5,5-tetramethyl-1,3,2-dioxaborolan-2-yl)-2-[1-(trifluoromethyl)cyclobutoxy]pyridine (211.85 mg, 0.59 mmol), $Pd(dppf)Cl_2$ (53.65 mg, 0.07 mmol), $Cs_2CO_3$ (318.54 mg, 0.98 mmol), and 6-chloro-3-(difluoromethyl)-[1,2,4]triazolo[4,3-a]pyrazine (100 mg, 0.49 mmol) in 1,4-Dioxane (2 mL) and Water (0.20 mL) was stirred under N$_2$ at 90° C. for 2 hours. The mixture was cooled to room temperature, diluted with EtOAc (10 mL), filtered through silica gel, eluted with EtOAc (10 mL) and concentrated to give the crude product. The crude product was purified by Prep-HPLC (Boston Prime C18 (150 mm×30 mm, 5 μm), A=water (0.05% NH$_4$OH) and B=CH$_3$CN; 52-82% B over 9 minutes) to give the product (6.75 mg, 16.7 μmol) as a solid. $^1$H NMR (400 MHz, MeOD-d$_4$) δ$_H$=9.55 (d, 1H), 9.02 (d, 1H), 8.71 (d, 1H), 8.31 (dd, 1H), 7.60 (t, 1H), 3.05-2.95 (m, 2H), 2.78-2.70 (m, 2H), 2.17-1.93 (m, 2H). LCMS R$_t$=1.32 min in 2.0 min chromatography, MS ESI calcd. for C$_{16}$H$_{12}$F$_6$N$_5$O [M+H]$^+$ 404.1, found 404.0.

Example 10: 3-(2,2-difluorocyclopropyl)-6-[5-fluoro-6-(2,2,2-trifluoro-1,1-dimethyl-ethoxy)-3-pyridyl]-[1,2,4]triazolo[4,3-a]pyrazine

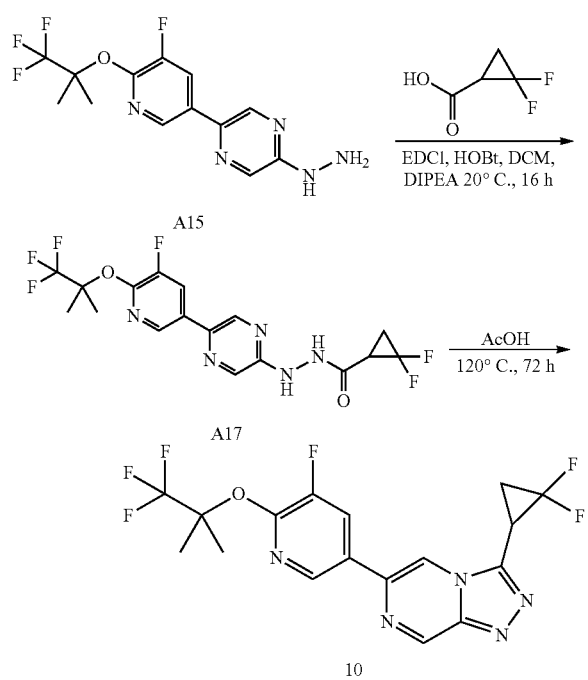

Synthesis of A17: To a mixture of 2,2-difluorocyclopropanecarboxylic acid (193.46 mg, 1.58 mmol), HOBt (407.91 mg, 3.02 mmol) in DCM (20 mL) was added EDCI (434.01 mg, 2.26 mmol), DIPEA (0.79 mL, 4.53 mmol) and then [5-[5-fluoro-6-(2,2,2-trifluoro-1,1-dimethyl-ethoxy)-3-pyridyl]pyrazin-2-yl]hydrazine (500 mg, 1.51 mmol). The resulting mixture was stirred at 20° C. for 16 hours to give a solution. The solution was concentrated to give a residue. To the residue was added water (50 mL) and extracted with EtOAc (50 mL×2). The combined organic phase was washed with brine (50 mL×2), dried over anhydrous Na$_2$SO$_4$, filtered and concentrated to give the crude product (500 mg, 0.80 mmol) as a solid. LCMS R$_t$=1.06 min in 1.5 min chromatography, MS ESI calcd. for C$_{17}$H$_{16}$F$_6$N$_5$O$_2$ [M+H]$^+$ 436.1, found 436.0.

Synthesis of Compound 10: A solution of 2,2-difluoro-N'-[5-[5-fluoro-6-(2,2,2-trifluoro-1,1-dimethyl-ethoxy)-3-pyridyl]pyrazin-2-yl]cyclopropanecarbohydrazide (500 mg, 1.15 mmol) in acetic acid (20 mL, 1.15 mmol) was stirred at 120° C. for 72 hours to give a solution. The mixture was cooled to room temperature, and concentrated to give a residue. The residue was diluted with EtOAc (50 mL), then basified with sat. NaHCO$_3$ to pH=8-9, and extracted with EtOAc (50 mL×2). The combined organic phase was washed with water (50 mL) and brine (50 mL), dried over Na$_2$SO$_4$, filtered and concentrated to give the crude product. The crude product was purified by Prep-HPLC (Boston Prime C18 (150 mm×30 mm, 5 μm) A=H$_2$O (0.05% NH$_4$OH) and B=CH$_3$CN; 55-85% B over 8 minutes) to give the product (180 mg, 0.43 mmol, 38% yield). Part of the product (30 mg) was purified by Prep-TLC (silica gel, PE:EtOAc=1:1) to give the product (24.62 mg, 0.06 mmol) as a solid. $^1$H NMR (400 MHz, CDCl$_3$) δ$_H$=9.44 (d, 1H), 8.52 (d, 1H), 8.24 (d, 1H), 8.03 (dd, 1H), 3.06-2.96 (m, 1H), 2.72-2.62 (m, 1H), 2.37-2.25 (m, 1H), 1.89 (s, 6H). LCMS R$_t$=1.33 min in 2.0 min chromatography, MS ESI calcd. for C$_{17}$H$_{14}$F$_6$N$_5$O [M+H]$^+$ 418.1, found 418.0.

Example 11: 3-(2,2-difluorocyclopropyl)-6-[5-fluoro-6-(2,2,2-trifluoro-1,1-dimethyl-ethoxy)-3-pyridyl]-[1,2,4]triazolo[4,3-b]pyridazine

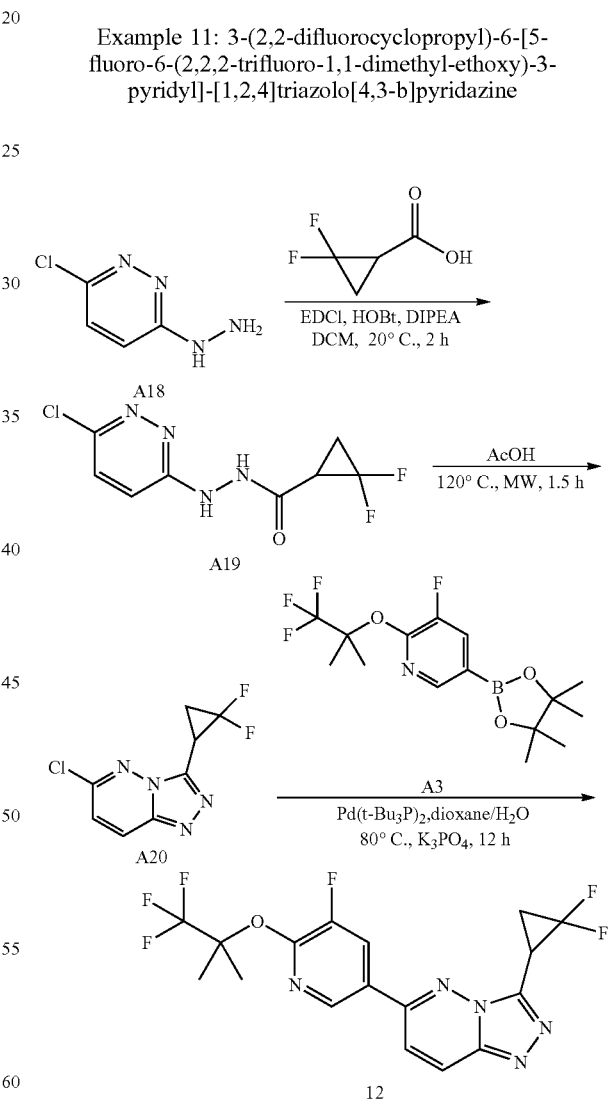

Synthesis of A19: To a mixture of 2,2-difluorocyclopropanecarboxylic acid (422.21 mg, 3.46 mmol), HOBt (934.77 mg, 6.92 mmol) and EDCI (994.57 mg, 5.19 mmol) in DCM (30 mL) was added DIPEA (1.81 mL, 10.38 mmol) and (6-chloropyridazin-3-yl)hydrazine (500 mg, 3.46 mmol) and the mixture was stirred at 20° C. for 2 hours to give a mixture. The mixture was diluted with sat. NH₄Cl (80 mL) and extracted with DCM (80 mL×2). The combined organic phase was washed with brine (40 mL), dried over Na₂SO₄, and filtered. The filtrate was concentrated to give the crude product (1400 mg, 2.64 mmol) as an oil. The crude product was used directly in next step without any purification. LCMS $R_t$=0.44 min in 1.5 min chromatography, MS ESI calcd. for $C_8H_8ClF_2N_4O$ [M+H]⁺ 249.0, Found 248.8.

Synthesis of A20: A mixture of N'-(6-chloropyridazin-3-yl)-2,2-difluoro-cyclopropanecarbohydrazide (1400 mg, 5.63 mmol) in Acetic acid (10 mL) was stirred at 120° C. for 1.5 hours under microwave to give a mixture. The mixture was cooled to room temperature, and concentrated to give the crude product. The crude product was diluted with EtOAc (10 mL), then basified with sat. NaHCO₃ to pH=9, and extracted with EtOAc (20 mL×2). The combined organic phase was washed with water (20 mL) and brine (15 mL), dried over Na₂SO₄, filtered and concentrated to give the product (260 mg, 0.80 mmol) as a solid. LCMS $R_t$=0.69 min in 1.5 min chromatography, MS ESI calcd. for $C_8H_6ClF_2N_4$[M+H]⁺ 231.0, found 230.9.

Synthesis of Compound 12: A mixture of 6-chloro-3-(2,2-difluorocyclopropyl)-[1,2,4]triazolo[4,3-b]pyridazine (270 mg, 1.17 mmol), 3-fluoro-5-(4,4,5,5-tetramethyl-1,3,2-dioxaborolan-2-yl)-2-(2,2,2-trifluoro-1,1-dimethyl-ethoxy)pyridine (490.54 mg, 1.41 mmol), Pd(t-Bu₃P)₂ (89.76 mg, 0.18 mmol), and K₃PO₄ (745.72 mg, 3.51 mmol) in 1,4-Dioxane (4 mL) and Water (0.50 mL) was stirred at 80° C. for 12 hours. The mixture was cooled to room temperature, diluted with EtOAc (20 mL), filtered through silica gel, eluted with EtOAc (20 mL) and concentrated to give the crude product. The crude product was purified by Prep-HPLC (Boston Prime (C18 150 mm×30 mm, 5 μm), A=water (0.05% NH₄OH) and B=CH₃CN; 55-85% B over 9 minutes) to give the product (171 mg, 35% yield) as a solid. ¹H NMR (400 MHz, CDCl₃) $δ_H$=8.54 (d, 1H), 8.22 (d, 1H), 8.08 (dd, 1H), 7.56 (d, 1H), 3.36-3.26 (m, 1H), 2.69-2.60 (m, 1H), 2.24-2.12 (m, 1H), 1.91 (s, 6H). LCMS $R_t$=1.31 min in 2.0 min chromatography, MS ESI calcd. for $C_{17}H_{14}F_6N_5O$ [M+H]⁺ 418.1, found 418.0.

Example 12: 3-[(1R)-2,2-difluorocyclopropyl]-6-[5-fluoro-6-(2,2,2-trifluoro-1,1-dimethyl-ethoxy)-3-pyridyl]-[1,2,4]triazolo[4,3-b]pyridazine & 3-[(1S)-2,2-difluorocyclopropyl]-6-[5-fluoro-6-(2,2,2-trifluoro-1,1-dimethyl-ethoxy)-3-pyridyl]-[1,2,4]triazolo[4,3-b]pyridazine

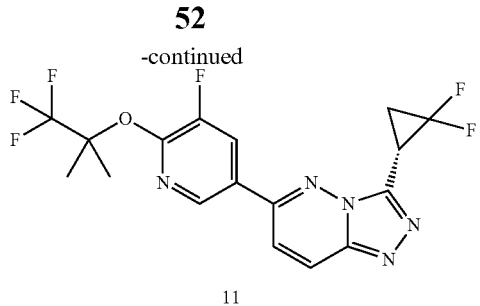

11

Compound 12 was analyzed by SFC to show two peaks (Peak 1: Rt=1.51 min, Peak 2: Rt=1.66 min). Method: Column: Chiralcel OJ-3 100×4.6 mm I.D., 3 μm Mobile phase: A: CO₂ B: ethanol (0.05% DEA) Gradient: from 5% to 40% of B in 4.5 min and hold 40% for 0.5 min, then 5% of B for 1 min Flow rate: 2.8 mL/min Column temperature: 40° C. Stereochemistry was randomly assigned.

Compound 12 was separated by SFC (DAICEL CHIRALCEL OD-H (250 mm×30 mm, 5 μm); A=CO₂ and B=EtOH (0.1% NH₃·H₂O); 35° C.; 60 mL/min; 30% B; 7 min run; 19 injections, Rt of Peak 1 (Isomer 1)=4.00 min, Rt of Peak 2 (Isomer 2)=4.60 min).

Isomer 1 (39.98 mg, 95.8 μmol) (Peak 1, Rt=1.51 min in SFC) ¹H NMR (400 MHz, CDCl₃) $δ_H$=8.54 (d, 1H), 8.22 (d, 1H), 8.08 (dd, 1H), 7.55 (d, 1H), 3.38-3.26 (m, 1H), 2.70-2.61 (m, 1H), 2.25-2.13 (m, 1H), 1.91 (s, 6H). LCMS $R_t$=1.32 min in 2.0 min chromatography, MS ESI calcd. for $C_{17}H_{14}F_6N_5O$ [M+H]⁺ 418.1, found 418.0.

Isomer 2 (38 mg, 91.1 μmol) (Peak 2, Rt=1.66 min in SFC). ¹H NMR (400 MHz, CDCl₃) $δ_H$=8.54 (d, 1H), 8.22 (d, 1H), 8.08 (dd, 1H), 7.55 (d, 1H), 3.38-3.26 (m, 1H), 2.70-2.61 (m, 1H), 2.25-2.13 (m, 1H), 1.91 (s, 6H). LCMS $R_t$=1.30 min in 2.0 min chromatography, MS ESI calcd. for $C_{17}H_{14}F_6N_5O$ [M+H]⁺ 418.1, found 418.0.

Example 13: 3-[(1R)-2,2-difluorocyclopropyl]-6-[5-fluoro-6-(2,2,2-trifluoro-1,1-dimethyl-ethoxy)-3-pyridyl]-[1,2,4]triazolo[4,3-a]pyrazine & 3-[(1S)-2,2-difluorocyclopropyl]-6-[5-fluoro-6-(2,2,2-trifluoro-1,1-dimethyl-ethoxy)-3-pyridyl]-[1,2,4]triazolo[4,3-a]pyrazine

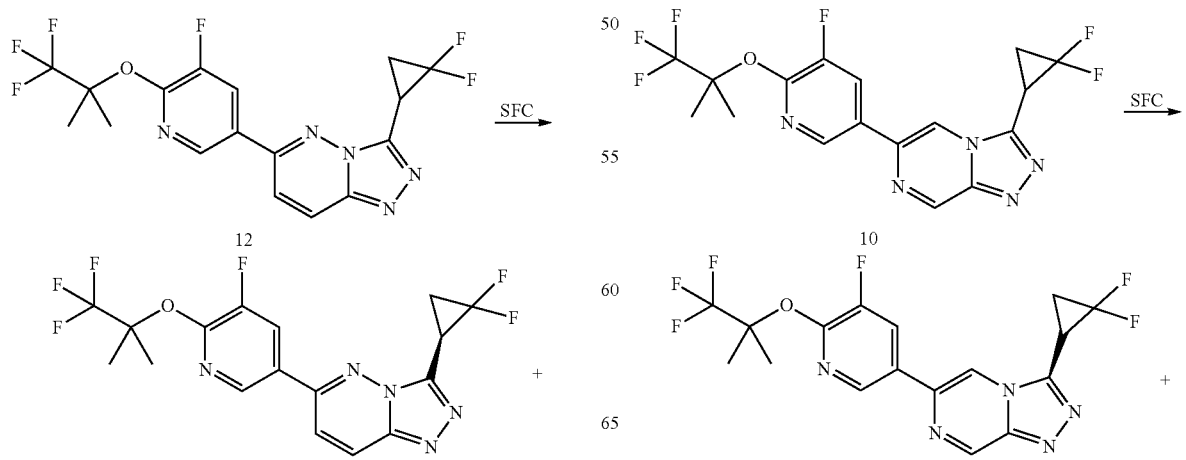

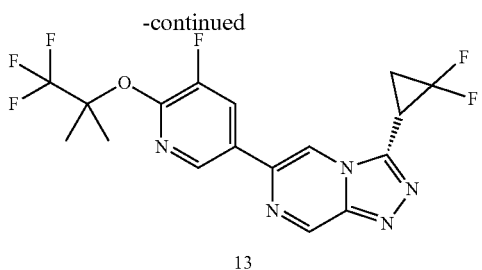

13

Compound 10 analyzed by SFC showed two peaks (Peak 1, Isomer 1: Rt=1.65 min, Peak 2, Isomer 2: Rt=1.93 min). Method: Column: Chiralcel OJ-3 100×4.6 mm I.D., 3 μm Mobile phase: A: CO$_2$ B: ethanol (0.05% DEA) Gradient: from 5% to 40% of B in 4.5 min and hold 40% for 0.5 min, then 5% of B for 1 min Flow rate: 2.8 mL/min Column temperature: 40° C. Stereochemistry was randomly assigned.

Compound 10 was separated by SFC (DAICEL CHIRALCEL OD-H (250 mm×30 mm, 5 μm); A=CO$_2$ and B=0.1% NH$_3$·H$_2$O-EtOH; 38° C.; 60 mL/min; 25% B; 10 min run; 20 injections, Rt of peak 1, Isomer 1=7.6 min, Rt of peak 2=8.5 min) (46.88 mg, 0.11 mmol) (Peak 1, Isomer 1, Rt=1.65 min in SFC) as a solid and (40.22 mg, 0.10 mmol) (Peak 2, Isomer 2: Rt=1.93 min in SFC) as a solid.

Isomer 1: $^1$H NMR (400 MHz, CDCl$_3$) δ$_H$=9.44 (d, 1H), 8.52 (d, 1H), 8.24 (d, 1H), 8.03 (dd, 1H), 3.06-2.97 (m, 1H), 2.72-2.62 (m, 1H), 2.36-2.25 (m, 1H), 1.89 (s, 6H). LCMS R$_t$=1.3 min in 2.0 min chromatography. MS ESI calcd. for C$_{17}$H$_{14}$F$_6$N$_5$O [M+H]$^+$ 418.1, found 418.0.

Isomer 2: $^1$H NMR (400 MHz, CDCl$_3$) δ$_H$=9.44 (d, 1H), 8.52 (d, 1H), 8.24 (d, 1H), 8.03 (dd, 1H), 3.04-2.97 (m, 1H), 2.72-2.62 (m, 1H), 2.36-2.26 (m, 1H), 1.89 (s, 6H). LCMS R$_t$=1.3 min in 2.0 min chromatography. MS ESI calcd. for C$_{17}$H$_{14}$F$_6$N$_5$O [M+H]$^+$ 418.1, found 418.0.

Example 14: 3-(3,3-difluorocyclobutyl)-6-[5-fluoro-6-(2,2,2-trifluoro-1,1-dimethyl-ethoxy)-3-pyridyl]-[1,2,4]triazolo[4,3-b]pyridazine

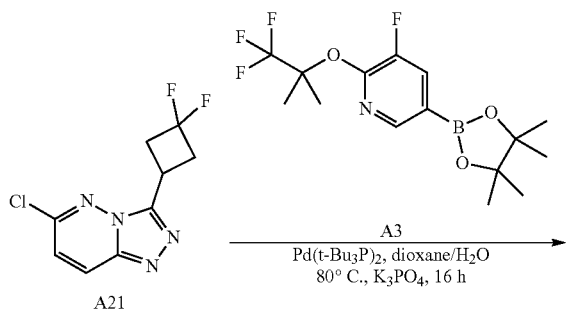

A mixture of 6-chloro-3-(3,3-difluorocyclobutyl)-[1,2,4]triazolo[4,3-b]pyridazine (130 mg, 0.53 mmol), 3-fluoro-5-(4,4,5,5-tetramethyl-1,3,2-dioxaborolan-2-yl)-2-(2,2,2-trifluoro-1,1-dimethyl-ethoxy)pyridine (222.64 mg, 0.64 mmol), Pd(t-Bu$_3$P)$_2$ (40.74 mg, 0.08 mmol), and K$_3$PO$_4$ (338.46 mg, 1.59 mmol) in 1,4-Dioxane (2 mL) and Water (0.20 mL) was stirred at 80° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Boston Prime C18 150×30 mm 5 μm, A=water (0.05% NH$_3$·H$_2$O) and B=CH$_3$CN; 58-88% B over 8 minutes) to give the product (169.38 mg, 0.40 mmol) as a solid. $^1$H NMR (400 MHz, DMSO-d$_6$) δ$_H$=8.84 (d, 1H), 8.57-8.46 (m, 2H), 8.03 (d, 1H), 4.15-4.04 (m, 1H), 3.31-3.15 (m, 4H), 1.85 (s, 6H). LCMS R$_t$=1.36 min in 2.0 min chromatography, MS ESI calcd. for C$_{18}$H$_{16}$F$_6$N$_5$O [M+H]$^+$ 432.1, found 432.0.

Example 15: 3-(difluoromethyl)-6-[5-fluoro-6-[(1S)-2,2,2-trifluoro-1-methyl-ethoxy]-3-pyridyl]-[1,2,4]triazolo[4,3-b]pyridazine

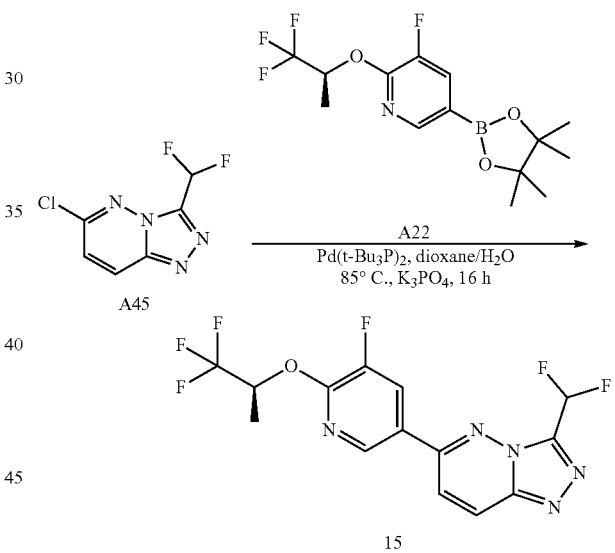

A mixture of 6-chloro-3-(difluoromethyl)-[1,2,4]triazolo[4,3-b]pyridazine (100 mg, 0.49 mmol), 3-fluoro-5-(4,4,5,5-tetramethyl-1,3,2-dioxaborolan-2-yl)-2-[(1S)-2,2,2-trifluoro-1-methyl-ethoxy]pyridine (196.58 mg, 0.59 mmol), Pd(t-Bu$_3$P)$_2$ (37.47 mg, 0.07 mmol), and K$_3$PO$_4$ (207.57 mg, 0.98 mmol) in 1,4-Dioxane (4 mL) and Water (0.40 mL) was stirred at 85° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Waters Xbridge (150 mm×25 mm, 5 μm) A=H$_2$O (10 mM NH$_4$HCO$_3$) and B=CH$_3$CN; 40-70% B over 7 minutes) to give the product (81.42 mg, 0.22 mmol) as a solid. $^1$H NMR (400 MHz, DMSO-d$_6$) δ$_H$=8.85 (d, 1H), 8.67 (d, 1H), 8.55 (dd, 1H), 8.20 (d, 1H), 7.83 (t, 1H), 6.13-5.97 (m, 1H), 1.56 (d, 3H). LCMS R$_t$=1.24 min in 2 min chromatography, MS ESI calcd. for C$_{14}$H$_{10}$F$_6$N$_5$O [M+H]$^+$ 378.1, found 378.0.

Example 16: 3-[(1R)-2,2-difluorocyclopropyl]-6-[5-fluoro-6-[(1R)-2,2,2-trifluoro-1-methyl-ethoxy]-3-pyridyl]-[1,2,4]triazolo[4,3-a]pyrazine & 3-[(1S)-2,2-difluorocyclopropyl]-6-[5-fluoro-6-[(1R)-2,2,2-trifluoro-1-methyl-ethoxy]-3-pyridyl]-[1,2,4]triazolo[4,3-a]pyrazine
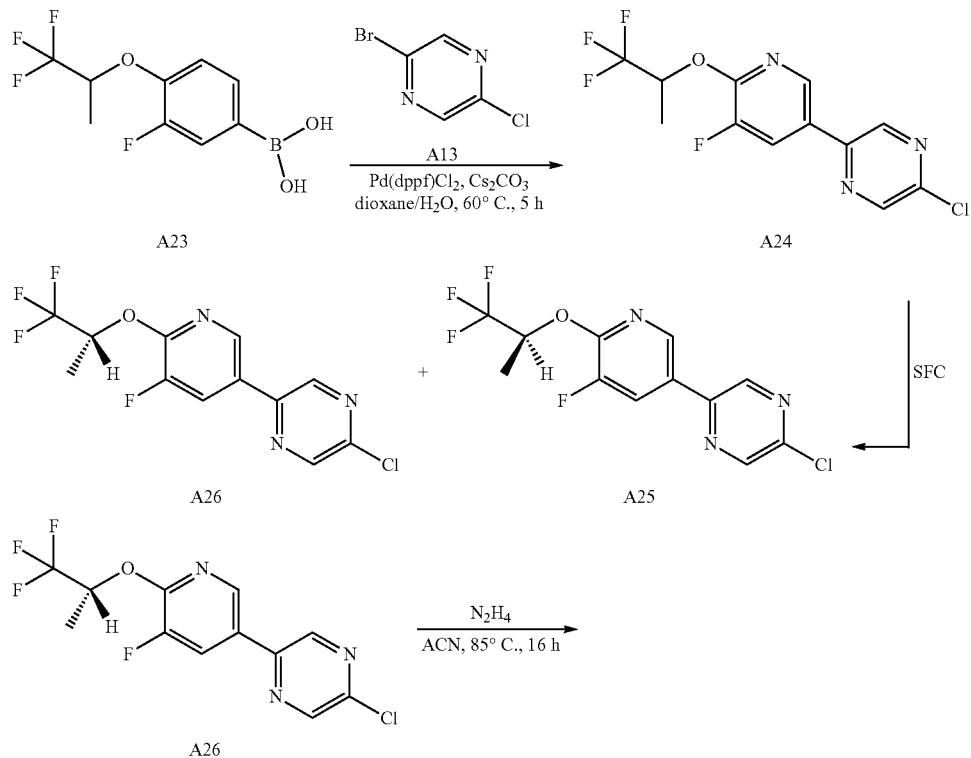
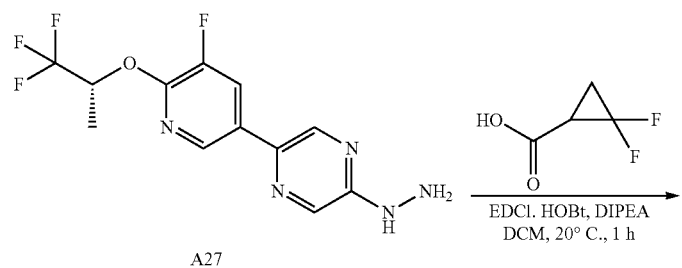
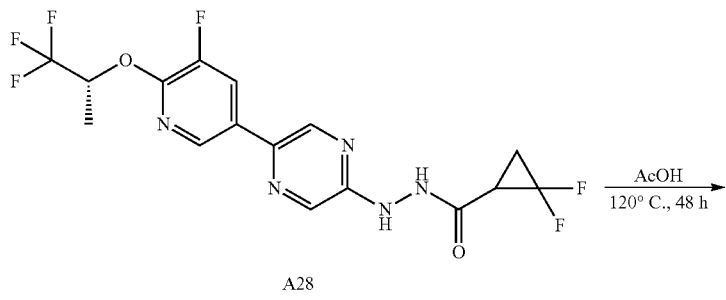

-continued

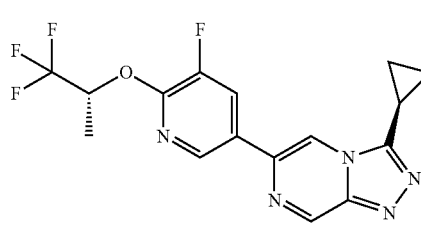 + 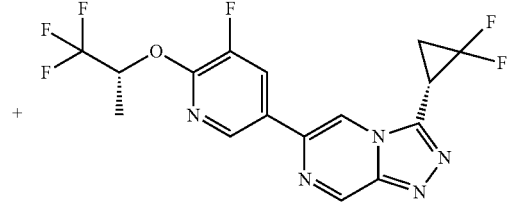

16

Synthesis of A24: A mixture of 2-bromo-5-chloro-pyrazine (229.4 mg, 1.19 mmol), [5-fluoro-6-(2,2,2-trifluoro-1-methyl-ethoxy)-3-pyridyl]boronic acid (300 mg, 1.19 mmol), Pd(dppf)Cl$_2$ (130.16 mg, 0.18 mmol) and Cs$_2$CO$_3$ (772.77 mg, 2.37 mmol) in 1,4-dioxane (10 mL) and water (1 mL) was stirred at 60° C. for 5 hours under N$_2$. After cooling to room temperature, the mixture was diluted with H$_2$O (30 mL), and the mixture was extracted with EtOAc (50 mL×2). The combined organic phase was washed with water (20 mL×2) and brine (20 mL), dried over Na$_2$SO$_4$, filtered and concentrated to give the crude product. The crude product was purified by flash chromatography on silica gel (EtOAc in PE=0% to 1% to 3%) to give the product (210 mg, 0.64 mmol) as a solid. The product was analyzed by SFC to show two peaks (Peak 1: Rt=2.02 min, Peak 2: Rt=2.28 min).

Synthesis of A25 and A26: The 2-chloro-5-[5-fluoro-6-(2,2,2-trifluoro-1-methyl-ethoxy)-3-pyridyl]pyrazine (150 mg, 0.46 mmol) was purified by SFC (DAICEL CHIRALPAK AD-H (250 mm×30 mm, 5 μm); A=CO$_2$ and B=EtOH (0.1% NH$_3$H$_2$O); 38° C.; 50 mL/min; 15% B; 8.8 min run; 15 injections, Rt of Peak 1=6.27 min, Rt of Peak 2=7.28 min) to give 2-chloro-5-[5-fluoro-6-[(1R)-2,2,2-trifluoro-1-methyl-ethoxy]-3-pyridyl]pyrazine (70 mg, 0.21 mmol) (Peak 1, Isomer 1, Rt=2.02 min in SFC) as a solid and 2-chloro-5-[5-fluoro-6-[(1S)-2,2,2-trifluoro-1-methyl-ethoxy]-3-pyridyl]pyrazine (70 mg, 0.22 mmol) (Peak 2, Isomer 2, Rt=2.28 min in SFC) as a solid. Note: the stereochemistry is randomly assigned. LCMS R$_t$=1.27 min in 2.0 min chromatography, MS ESI calcd. for C$_{12}$H$_9$ClF$_4$N$_3$O [M+H]$^+$ 322.0, found 321.9. LCMS R$_t$=1.25 min in 2.0 min chromatography, MS ESI calcd. for C$_{12}$H$_9$ClF$_4$N$_3$O [M+H]$^+$ 322.0, found 321.9.

Synthesis of A27: A mixture of A26 (70 mg, 0.22 mmol) and hydrazine (139.5 mg, 4.35 mmol) in MeCN (5 mL) was stirred at 85° C. for 16 hours. After cooling to room temperature, the mixture was concentrated to give the crude product (65 mg, 0.20 mmol) as a solid, which was used directly without any further purification. LCMS R$_t$=0.72 min in 1.5 min chromatography, MS ESI calcd. for C$_{12}$H$_{12}$F$_4$N$_5$O [M+H]$^+$ 318.1, found 317.9. Stereochemistry is randomly assigned below.

Synthesis of A28: To a mixture of 2,2-difluorocyclopropanecarboxylic acid (202.01 mg, 1.65 mmol), HOBt (298.17 mg, 2.21 mmol) and EDCI (317.24 mg, 1.65 mmol) in DCM (20 mL) was added DIPEA (0.58 mL, 3.31 mmol) and [5-[5-fluoro-6-[(1R)-2,2,2-trifluoro-1-methyl-ethoxy]-3-pyridyl]pyrazin-2-yl]hydrazine (350 mg, 1.1 mmol) and the mixture was stirred at 20° C. for 1 hour to give a mixture. The mixture was diluted with sat. NH$_4$Cl (80 mL) and extracted with DCM (80 mL×2). The combined organic phase was washed with brine (40 mL), dried over Na$_2$SO$_4$, and filtered. The filtrate was concentrated to give the crude product (600 mg, 0.67 mmol) as an oil. The crude product was used directly in next step without any purification. LCMS R$_t$=0.85 min in 1.5 min chromatography, MS ESI calcd. for C$_{16}$H$_{14}$F$_6$N$_5$O$_2$ [M+H]$^+$ 422.1, found 422.1.

Synthesis of Compound 16: A mixture of 2,2-difluoro-N'-[5-[5-fluoro-6-[(1R)-2,2,2-trifluoro-1-methyl-ethoxy]-3-pyridyl]pyrazin-2-yl]cyclopropanecarbohydrazide (600 mg, 1.42 mmol) in Acetic acid (20 mL) was stirred at 120° C. for 48 hours to give a mixture. The mixture was cooled to room temperature, and concentrated to give the crude product. The crude product was diluted with EtOAc (10 mL), then basified with sat. NaHCO$_3$ to pH=8-9, and extracted with EtOAc (20 mL×2). The combined organic phase was washed with water (20 mL) and brine (15 mL), dried over Na$_2$SO$_4$, filtered and concentrated to give the impure product. The impure product was purified by Prep-HPLC (Boston Prime C18 (150 mm×30 mm, 5 μm) A=H$_2$O (0.05% NH$_4$OH) and B=CH$_3$CN; 50-80% B over 8 minutes) to give the product (120 mg, 0.30 mmol) as a solid. Stereochemistry was randomly assigned.

Compound 16 was analyzed by SFC to give the two peaks (Isomer 1, Peak 1=2.31 min, Isomer 2, Peak 2=2.63 min). Method: Column: Chiralcel OJ-3 150×4.6 mm I.D., 3 μm, Mobile phase: A: CO$_2$ B: ethanol (0.05% DEA), Gradient: from 5% to 40% of B in 5 min and hold 40% for 2.5 min, then 5% of B for 2.5 min, Flow rate: 2.5 mL/min, Column temp.: 35° C.

Compound 16 was separated by SFC (DAICEL CHIRALCEL OJ-H (250 mm×30 mm, 5 μm); A=CO$_2$ and B=EtOH (0.1% NH$_3$H$_2$O); 35° C.; 50 mL/min; 20% B; 7 min run; 8 injections, Rt of Isomer 1, peak 1=4.17 min, Rt of peak 2=5.08 min) to give the product (Isomer 1, Peak 1, Rt=2.31 min in SFC as a solid and (30.76 mg, 76.30 μmol) (Isomer 2, Peak 2, Rt=2.63 min in SFC as a solid.

Isomer 1: (27.70 mg, 68.6 μmol) (Peak 1, Rt=2.31 min in SFC). $^1$H NMR (400 MHz, CD$_3$CN) $\delta_H$=9.44 (d, 1H), 8.52 (d, 1H), 8.25 (d, 1H), 8.06 (dd, 1H), 5.98-5.85 (m, 1H), 3.10-2.96 (m, 1H), 2.75-2.58 (m, 1H), 2.39-2.24 (m, 1H), 1.60 (d, 3H). LCMS R$_t$=1.08 min in 2.0 min chromatography, MS ESI calcd. for C$_{16}$H$_{12}$F$_6$N$_5$O [M+H]$^+$ 404.1, found 404.0.

Isomer 2: (30.76 mg, 76.30 μmol) (Peak 2, Rt=2.63 min in SFC). $^1$H NMR (400 MHz, CD$_3$CN) $\delta_H$=9.44 (d, 1H), 8.51 (d, 1H), 8.26 (d, 1H), 8.07 (dd, 1H), 6.03-5.73 (m, 1H), 3.12-2.96 (m, 1H), 2.76-2.53 (m, 1H), 2.42-2.19 (m, 1H), 1.60 (d, 3H). LCMS R$_t$=1.09 min in 2.0 min chromatography, MS ESI calcd. for C$_{16}$H$_{12}$F$_6$N$_5$O [M+H]$^+$ 404.1, found 404.0.

Example 17: 3-(difluoromethyl)-6-[5-fluoro-6-[(1R)-2,2,2-trifluoro-1-methyl-ethoxy]-3-pyridyl]-[1,2,4]triazolo[4,3-b]pyridazine

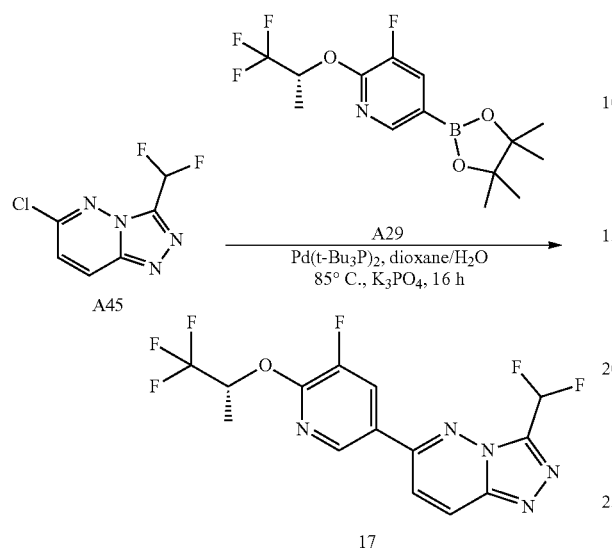

17

A mixture of 3-fluoro-5-(4,4,5,5-tetramethyl-1,3,2-dioxaborolan-2-yl)-2-[(1R)-2,2,2-trifluoro-1-methyl-ethoxy]pyridine (294.87 mg, 0.88 mmol), 6-chloro-3-(difluoromethyl)-[1,2,4]triazolo[4,3-b]pyridazine (150 mg, 0.73 mmol), Pd(t-Bu₃P)₂ (56.21 mg, 0.11 mmol), and K₃PO₄ (311.35 mg, 1.47 mmol) in 1,4-Dioxane (4 mL) and Water (0.40 mL) was stirred at 85° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Waters Xbridge (150 mm×25 mm, 5 μm) A=H₂O (10 mM NH₄HCO₃) and B=CH₃CN; 45-65% B over 7 minutes) to give the product (66.41 mg, 0.18 mmol, 24% yield) as a solid. ¹H NMR (400 MHz, DMSO-d₆) $\delta_H$=8.86 (s, 1H), 8.68 (d, 1H), 8.56 (d, 1H), 8.21 (d, 1H), 7.84 (t, m, 1H), 6.20-5.87 (s, 1H), 1.65-1.35 (s, 3H). LCMS $R_t$=1.23 min in 2 min chromatography, MS ESI calcd. for $C_{14}H_{10}F_6N_5O$ [M+H]⁺ 378.1, found 378.0.

Example 18: 3-[(1R)-2,2-difluorocyclopropyl]-6-[5-fluoro-6-[(1S)-2,2,2-trifluoro-1-methyl-ethoxy]-3-pyridyl]-[1,2,4]triazolo[4,3-a]pyrazine & 3-[(1S)-2,2-difluorocyclopropyl]-6-[5-fluoro-6-[(1S)-2,2,2-trifluoro-1-methyl-ethoxy]-3-pyridyl]-[1,2,4]triazolo[4,3-a]pyrazine

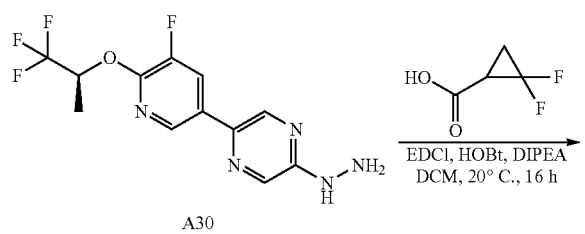

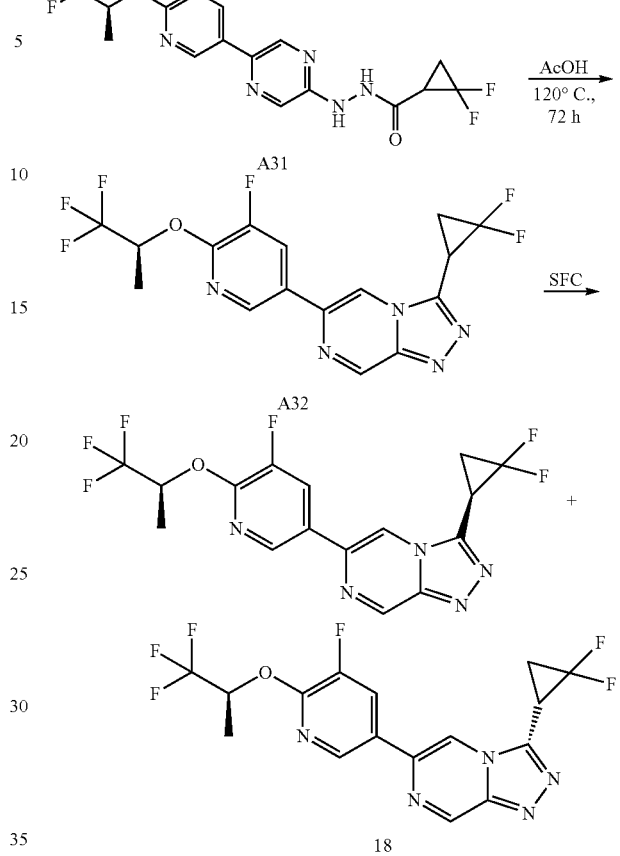

Synthesis of A31: To a mixture of 2,2-difluorocyclopropanecarboxylic acid (98.11 mg, 0.80 mmol), HOBt (206.86 mg, 1.53 mmol) in DCM (20 mL) was added EDCI (220.09 mg, 1.15 mmol), DIPEA (0.4 mL, 2.3 mmol) and then [5-[5-fluoro-6-[(1S)-2,2,2-trifluoro-1-methyl-ethoxy]-3-pyridyl]pyrazin-2-yl]hydrazine (300 mg, 0.77 mmol). The resulting mixture was stirred at 20° C. for 16 hours to give a solution. The solution was concentrated to give a residue. To the residue was added water (20 mL) and extracted with EtOAc (20 mL×2). The combined organic phase was washed with brine (20 mL×2), dried over anhydrous Na₂SO₄, filtered and concentrated to give the crude product (320 mg, 0.60 mmol) as a solid. LCMS $R_t$=0.82 min in 1.5 min chromatography, MS ESI calcd. for $C_{16}H_{14}F_6N_5O_2$ [M+H]⁺ 422.1, found 422.0.

Synthesis of A32: A solution of 2,2-difluoro-N'-[5-[5-fluoro-6-[(1S)-2,2,2-trifluoro-1-methyl-ethoxy]-3-pyridyl]pyrazin-2-yl]cyclopropanecarbohydrazide (300 mg, 0.71 mmol) in acetic acid (20 mL, 0.71 mmol) was stirred at 120° C. for 72 hours to give a solution. The mixture was cooled to room temperature, and concentrated to give a residue. The residue was diluted with EtOAc (20 mL), then basified with sat. NaHCO₃ to pH=8-9, and extracted with EtOAc (20 mL×2). The combined organic phase was washed with water (20 mL) and brine (20 mL), dried over Na₂SO₄, filtered and concentrated to give the crude product. The crude product was purified by Prep-HPLC (Boston Prime C18 (150 mm×30 mm, 5 μm) A=H₂O (0.05% NH₄OH) and B=CH₃CN; 55-85% B over 8 minutes) to give the product (130 mg, 276.5 μmol) as a solid. LCMS $R_t$=0.85 min in 1.5 min chromatography, MS ESI calcd. for $C_{16}H_{12}F_6N_5O$ [M+H]$^+$ 404.1, found 404.0.

Synthesis of Compound 18: Stereochemistry is randomly assigned. A32 analyzed by SFC showed two peaks (Peak 1, Isomer 1: Rt=1.57 min, Peak 2, Isomer 2: Rt=1.79 min). Method: Column: Chiralpak Chiralcel OJ-3 100×4.6 mm I.D., 3 um Mobile phase: ethanol (0.05% DEA) in $CO_2$, Gradient: from 5% to 40% of B in 4.5 min and hold 40% for 2.5 min, then 5% of B for 1 min, Flow rate: 2.8 mL/min Column temperature: 40° C. A32 was separated by SFC (DAICEL CHIRALCEL OJ-H (250 mm×30 mm, 5 μm); A=$CO_2$ and B=0.1% $NH_3 \cdot H_2O$-EtOH; 35° C.; 50 mL/min; 15% B; 8 min run; 12 injections, Rt of peak 1, Isomer 1=5.07 min, Rt of peak 2=6.30 min) (42.69 mg, 102.2 μmol) (Peak 1, Rt=1.57 min in SFC) as a solid and (37.8 mg, 93.7 μmol) (Peak 2, Isomer 2, Rt=1.79 min in SFC) as a solid.

Isomer 1: (42.69 mg, 102.2 μmol) (Peak 1, Rt=1.57 min in SFC). $^1$H NMR (400 MHz, CDCl$_3$) $\delta_H$=9.44 (d, 1H), 8.52 (d, 1H), 8.26 (d, 1H), 8.07 (dd, 1H), 5.93-5.87 (m, 1H), 3.09-2.96 (m, 1H), 2.72-2.59 (m, 1H), 2.36-2.25 (m, 1H), 1.60 (d, 3H). LCMS $R_t$=1.20 min in 2.0 min chromatography, MS ESI calcd. for $C_{16}H_{12}F_6N_5O$ [M+H]$^+$ 404.1, found 403.9.

Isomer 2: (37.8 mg, 93.7 μmol) (Peak 2, Rt=1.79 min in SFC). $^1$H NMR (400 MHz, CDCl$_3$) $\delta_H$=9.44 (d, 1H), 8.52 (d, 1H), 8.26 (d, 1H), 8.06 (dd, 1H), 5.93-5.87 (m, 1H), 3.10-2.96 (m, 1H), 2.73-2.60 (m, 1H), 2.37-2.23 (m, 1H), 1.60 (d, 3H). LCMS $R_t$=1.18 min in 2.0 min chromatography, MS ESI calcd. for $C_{16}H_{12}F_6N_5O$ [M+H]$^+$ 404.1, found 403.9.

Example 19: 3-(3,3-difluorocyclobutyl)-6-[5-fluoro-6-[(1S)-2,2,2-trifluoro-1-methyl-ethoxy]-3-pyridyl]-[1,2,4]triazolo[4,3-a]pyrazine Synthesis of A33: To a mixture of 3,3-difluorocyclobutanecarboxylic acid (72.92 mg, 0.54 mmol), HOBt (137.91 mg, 1.02 mmol) in DCM (20 mL) was added EDCI (146.73 mg, 0.77 mmol), DIPEA (0.27 mL, 1.53 mmol) and then [5-[5-fluoro-6-[(1S)-2,2,2-trifluoro-1-methyl-ethoxy]-3-pyridyl]pyrazin-2-yl]hydrazine (200 mg, 0.51 mmol). The resulting mixture was stirred at 20° C. for 16 hours to give a solution. The solution was concentrated to give a residue. To the residue was added water (20 mL) and extracted with EtOAc (20 mL×2). The combined organic phase was washed with brine (20 mL×2), dried over anhydrous Na$_2$SO$_4$, filtered and concentrated to give the crude product (220 mg, 409.9 μmol) as a solid. LCMS $R_t$=0.83 min in 1.5 min chromatography, MS ESI calcd. for $C_{17}H_{16}F_6N_5O_2$[M+H]$^+$ 436.0, found 436.1.

Synthesis of Compound 19: A solution of 3,3-difluoro-N'-[5-[5-fluoro-6-[(1S)-2,2,2-trifluoro-1-methyl-ethoxy]-3-pyridyl]pyrazin-2-yl]cyclobutanecarbohydrazide (200 mg, 0.46 mmol) in acetic acid (10 mL, 0.46 mmol) was stirred at 120° C. for 16 hours to give a solution. The mixture was cooled to room temperature, and concentrated to give a residue. To the residue was diluted with EtOAc (20 mL), then basified with sat. NaHCO$_3$ to pH=8-9, and extracted with EtOAc (20 mL×2). The combined organic phase was washed with water (20 mL) and brine (20 mL), dried over Na$_2$SO$_4$, filtered and concentrated to give the crude product. The crude product was purified by Prep-HPLC (Boston Prime C18 (150 mm×30 mm, 5 μm), A=H$_2$O (0.05% NH$_4$OH) and B=CH$_3$CN; 58-88% B over 9 minutes) to give the product (91.32 mg, 218.8 μmol) as a solid. $^1$H NMR (400 MHz, CDCl$_3$+D$_2$O) $\delta_H$=9.43 (d, 1H), 8.47 (d, 1H), 8.10-7.99 (m, 2H), 5.96-5.84 (m, 1H), 3.86-3.72 (m, 1H), 3.43-3.18 (m, 4H), 1.60 (d, 3H). LCMS $R_t$=1.09 min in 2.0 min chromatography, MS ESI calcd. for $C_{17}H_{14}F_6N_5O$ [M+H]$^+$ 418.1, found 418.0.

Example 20: 3-(3,3-difluorocyclobutyl)-6-[5-fluoro-6-[(1R)-2,2,2-trifluoro-1-methyl-ethoxy]-3-pyridyl]-[1,2,4]triazolo[4,3-a]pyrazine

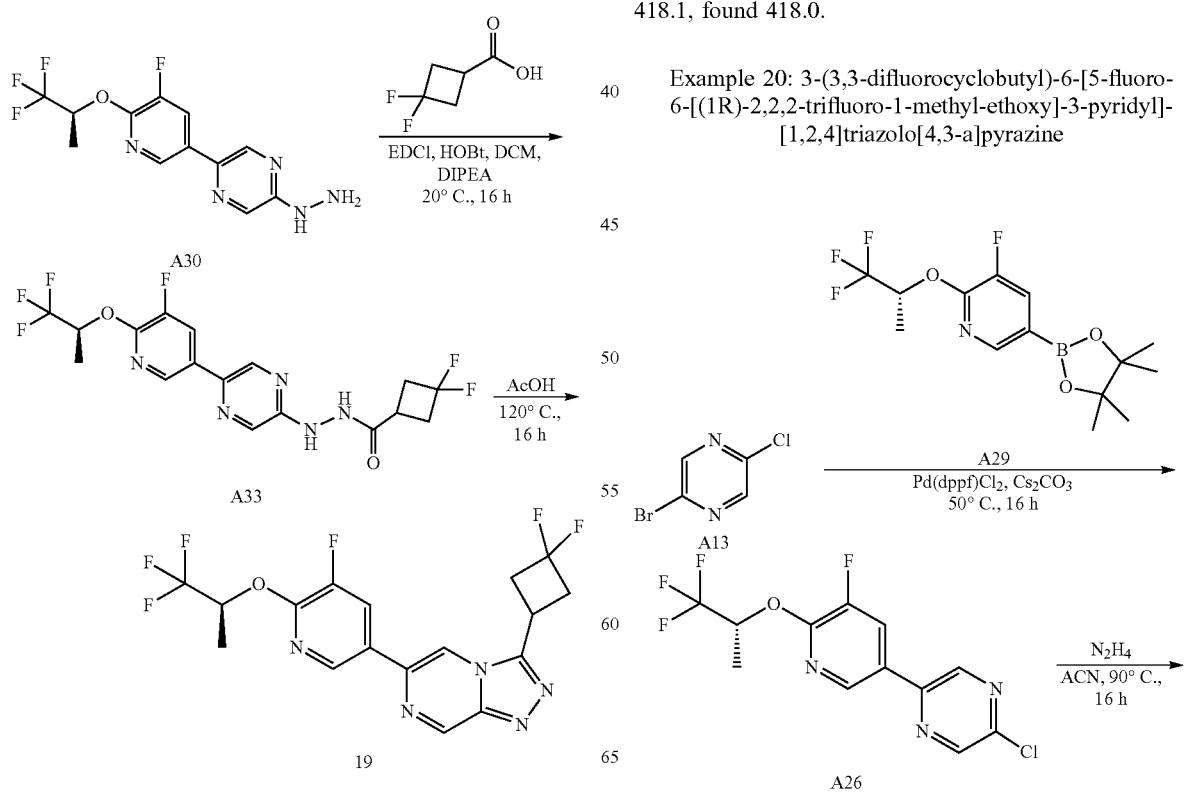

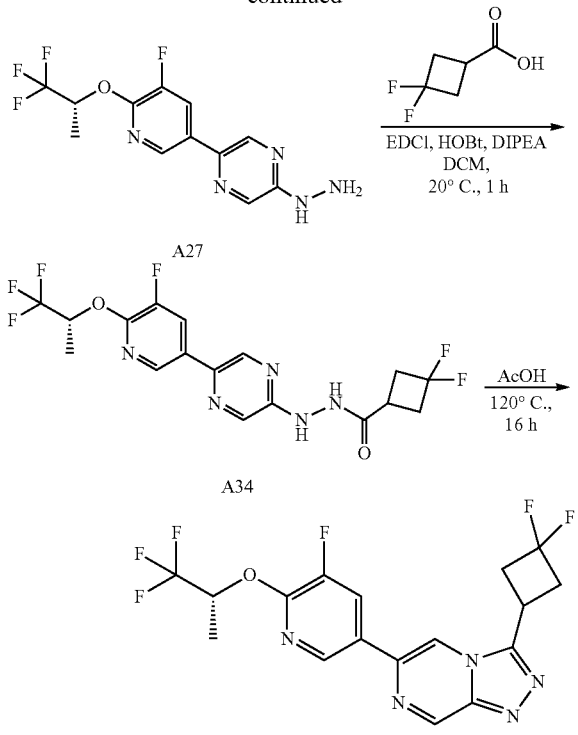

Synthesis of A26: A mixture of 2-bromo-5-chloro-pyrazine (2 g, 10.34 mmol), 3-fluoro-5-(4,4,5,5-tetramethyl-1,3,2-dioxaborolan-2-yl)-2-[(1R)-2,2,2-trifluoro-1-methylethoxy]pyridine (3.12 g, 9.31 mmol), Pd(dppf)Cl$_2$ (1.13 g, 1.55 mmol) and Cs$_2$CO$_3$ (6.74 g, 20.68 mmol) in 1,4-Dioxane (100 mL) and Water (10 mL) was stirred under N$_2$ at 50° C. for 5 hours to give a mixture. The mixture was cooled to room temperature, diluted with EtOAc (10 mL), filtered with silica gel, eluted with EtOAc (20 mL) and concentrated to give the crude product. The product was purified by flash chromatography on silica gel (EtOAc in PE=0% to 20%) to give the product (2500 mg, 7.21 mmol, 70% yield) as a solid. $^1$H NMR (400 MHz, CDCl$_3$) $\delta_H$=8.77 (d, 1H), 8.64 (d, 1H), 8.53 (d, 1H), 8.08 (dd, 1H), 5.90 (spt, 1H), 1.59 (d, 3H).

Synthesis of A27: A mixture of 2-chloro-5-[5-fluoro-6-[(1R)-2,2,2-trifluoro-1-methyl-ethoxy]-3-pyridyl]pyrazine (2 g, 6.22 mmol) and hydrazine (1.99 g, 62.18 mmol) in MeCN (20 mL) was heated to 90° C. and stirred for 16 hours to give a mixture. After cooling to room temperature, the reaction mixture was concentrated to remove most of MeCN, then diluted with H$_2$O (100 mL). The mixture was extracted with EtOAc (150 mL×2). The combined organic phase was washed with brine (100 mL), dried over Na$_2$SO$_4$, filtered and concentrated to give the crude product (2000 mg, 6.30 mmol) as an oil. $^1$H NMR (400 MHz, DMSO-d$_6$) $\delta_H$=8.62 (d, 1H), 8.58 (d, 1H), 8.29-8.24 (m, 2H), 8.19 (s, 1H), 6.00-5.92 (m, 1H), 4.37 (s, 2H), 1.51 (d, 3H).

Synthesis of A34: To a mixture of 3,3-difluorocyclobutanecarboxylic acid (94.38 mg, 0.69 mmol), DIPEA (0.33 mL, 1.89 mmol), EDCI (181.28 mg, 0.95 mmol) and HOBt (170.38 mg, 1.26 mmol) in DCM (20 mL) was added the [5-[5-fluoro-6-[(1R)-2,2,2-trifluoro-1-methyl-ethoxy]-3-pyridyl]pyrazin-2-yl]hydrazine (200 mg, 0.63 mmol) and the mixture was stirred at 20° C. for 1 hour to give a mixture. The mixture was diluted with sat. NH$_4$Cl (80 mL) and extracted with DCM (80 mL×2). The combined organic phase was washed with brine (40 mL), dried over Na$_2$SO$_4$, and filtered. The filtrate was concentrated to give the crude product (450 mg, crude) as an oil. The crude product was used directly in next step without any purification. LCMS R$_f$=1.04 min in 1.5 min chromatography, MS ESI calcd. for C$_{17}$H$_{16}$F$_6$N$_5$O$_2$ [M+H]$^+$ 436.1, found 436.1.

Synthesis of Compound 20: A mixture of 3,3-difluoro-N'-[5-[5-fluoro-6-[(1R)-2,2,2-trifluoro-1-methyl-ethoxy]-3-pyridyl]pyrazin-2-yl]cyclobutanecarbohydrazide (450 mg, 1.03 mmol) in Acetic acid (20 mL) was stirred at 120° C. for 16 hours to give a mixture. The mixture was cooled to room temperature, and concentrated to give the crude product. The crude product was diluted with EtOAc (10 mL), then basified with sat. NaHCO$_3$ to pH=8-9, and extracted with EtOAc (20 mL×2). The combined organic phase was washed with water (20 mL) and brine (15 mL), dried over Na$_2$SO$_4$, filtered and concentrated to give the crude product. The crude product was purified by Prep-HPLC (Boston Prime C18 (150 mm×30 mm, 5 μm), A=H$_2$O (0.05% NH$_4$OH) and B=CH$_3$CN; 65-95% B over 8 minutes) to give the product (55.48 mg, 0.13 mmol) as a solid. $^1$H NMR (400 MHz, CDCl$_3$+D$_2$O) $\delta_H$=9.43 (d, 1H), 8.47 (d, 1H), 8.08-8.01 (m, 2H), 5.97-5.83 (m, 1H), 3.86-3.70 (m, 1H), 3.43-3.19 (m, 4H), 1.60 (d, 3H). LCMS R$_f$=1.11 min in 2.0 min chromatography, MS ESI calcd. for C$_{17}$H$_{14}$F$_6$N$_5$O [M+H]$^+$ 418.1, found 418.0.

Example 21: 6-[6-[(2,2-difluorocyclopropyl)methoxy]-5-fluoro-3-pyridyl]-3-(difluoromethyl)-[1,2,4]triazolo[4,3-b]pyridazine

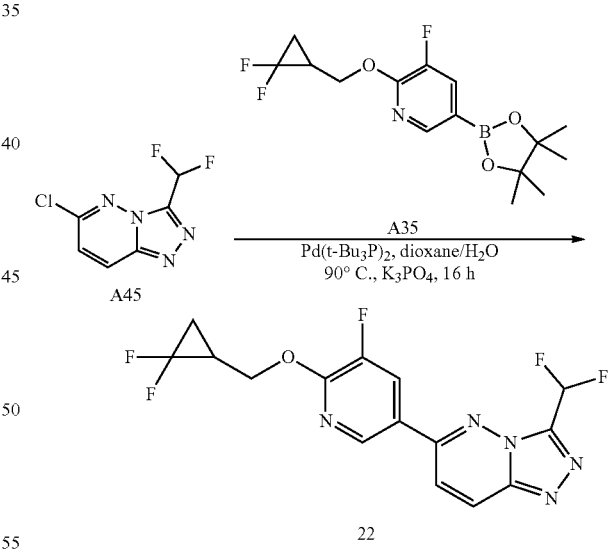

A mixture of 6-chloro-3-(difluoromethyl)-[1,2,4]triazolo[4,3-b]pyridazine (150 mg, 0.73 mmol), 2-[(2,2-difluorocyclopropyl)methoxy]-3-fluoro-5-(4,4,5,5-tetramethyl-1,3,2-dioxaborolan-2-yl)pyridine (289.61 mg, 0.88 mmol), K$_3$PO$_4$ (311.35 mg, 1.47 mmol) and Pd(t-Bu$_3$P)$_2$ (56.21 mg, 0.11 mmol) in 1,4-Dioxane (20 mL) and Water (2 mL) was stirred at 80° C. under N$_2$ for 16 hours to give a mixture. The mixture was cooled to room temperature and filtered through Celite. The filtrate was concentrated to give a residue. To the residue was added water (30 mL) and extracted with EtOAc (30 mL×2). The combined organic phase was dried over anhydrous Na₂SO₄, filtered and concentrated to give the crude product. The crude product was purified by flash chromatography column on silica gel (EtOAc in PE=0% to 50% to 80%) to give the product (135 mg). The crude product (35 mg) was purified by trituration from DCM/n-hexane (2 mL/4 mL) at 60° C. to give the product (30.61 mg, 0.08 mmol) as a solid. ¹H NMR (400 MHz, MeOD-d₃) $\delta_H$=8.73 (d, 1H), 8.41 (d, 1H), 8.29 (dd, 1H), 8.08 (d, 1H), 7.70-7.40 (m, 1H), 4.72-4.63 (m, 1H), 4.54-4.46 (m, 1H), 2.36-2.20 (m, 1H), 1.71-1.60 (m, 1H), 1.49-1.38 (m, 1H). LCMS $R_t$=1.19 min in 2.0 min chromatography, MS ESI calcd. for $C_{15}H_{11}F_5N_5O$ [M+H]⁺ 372.1, found 371.9.

Example 22: 6-[6-[[(1R)-2,2-difluorocyclopropyl]methoxy]-5-fluoro-3-pyridyl]-3-(difluoromethyl)-[1,2,4]triazolo[4,3-b]pyridazine & 6-[6-[[(1S)-2,2-difluorocyclopropyl]methoxy]-5-fluoro-3-pyridyl]-3-(difluoromethyl)-[1,2,4]triazolo[4,3-b]pyridazine

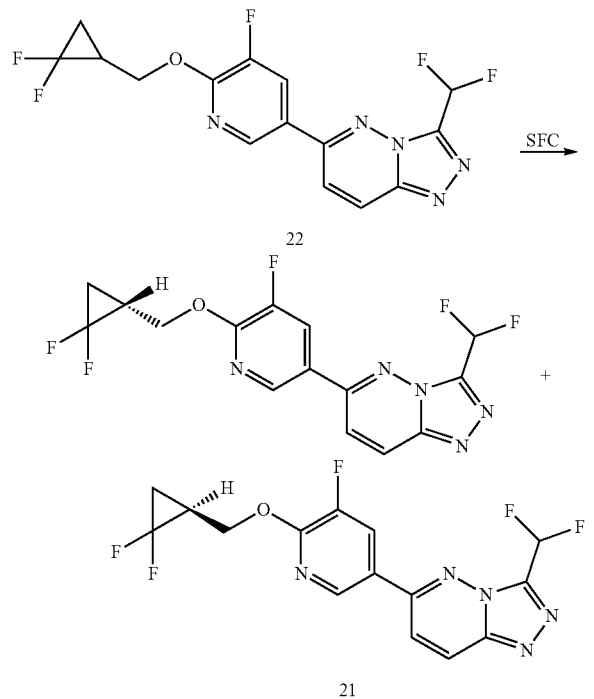

Compound 22 was analyzed by SFC to show two peaks (Isomer 1, Peak 1: Rt=3.972 min, Isomer 2, Peak 2: Rt=4.124 min). Method: Column: Chiralpak AD-3 150×4.6 mm I.D., 3 um Mobile phase: Methanol (0.05% DEA) in CO₂, Gradient: from 5% to 40% of B in 5.5 min, then 5% of B for 1.5 min, Flow rate: 2.5 mL/min Column temperature: 40° C. Compound 22 was purified by SFC (DAICEL CHIRALPAK AD-H (250 mm×30 mm, 5 μm); A=CO₂ and B=0.1% NH₃·H₂O-MeOH; 35° C.; 50 mL/min; 20% B; 8 min run; 35 injections, Rt of Peak 1=9.95 min, Rt of Peak 2=10.80 min) to give Isomer 1 (Peak 1, Rt=3.972 min in SFC) as a solid and Isomer 2 (Peak 2: Rt=4.124 min in SFC) as a solid. Note: the enantiomers were randomly assigned.

Isomer 1: (32.26 mg, 86.9 μmol) (Peak 1, Rt=3.972 min in SFC). ¹H NMR (400 MHz, MeOD-d₄) $\delta_H$=8.73 (d, 1H), 8.41 (d, 1H), 8.29 (dd, 1H), 8.08 (d, 1H), 7.75 (t, 1H), 4.73-4.63 (m, 1H), 4.56-4.45 (m, 1H), 2.37-2.18 (m, 1H), 1.73-1.59 (m, 1H), 1.49-1.36 (m, 1H). LCMS $R_t$=1.18 min in 2.0 min chromatography, MS ESI calcd. for $C_{15}H_{11}F_5N_5O$ [M+H]⁺ 372.1, found 372.0.

Isomer 2: (35.56 mg, 95.8 μmol) (Peak 2: Rt=4.124 min in SFC). ¹H NMR (400 MHz, MeOD-d₄) $\delta_H$=8.73 (d, 1H), 8.41 (d, 1H), 8.29 (dd, 1H), 8.08 (d, 1H), 7.75 (t, 1H), 4.71-4.64 (m, 1H), 4.54-4.46 (m, 1H), 2.37-2.19 (m, 1H), 1.73-1.58 (m, 1H), 1.49-1.36 (m, 1H). LCMS $R_t$=1.18 min in 2.0 min chromatography, MS ESI calcd. for $C_{15}H_{11}F_5N_5O$ [M+H]⁺ 372.1, found 372.0.

Example 23: 6-[6-[(2,2-difluorocyclopropyl)methoxy]-5-fluoro-3-pyridyl]-3-(trifluoromethyl)-[1,2,4]triazolo[4,3-b]pyridazine

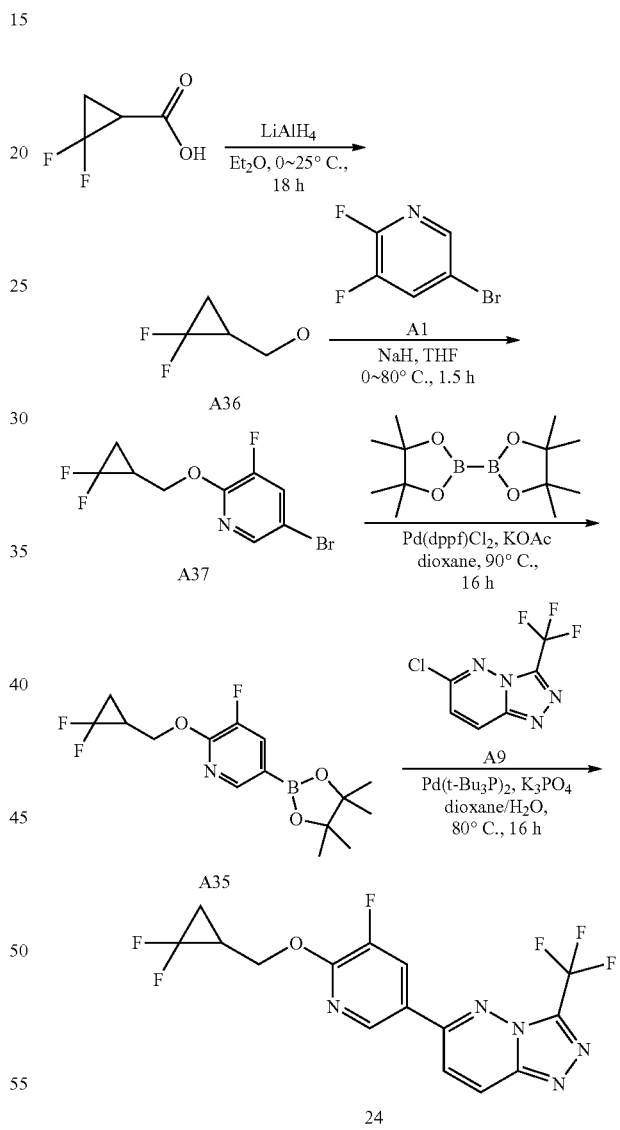

Synthesis of A36: To a solution of 2,2-difluorocyclopropanecarboxylic acid (1 g, 8.19 mmol) in Ether (30 mL) was added LiAlH₄ (466.33 mg, 12.29 mmol) slowly at 0° C. over 10 mins.

After the addition, the resulting suspension was allowed to warm to 25° C. and stirred for a further 18 hours to give a suspension. The reaction mixture was then cooled with an ice bath, and then 2M NaOH (~1 mL) was added in a dropwise manner to quench the reaction followed by H₂O (1 mL). The mixture was filtered, and rinsed with Et$_2$O (2×10 mL). The filtrate was concentrated to give a residue. Then the residue was re-dissolved in DCM (20 mL). Anhydrous MgSO$_4$ was added to the organic phase and filtered. The filtrate was concentrated at 5-10° C. to give the crude product (680 mg, 6.29 mmol, 77% yield) as an oil. $^1$H NMR (400 MHz, CDCl$_3$) δ$_H$=3.85-3.59 (m, 2H), 1.99-1.73 (m, 2H), 1.56-1.39 (m, 1H), 1.24-1.08 (m, 1H).

Synthesis of A37: To a solution of (2,2-difluorocyclopropyl)methanol (680 mg, 6.29 mmol) in THF (20 mL) was added NaH (251.64 mg, 6.29 mmol) at 0° C. and stirred for 0.5 hour. Then to the solution was added 5-bromo-2,3-difluoro-pyridine (1.22 g, 6.29 mmol) and stirred at 80° C. for 1 hour to give a solution. After cooling to room temperature, to the solution was added saturated NH$_4$Cl (20 mL) at 0° C., and the mixture was extracted with EtOAc (50 mL×2). The combined organic phase was washed with brine (30 mL×2), dried over anhydrous Na$_2$SO$_4$, filtered and concentrated to give the crude product (1.5 g, 4.68 mmol) as an oil. LCMS R$_t$=0.99 min in 1.5 min chromatography, MS ESI calcd. For C$_9$H$_8$BrF$_3$NO [M+H]$^+$ 284.0, found 283.8.

Synthesis of A35: A mixture of 5-bromo-2-[(2,2-difluorocyclopropyl)methoxy]-3-fluoro-pyridine (1.5 g, 5.32 mmol), 4,4,5,5-tetramethyl-2-(4,4,5,5-tetramethyl-1,3,2-dioxaborolan-2-yl)-1,3,2-dioxaborolane (2.03 g, 7.98 mmol), KOAc (1.04 g, 10.64 mmol) and Pd(dppf)Cl$_2$ (583.68 mg, 0.80 mmol) in 1,4-Dioxane (50 mL) was stirred at 90° C. under N$_2$ for 16 hours to give a mixture. The mixture was cooled to room temperature and filtered through Celite. The filtrate was concentrated to give a residue. To the residue was added water (50 mL) and extracted with EtOAc (50 mL×2). The combined organic phase was dried over anhydrous Na$_2$SO$_4$, filtered and concentrated to give the crude product. The crude product was purified by flash chromatography column on silica gel (EtOAc in PE=0% to 2% to 5%) to give the product (1.6 g, 4.86 mmol) as an oil. LCMS R$_t$=1.46 min in 2.0 min chromatography, 10-80AB, MS ESI calcd. for C$_{15}$H$_{20}$BF$_3$NO$_3$ [M+H]$^+$ 330.1, found 330.0.

Synthesis of Compound 24: A mixture of 6-chloro-3-(trifluoromethyl)-[1,2,4]triazolo[4,3-b]pyridazine (150 mg, 0.67 mmol), 2-[(2,2-difluorocyclopropyl)methoxy]-3-fluoro-5-(4,4,5,5-tetramethyl-1,3,2-dioxaborolan-2-yl)pyridine (266.18 mg, 0.81 mmol), K$_3$PO$_4$ (286.17 mg, 1.35 mmol) and Pd(t-Bu$_3$P)$_2$ (51.67 mg, 0.10 mmol) in 1,4-Dioxane (20 mL) and Water (2 mL) was stirred at 80° C. under N$_2$ for 16 hours to give a mixture. The mixture was cooled to room temperature and filtered through Celite. The filtrate was concentrated to give a residue. To the residue was added water (30 mL) and extracted with EtOAc (30 mL×2). The combined organic phase was dried over anhydrous Na$_2$SO$_4$, filtered and concentrated to give the crude product. The crude product was purified by flash chromatography column on silica gel (EtOAc in PE=0% to 50% to 80%) to give the product (135 mg, 46% yield). The crude product (35 mg) was purified by triturated from DCM/n-hexane (2 mL/4 mL) at 60° C. to give the product (26.8 mg, 67.0 µmol) as a solid. $^1$H NMR (400 MHz, CDCl$_3$) δ$_H$=8.56 (d, 1H), 8.34 (d, 1H), 8.10 (dd, 1H), 7.74 (d, 1H), 4.59 (d, 2H), 2.31-2.16 (m, 1H), 1.68-1.59 (m, 1H), 1.43-1.32 (m, 1H). LCMS R$_t$=1.28 min in 2.0 min chromatography, MS ESI calcd. for C$_{15}$H$_{10}$F$_6$N$_5$O [M+H]$^+$ 390.1, found 390.0.

Example 24: 6-[6-[[(1R)-2,2-difluorocyclopropyl]methoxy]-5-fluoro-3-pyridyl]-3-(trifluoromethyl)-[1,2,4]triazolo[4,3-b]pyridazine & 6-[6-[[(1S)-2,2-difluorocyclopropyl]methoxy]-5-fluoro-3-pyridyl]-3-(trifluoromethyl)-[1,2,4]triazolo[4,3-b]pyridazine

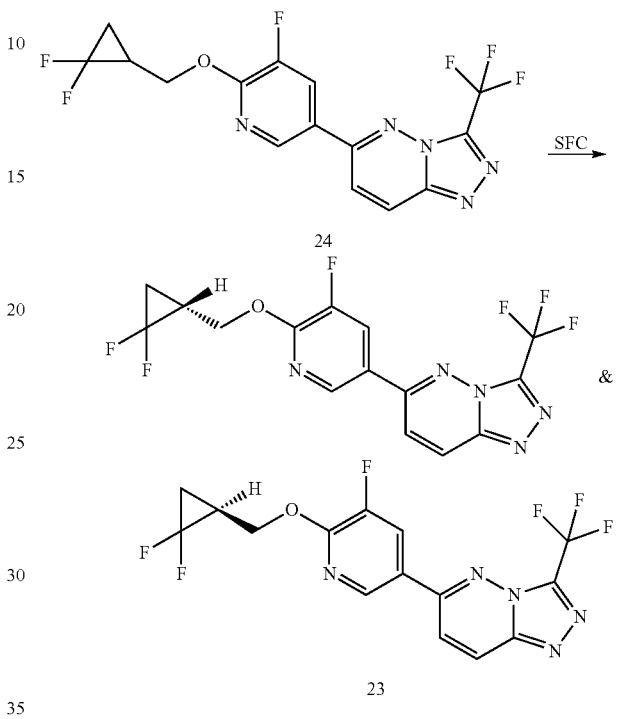

Compound 24 was analyzed by SFC to show two peaks (Isomer 1, Peak 1: Rt=3.231 min, Isomer 2, Peak 2: Rt=3.372 min). Method: Column: Chiralpak AD-3 150×4.6 mm I.D., 3 um Mobile phase: Methanol (0.05% DEA) in CO$_2$, Gradient: from 5% to 40% of B in 5.5 min, then 5% of B for 1.5 min, Flow rate: 2.5 mL/min Column temperature: 40° C. Note: the enantiomers were randomly assigned.

Compound 24 was separated by SFC (DAICEL CHIRALPAK AD-H (250 mm×30 mm, 5 µm); A=CO$_2$ and B=0.1% NH$_3$·H$_2$O-MeOH; 35° C.; 50 mL/min; 15% B; 11 min run; 28 injections, Rt of Peak 1=9.25 min, Rt of Peak 2=9.91 min) to give Isomer 1 (Peak 1, Rt=3.231 min in SFC) as a solid and Isomer 2 (50 mg) a solid.

Isomer 2 (50 mg) was further purified by SFC (DAICEL CHIRALPAK AD-H (250 mm×30 mm, 5 µm); A=CO$_2$ and B=0.1% NH$_3$·H$_2$O-MeOH; 35° C.; 50 mL/min; 20% B; 9 min run; 14 injections, Rt of Peak 1=7.15 min, Rt of Peak 2=7.50 min) to give Isomer 2 (Peak 2, Rt=3.372 min in SFC) as a solid.

Isomer 1: (26.39 mg, 67.8 µmol) (Peak 1, Rt=3.231 min in SFC). $^1$H NMR (400 MHz, CDCl$_3$) δ$_H$=8.56 (d, 1H), 8.34 (d, 1H), 8.10 (dd, 1H), 7.74 (d, 1H), 4.65-4.52 (m, 2H), 2.31-2.15 (m, 1H), 1.68-1.59 (m, 1H), 1.43-1.32 (m, 1H). LCMS R$_t$=1.29 min in 2.0 min chromatography, MS ESI calcd. for C$_{15}$H$_{10}$F$_6$N$_5$O [M+H]$^+$ 390.1, found 390.0.

Isomer 2 (41.42 mg, 106.4 µmol) (Peak 2: Rt=3.372 min in SFC). $^1$H NMR (400 MHz, CDCl$_3$) δ$_H$=8.56 (d, 1H), 8.34 (d, 1H), 8.10 (dd, 1H), 7.74 (d, 1H), 4.66-4.51 (m, 2H), 2.32-2.17 (m, 1H), 1.68-1.61 (m, 1H), 1.42-1.33 (m, 1H). LCMS R$_t$=1.29 min in 2.0 min chromatography, MS ESI calcd. for C$_{15}$H$_{10}$F$_6$N$_5$O [M+H]$^+$ 390.1, found 390.0.

Example 25: 6-[5-fluoro-6-(2,2,3,3-tetrafluorocyclobutoxy)-3-pyridyl]-3-(trifluoromethyl)-[1,2,4]triazolo[4,3-b]pyridazine

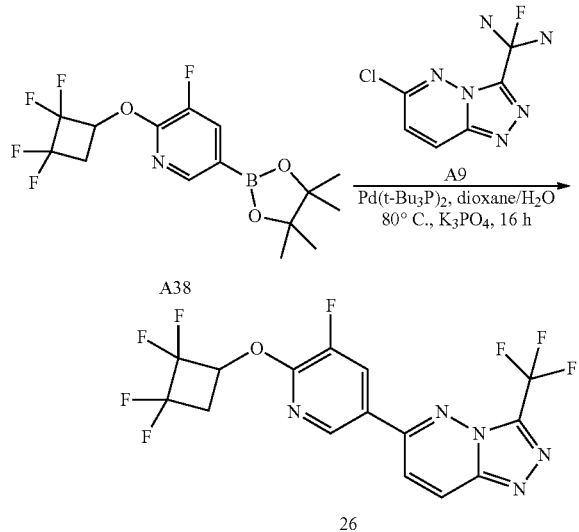

A mixture of 6-chloro-3-(trifluoromethyl)-[1,2,4]triazolo[4,3-b]pyridazine (100 mg, 0.45 mmol), Pd(t-Bu₃P)₂ (34.44 mg, 0.07 mmol), K₃PO₄ (190.78 mg, 0.90 mmol), and 3-fluoro-2-(2,2,3,3-tetrafluorocyclobutoxy)-5-(4,4,5,5-tetramethyl-1,3,2-dioxaborolan-2-yl)pyridine (246.07 mg, 0.67 mmol) in 1,4-Dioxane (2 mL) and Water (0.20 mL) was stirred at 80° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Waters Xbridge (150 mm×25 mm, 5 μm), A=H₂O (10 mM NH₄HCO₃) and B=CH₃CN; 46-76% B over 6 minutes) to give the product (12.23 mg, 28.7 μmol) as a solid. $^1$H NMR (400 MHz, CDCl₃) $\delta_H$=8.60 (d, 1H), 8.37 (d, 1H), 8.17 (dd, 1H), 7.75 (d, 1H), 5.68-5.53 (m, 1H), 3.24-3.05 (m, 1H), 2.95-2.70 (m, 1H). LCMS R$_t$=1.17 min in 2 min chromatography, MS ESI calcd. for C₁₅H₈F₈N₅O [M+H]⁺ 426.1, found 426.0.

Example 26: 6-[5-fluoro-6-[(1R)-2,2,3,3-tetrafluorocyclobutoxy]-3-pyridyl]-3-(trifluoromethyl)-[1,2,4]triazolo[4,3-b]pyridazine & 6-[5-fluoro-6-[(1S)-2,2,3,3-tetrafluorocyclobutoxy]-3-pyridyl]-3-(trifluoromethyl)-[1,2,4]triazolo[4,3-b]pyridazine

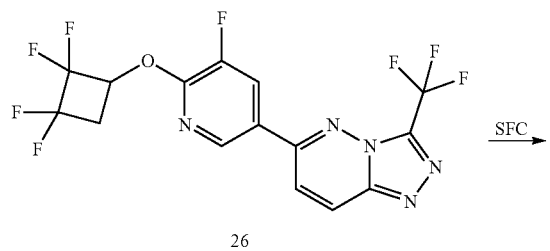

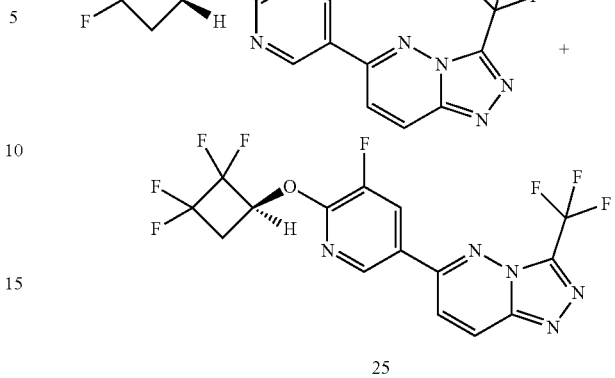

Compound 26 (70 mg, 0.16 mmol) was analyzed by SFC to show two peaks (Isomer 1, Peak 1: Rt=2.28 min, Isomer 2, Peak 2: Rt=2.36 min). Method: Column: ChiralCel OJ-H 150×4.6 mm I.D., 5 μm Mobile phase: A: CO₂ B: Ethanol (0.05% DEA) Gradient: from 5% to 40% of B in 5.5 min, then 5% of B for 1.5 min Flow rate: 2.5 mL/min Column temperature: 40° C.

Compound 26 was separated by SFC (DAICEL CHIRALCEL OJ-H (250 mm×30 mm, 5 μm); A=CO₂ and B=EtOH (0.1% NH₃H₂O); 38° C.; 50 mL/min; 20% B; 7 min run; 18 injections, Rt of peak 1=6.6 min, Rt of peak 2=7.1 min) to give Isomer 1 (3.59 mg, 8.40 μmol) (Peak 1, Rt=2.28 min in SFC) as a solid and Isomer 2, Peak 2 (~15 mg).

Isomer 2 (15 mg) was purified by SFC (DAICEL CHIRALCEL OJ-H (250 mm×30 mm, 5 μm); A=CO₂ and B=EtOH (0.1% NH₃H₂O); 38° C.; 50 mL/min; 20% B; 9 min run; 18 injections, Rt of peak 1=7.0 min, Rt of peak 2=7.5 min) to give Isomer 2 (3.50 mg, 8.20 μmol) (Peak 2: Rt=2.36 min in SFC).

Isomer 1 (3.59 mg, 8.40 μmol) (Peak 1, Rt=2.28 min in SFC). $^1$H NMR (400 MHz, CDCl₃) $\delta_H$=8.59 (d, 1H), 8.37 (d, 1H), 8.17 (dd, 1H), 7.75 (d, 1H), 5.73-5.48 (m, 1H), 3.24-3.06 (m, 1H), 2.93-2.74 (m, 1H). LCMS R$_t$=1.13 min in 2 min chromatography, MS ESI calcd. for C₁₅H₈F₈N₅O [M+H]⁺ 426.1, found 425.9.

Isomer 2 (3.50 mg, 8.20 μmol) (Peak 2: Rt=2.36 min in SFC). $^1$H NMR (400 MHz, CDCl₃) $\delta_H$=8.59 (d, 1H), 8.37 (d, 1H), 8.17 (dd, 1H), 7.75 (d, 1H), 5.70-5.50 (m, 1H), 3.22-3.06 (m, 1H), 2.94-2.74 (m, 1H). LCMS R$_t$=1.10 min in 2 min chromatography, MS ESI calcd. for C₁₅H₈F₈N₅O [M+H]⁺ 426.1, found 425.9.

Example 27: 6-[6-[(1R)-2,2-difluoro-1-methyl-ethoxy]-5-fluoro-3-pyridyl]-3-(trifluoromethyl)-[1,2,4]triazolo[4,3-a]pyrazine & 6-[6-[(1S)-2,2-difluoro-1-methyl-ethoxy]-5-fluoro-3-pyridyl]-3-(trifluoromethyl)-[1,2,4]triazolo[4,3-a]pyrazine

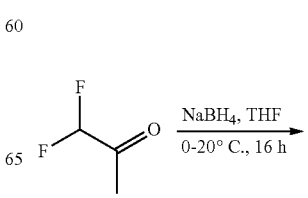

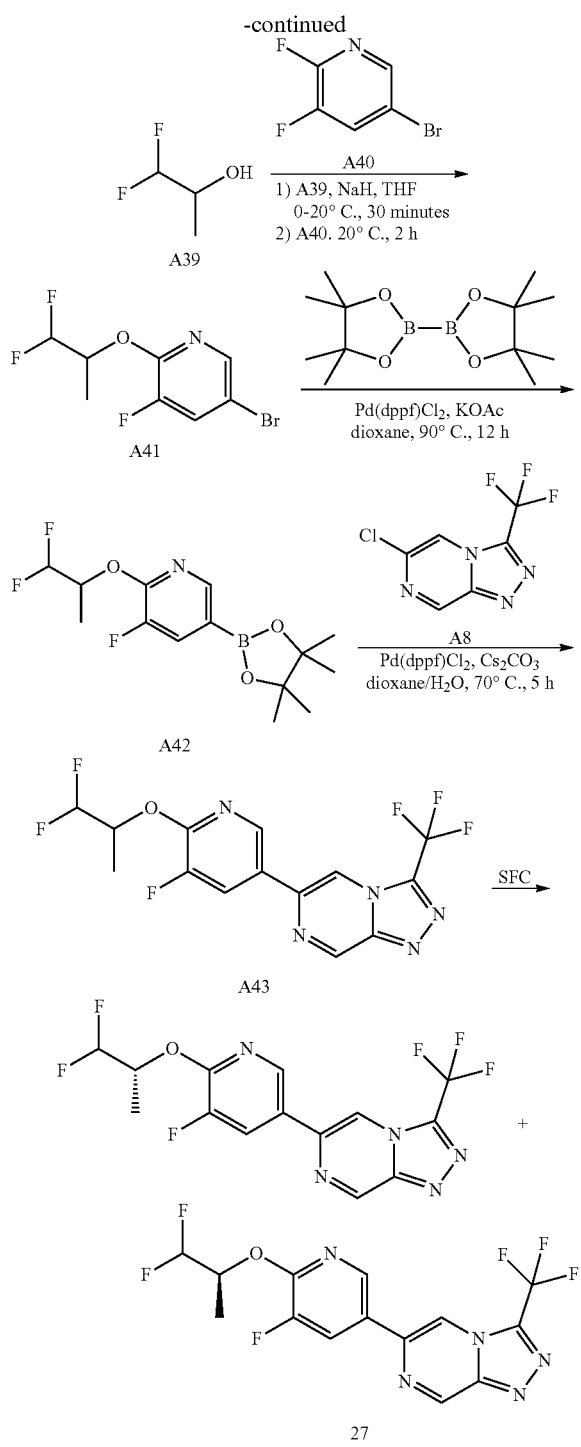

C. for 0.5 hour. To the mixture was added 5-bromo-2,3-difluoro-pyridine (1.2 g, 6.19 mmol), then the mixture was stirred at 20° C. for 2 hours. The mixture was quenched with sat. NH$_4$Cl (30 mL), then the mixture was extracted with EtOAc (50 mL×2). The combined organic phase was washed with brine (20 mL×2), dried over Na$_2$SO$_4$, filtered and concentrated to give the product (1500 mg, 5.55 mmol) as an oil. $^1$H NMR (400 MHz, DMSO-d$_6$) $\delta_H$=8.21-8.14 (m, 2H), 6.27 (dt, 1H), 5.49-5.38 (m, 1H), 1.36 (d, 3H).

Synthesis of A42: A mixture of 5-bromo-2-(2,2-difluoro-1-methyl-ethoxy)-3-fluoro-pyridine (1.5 g, 5.55 mmol), 4,4,5,5-tetramethyl-2-(4,4,5,5-tetramethyl-1,3,2-dioxaborolan-2-yl)-1,3,2-dioxaborolane (2.12 g, 8.33 mmol), Pd(dppf)Cl$_2$ (406.42 mg, 0.56 mmol) and KOAc (1.09 g, 11.11 mmol) in 1,4-Dioxane (40 mL) was stirred at 90° C. for 12 hours under N$_2$. After cooling to room temperature, the mixture was concentrated to give a residue. The residue was diluted with H$_2$O (30 mL), and the mixture was extracted with EtOAc (50 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 1% to 2%) to give the product (720 mg, 2.27 mmol) as an oil. $^1$H NMR (400 MHz, CDCl$_3$) $\delta_H$=8.25 (s, 1H), 7.68 (dd, 1H), 5.92 (dt, 1H), 5.62-5.47 (m, 1H), 1.47 (d, 3H), 1.34 (s, 12H).

Synthesis of A43: A mixture of 6-chloro-3-(trifluoromethyl)-[1,2,4]triazolo[4,3-a]pyrazine (150 mg, 0.67 mmol), 2-(2,2-difluoro-1-methyl-ethoxy)-3-fluoro-5-(4,4,5,5-tetramethyl-1,3,2-dioxaborolan-2-yl)pyridine (361.81 mg, 1.14 mmol), Pd(dppf)Cl$_2$ (73.66 mg, 0.10 mmol) and Cs$_2$CO$_3$ (437.32 mg, 1.34 mmol) in 1,4-Dioxane (10 mL) and Water (1 mL) was stirred at 70° C. for 5 hours under N$_2$. After cooling to room temperature, the mixture was diluted with H$_2$O (20 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 20% to 40%) to give the impure product. The impure product was purified by Prep-TLC (silica gel, PE:EtOAc=4:1) to give the product (100 mg, 0.27 mmol) as a solid. LCMS R$_t$=1.24 min in 2.0 min chromatography, MS ESI calcd. for C$_{14}$H$_{10}$F$_6$N$_5$O [M+H]$^+$ 378.1, found 378.1.

Synthesis of Compound 27

A43 (100 mg, 0.27 mmol) was analyzed by SFC to show two peaks (Isomer 1, Peak 1: Rt=2.21 min, Isomer 2, Peak 2: Rt=2.33 min). Method: Column: Chiralcel OJ-3 150×4.6 mm I.D, 3 µm Mobile phase: A: CO$_2$ B: methanol (0.05% DEA), Gradient: from 5% to 40% of B in 5 min and hold 40% for 2.5 min, then 5% of B for 2.5 min Flow rate: 2.5 mL/min Column temp.: 35° C. Note: the enantiomers were randomly assigned.

A43 (100 mg, 0.27 mmol) was purified by SFC (Chiralpak AD 250 mm×30 mm, 5 µm; A=CO$_2$ and B=methanol (0.05% DEA); 35° C.; 50 mL/min; 40% B; 9 min run; 18 injections, Rt of Isomer 1, peak 1=6.47 min, Rt of Isomer 2, peak 2=6.97 min) to give Isomer 1 (13.05 mg, 34.6 µmol) (Peak 1: Rt=2.21 min in SFC) as a solid and Isomer 2, Peak 2 (40 mg).

Isomer 2 (40 mg) was purified by SFC (Chiralpak AD 250 mm×30 mm, 5 µm; A=CO$_2$ and B=methanol (0.05% DEA); 35° C.; 50 mL/min; 40% B; 9 min run; 10 injections, Rt of Synthesis of A39: To a mixture of 1,1-difluoropropan-2-one (1 g, 10.63 mmol) in THF (50 mL) was added NaBH$_4$ (201.1 mg, 5.32 mmol) at 0° C., then the mixture was stirred at 20° C. for 16 hours. The mixture was quenched with sat. NH$_4$Cl (30 mL), then the mixture was washed with brine (15 mL×2), dried over Na$_2$SO$_4$, filtered to give the crude product (1000 mg, 10.408 mmol, 98% yield) as a crude solution, which was used directly without any further purification.

Synthesis of A41: To a solution of 1,1-difluoropropan-2-ol (1 g, 10.41 mmol) in THF (50 mL) was added NaH (371.17 mg, 9.28 mmol) at 0° C., then the mixture was stirred at 20° peak 2=7.00 min) to give Isomer 2 (26.47 mg, 70.0 μmol) (Peak 2: Rt=2.33 min in SFC) as a solid.

Isomer 1 (13.05 mg, 34.6 μmol) (Peak 1: Rt=2.21 min in SFC). $^1$H NMR (400 MHz, CDCl$_3$) $\delta_H$=9.59 (d, 1H), 8.52 (d, 1H), 8.39 (s, 1H), 8.04 (dd, 1H), 6.01 (dt, 1H), 5.66-5.52 (m, 1H), 1.53 (d, 3H). LCMS R$_t$=1.27 min in 2.0 min chromatography, MS ESI calcd. for C$_{14}$H$_{10}$F$_6$N$_5$O [M+H]$^+$ 378.1, found 377.9.

Isomer 2 (26.47 mg, 70.0 μmol) (Peak 2: Rt=2.33 min in SFC). $^1$H NMR (400 MHz, CDCl$_3$) $\delta_H$=9.59 (d, 1H), 8.52 (d, 1H), 8.39 (s, 1H), 8.04 (dd, 1H), 6.01 (dt, 1H), 5.67-5.50 (m, 1H), 1.53 (d, 3H). LCMS PR$_t$=1.26 min in 2.0 min chromatography, MS ESI calcd. for C$_{14}$H$_{10}$F$_6$N$_5$O [M+H]$^+$ 378.1, found 377.9.

Example 28: 3-(2,2-difluorocyclopropyl)-6-[5-fluoro-6-(2,2,2-trifluoro-1,1-dimethyl-ethoxy)-3-pyridyl]-[1,2,4]triazolo[4,3-a]pyrazine

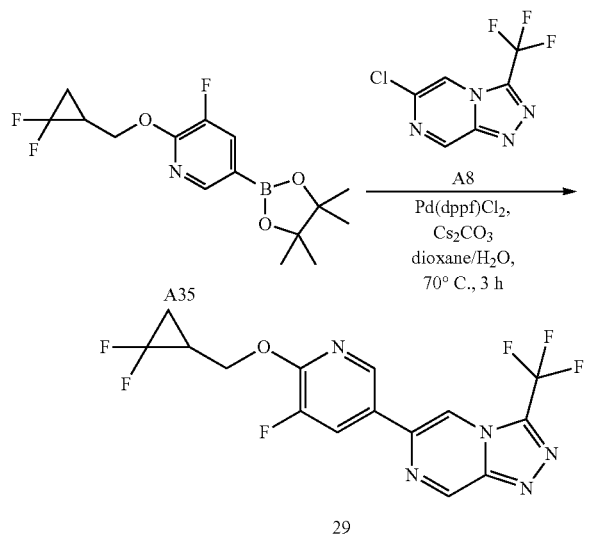

A mixture of 6-chloro-3-(trifluoromethyl)-[1,2,4]triazolo [4,3-a]pyrazine (150 mg, 0.67 mmol), 2-[(2,2-difluorocyclopropyl)methoxy]-3-fluoro-5-(4,4,5,5-tetramethyl-1,3,2-dioxaborolan-2-yl)pyridine (266.18 mg, 0.81 mmol), Cs$_2$CO$_3$ (439.16 mg, 1.35 mmol) and Pd(dppf)Cl$_2$ (73.97 mg, 0.10 mmol) in 1,4-Dioxane (20 mL) and Water (2 mL) was stirred at 70° C. under N$_2$ for 3 hours to give a mixture. The mixture was cooled to room temperature and filtered through Celite. The filtrate was concentrated to give a residue. To the residue was added water (30 mL), and the mixture was extracted with EtOAc (30 mL×2). The combined organic phase was dried over anhydrous Na$_2$SO$_4$, filtered and concentrated to give the crude product. The crude product was purified by Prep-HPLC (Boston prime (150 mm×30 mm 5 μm), A=H$_2$O (0.05% NH$_4$OH) and B=ACN; 52-82% B over 8 minutes) to give the product (101.1 mg). $^1$H NMR (CDCl$_3$+D$_2$O, 400 MHz) $\delta_H$=9.59 (d, 1H), 8.52 (d, 1H), 8.39 (s, 1H), 8.01 (dd, 1H), 4.57 (d, 2H), 2.32-2.14 (m, 1H), 1.67-1.53 (m, 1H), 1.43-1.31 (m, 1H). LCMS R$_t$=1.18 min in 2.0 min chromatography, MS ESI calcd. for C$_{15}$H$_{10}$F$_6$N$_5$O [M+H]$^+$ 390.1, found 390.0.

Example 29: 6-[6-[[(1R)-2,2-difluorocyclopropyl] methoxy]-5-fluoro-3-pyridyl]-3-(trifluoromethyl)-[1, 2,4]triazolo[4,3-a]pyrazine & 6-[6-[[(1S)-2,2-difluorocyclopropyl]methoxy]-5-fluoro-3-pyridyl]-3-(trifluoromethyl)-[1,2,4]triazolo[4,3-a]pyrazine

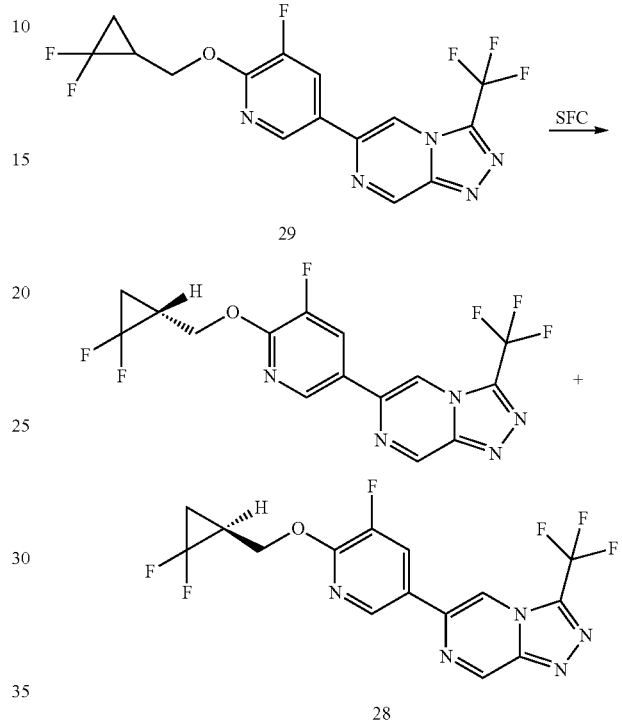

Compound 29 was analyzed by SFC to show two peaks (Isomer 1, Peak 1: Rt=2.93 min, Isomer 2, Peak 2: Rt=3.10 min). Method: Column: Chiralcel OJ-3 150×4.6 mm I.D., 3 μm Mobile phase: A: CO$_2$ B: iso-propanol (0.05% DEA) Gradient: from 5% to 40% of B in 5 min and from 40% to 5% of B in 0.5 min, hold 5% of B for 1.5 min, Flow rate: 2.5 mL/min, Column temp.: 35° C. Stereoisomers were randomly assigned.

Compound 29 was separated by SFC (DAICEL CHIRAL-CEL OD-H (250 mm×30 mm, 5 μm); A=CO$_2$ and B=0.1% NH$_3$·H$_2$O-EtOH; 38° C.; 60 mL/min; 25% B; 9 min run; 18 injections, Rt of Isomer 1, Peak 1=6.35 min, Rt of Isomer 2, Peak 2=7.4 min) to give Isomer 1 (8.44 mg, 21.7 μmol) (Peak 1, Rt=2.93 min in SFC) as a solid and Isomer 2 (3.57 mg, 9.20 μmol) (Peak 2: Rt=3.10 min in SFC) as a solid.

Isomer 1 (8.44 mg, 21.7 μmol) (Peak 1, Rt=2.93 min in SFC). $^1$H NMR (400 MHz, CDCl$_3$+D$_2$O) $\delta_H$=9.59 (s, 1H), 8.52 (d, 1H), 8.38 (s, 1H), 8.01 (dd, 1H), 4.57 (d, 2H), 2.30-2.16 (m, 1H), 1.67-1.56 (m, 1H), 1.42-1.33 (m, 1H). LCMS R$_t$=1.29 min in 2.0 min chromatography. MS ESI calcd. for C$_{15}$H$_{10}$F$_6$N$_5$O [M+H]$^+$ 390.1, found 390.1.

Isomer 2 (3.57 mg, 9.20 μmol) (Peak 2: Rt=3.10 min in SFC). $^1$H NMR (400 MHz, CDCl$_3$) $\delta_H$=9.61 (d, 1H), 8.53 (d, 1H), 8.40 (s, 1H), 8.03 (dd, 1H), 4.59 (d, 2H), 2.32-2.17 (m, 1H), 1.69-1.61 (m, 1H), 1.45-1.33 (m, 1H). LCMS R$_t$=1.29 min in 2.0 min chromatography, MS ESI calcd. for C$_{15}$H$_{10}$F$_6$N$_5$O [M+H]$^+$ 390.1, found 390.0.

Example 30: 6-[6-[(2,2-difluorocyclopropyl)methoxy]-5-fluoro-3-pyridyl]-3-(difluoromethyl)-[1,2,4]triazolo[4,3-a]pyrazine

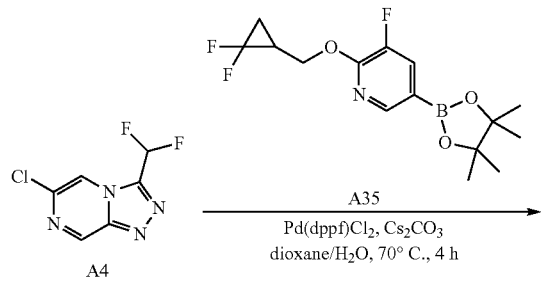

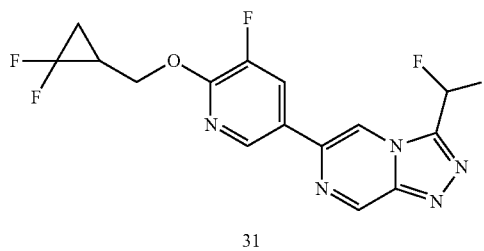

31

Example 31: 6-[6-[[(1R)-2,2-difluorocyclopropyl]methoxy]-5-fluoro-3-pyridyl]-3-(difluoromethyl)-[1,2,4]triazolo[4,3-a]pyrazine & 6-[6-[[(1S)-2,2-difluorocyclopropyl]methoxy]-5-fluoro-3-pyridyl]-3-(difluoromethyl)-[1,2,4]triazolo[4,3-a]pyrazine

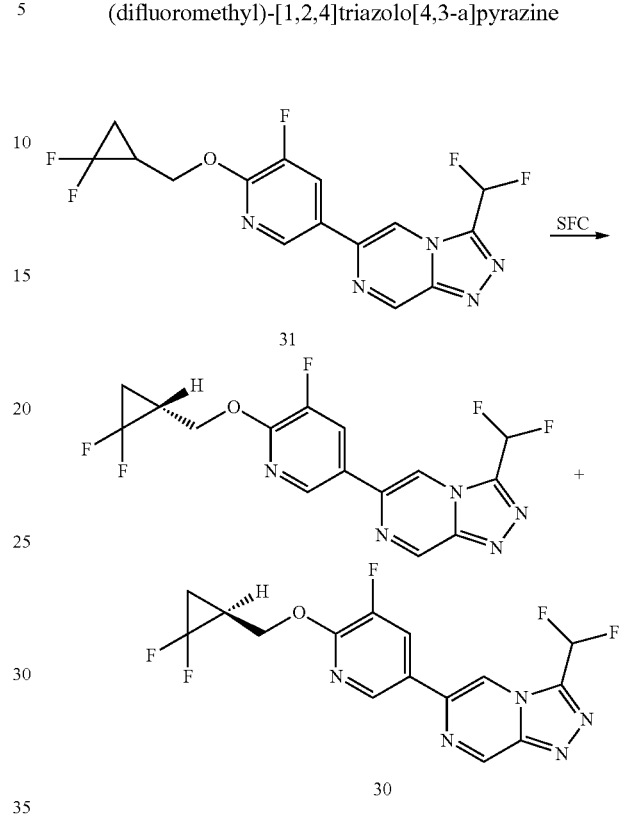

A mixture of 6-chloro-3-(difluoromethyl)-[1,2,4]triazolo[4,3-a]pyrazine (137.87 mg, 0.67 mmol), 2-[(2,2-difluorocyclopropyl)methoxy]-3-fluoro-5-(4,4,5,5-tetramethyl-1,3,2-dioxaborolan-2-yl)pyridine (266.18 mg, 0.81 mmol), $Cs_2CO_3$ (439.16 mg, 1.35 mmol) and $Pd(dppf)Cl_2$ (73.97 mg, 0.10 mmol) in 1,4-Dioxane (20 mL) and Water (2 mL) was stirred at 70° C. under $N_2$ for 4 hours to give a mixture. The mixture was cooled to room temperature and filtered through Celite. The filtrate was concentrated to give a residue. To the residue was added water (30 mL) and extracted with EtOAc (30 mL×2). The combined organic phase was dried over anhydrous $Na_2SO_4$, filtered and concentrated to give the crude product. The crude product was purified by Prep-HPLC (Boston Prime (150×30 mm, 5 μm), $A=H_2O$ (0.05% $NH_4OH$) and B=ACN; 46-76% B over 8 minutes) to give the impure product (65 mg, 26% yield) as a solid. The impure product was dissolved in PE/EtOAc (1:1, 10 ml), and filtered through silica gel, eluted with PE/EtOAc (1:1, 5 ml×3). The filtrate was concentrated to give the product (58.16 mg, 0.16 mmol) as a solid. $^1$H NMR (MeOD-$d_4$, 400 MHz) $\delta_H$=9.53 (d, 1H), 8.97 (d, 1H), 8.69 (d, 1H), 8.24 (dd, 1H), 7.58 (t, 1H), 4.67-4.59 (m, 1H), 4.50-4.43 (m, 1H), 2.34-2.19 (m, 1H), 1.71-1.59 (m, 1H), 1.47-1.37 (m, 1H). LCMS $R_t$=1.22 min in 2.0 min chromatography, MS ESI calcd. for $C_{15}H_{11}F_5N_5O$ [M+H]$^+$ 372.1, found 371.9.

Compound 31 was analyzed by SFC to show two peaks (Isomer 1, Peak 1: Rt=4.17 min, Isomer 2 Peak 2: Rt=4.44 min). Method: Column: Column: Chiralpak AD-3 150×4.6 mm I.D., 3 μm, Mobile phase: A: $CO_2$ B: methanol (0.05% DEA) Gradient: from 5% to 40% of B in 5 min and hold 40% for 2.5 min, then 5% of B for 2.5 min Flow rate: 2.5 mL/min Column temp.: 35° C. Stereochemistry randomly assigned.

Compound 31 (60 mg) was purified by SFC (DAICEL CHIRALCEL OD-H (250 mm×30 mm, 5 μm); $A=CO_2$ and B=0.1% $NH_3 \cdot H_2O$-EtOH; 38° C.; 60 mL/min; 25% B; 14 min run; 8 injections, Rt of Peak 1=11 min, Rt of Peak 2=12.5 min) to give Isomer 1 (25.17 mg, 0.07 mmol) (Peak 1, Rt=4.17 min in SFC) as a solid and Isomer 2 (26.57 mg, 0.07 mmol) (Peak 2: Rt=4.44 min in SFC as a solid.

Isomer 1 (25.17 mg, 0.07 mmol) (Peak 1, Rt=4.17 min in SFC). $^1$H NMR (MeOD, 400 MHz) $\delta_H$=9.53 (d, 1H), 8.97 (d, 1H), 8.69 (d, 1H), 8.24 (dd, 1H), 7.58 (t, 1H), 4.68-4.60 (m, 1H), 4.51-4.43 (m, 1H), 2.34-2.19 (m, 1H), 1.71-1.59 (m, 1H), 1.46-1.37 (m, 1H). LCMS $R_t$=1.22 min in 2.0 min chromatography, MS ESI calcd. for $C_{15}H_{11}F_5N_5O$ [M+H]$^+$ 372.1, found 372.0.

Isomer 2 (26.57 mg, 0.07 mmol) (Peak 2: Rt=4.44 min in SFC). $^1$H NMR (MeOD, 400 MHz) $\delta_H$=9.53 (d, 1H), 8.97 (d, 1H), 8.69 (d, 1H), 8.24 (dd, 1H), 7.58 (t, 1H), 4.68-4.60 (m, 1H), 4.51-4.43 (m, 1H), 2.32-2.21 (m, 1H), 1.70-1.59 (m, 1H), 1.47-1.36 (m, 1H). LCMS $R_t$=1.18 min in 2.0 min chromatography, MS ESI calcd. for $C_{15}H_{11}F_5N_5O$ [M+H]$^+$ 372.1, found 372.0.

Example 32: 6-[5-fluoro-6-(2,2,3,3-tetrafluorocyclobutoxy)-3-pyridyl]-3-(trifluoromethyl)-[1,2,4]triazolo[4,3-a]pyrazine

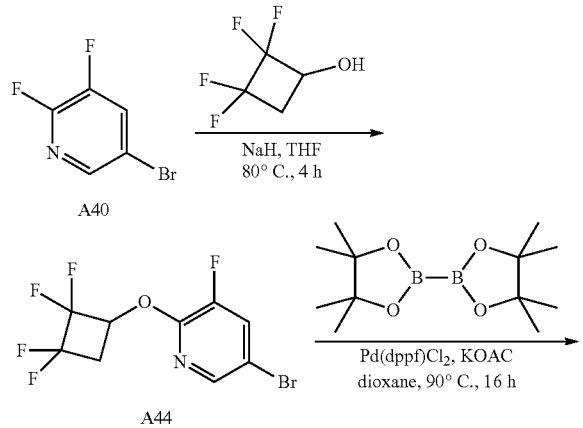

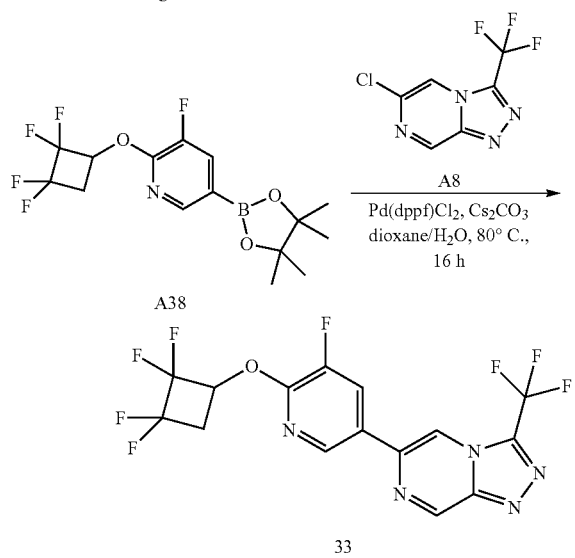

Synthesis of A44: To a solution of 2,2,3,3-tetrafluorocyclobutanol (830 mg, 5.76 mmol) in THF (20 mL) was added NaH (230.44 mg, 5.76 mmol). Then to the mixture was added 5-bromo-2,3-difluoro-pyridine (1117.54 mg, 5.76 mmol), and the mixture was stirred at 80° C. for 4 hours. After cooling to room temperature, the suspension was quenched with H$_2$O (30 mL), and extracted with EtOAc (30 mL×2). The combined organic phase was washed with brine (10 mL), dried over Na$_2$SO$_4$, filtered and concentrated to give the product (1100 mg, 3.35 mmol) as a colorless oil. LCMS R$_t$=1.18 min in 2 min chromatography, MS ESI calcd. for C$_9$H$_6$BrF$_5$NO [M+H]$^+$ 317.9, found 317.9.

Synthesis of A38: A mixture of 5-bromo-3-fluoro-2-(2,2,3,3-tetrafluorocyclobutoxy)pyridine (1 g, 3.14 mmol), 4,4,5,5-tetramethyl-2-(4,4,5,5-tetramethyl-1,3,2-dioxaborolan-2-yl)-1,3,2-dioxaborolane (1.2 g, 4.72 mmol), Pd(dppf)Cl$_2$ (345.10 mg, 0.47 mmol) and KOAc (617.16 mg, 6.29 mmol) in 1,4-Dioxane (20 mL) was stirred at 90° C. for 16 hours under N$_2$. After cooling to room temperature, the suspension was diluted with EtOAc (20 mL), filtered through silica gel, eluted with EtOAc (50 mL). The combined filtrates were concentrated to afford crude product (880 mg, 1.84 mmol) as an oil. LCMS R$_t$=1.30 min in 2 min chromatography, MS ESI calcd. for C$_{15}$H$_{18}$BF$_5$NO$_3$ [M+H]$^+$ 366.1, found 366.1.

Synthesis of Compound 33: A mixture of 6-chloro-3-(trifluoromethyl)-[1,2,4]triazolo[4,3-a]pyrazine (100 mg, 0.45 mmol), Pd(dppf)Cl$_2$ (49.31 mg, 0.07 mmol), Cs$_2$CO$_3$ (292.77 mg, 0.90 mmol), and 3-fluoro-2-(2,2,3,3-tetrafluorocyclobutoxy)-5-(4,4,5,5-tetramethyl-1,3,2-dioxaborolan-2-yl)pyridine (196.85 mg, 0.54 mmol) in 1,4-Dioxane (2 mL) and Water (0.20 mL) was stirred at 80° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by Prep-HPLC (Waters Xbridge (150 mm×25 mm, 5 μm) A=H$_2$O (10 mM NH$_4$HCO$_3$) and B=CH$_3$CN; 45-75% B over 6 minutes) to give the product (19.14 mg, 45.04 μmol, 10% yield) as a solid. $^1$H NMR (CDCl$_3$, 400 MHz) δ$_H$=9.60 (d, 1H), 8.55 (d, 1H), 8.42 (s, 1H), 8.11 (dd, 1H), 5.65-5.52 (m, 1H), 3.21-3.05 (m, 1H), 2.93-2.75 (m, 1H). LCMS R$_t$=1.16 min in 2 min chromatography, for C$_{15}$H$_8$F$_8$N$_5$O [M+H]$^+$ 426.1, found 425.9.

Example 33: 6-[5-fluoro-6-[(1R)-2,2,3,3-tetrafluorocyclobutoxy]-3-pyridyl]-3-(trifluoromethyl)-[1,2,4]triazolo[4,3-a]pyrazine & 6-[5-fluoro-6-[(1S)-2,2,3,3-tetrafluorocyclobutoxy]-3-pyridyl]-3-(trifluoromethyl)-[1,2,4]triazolo[4,3-a]pyrazine

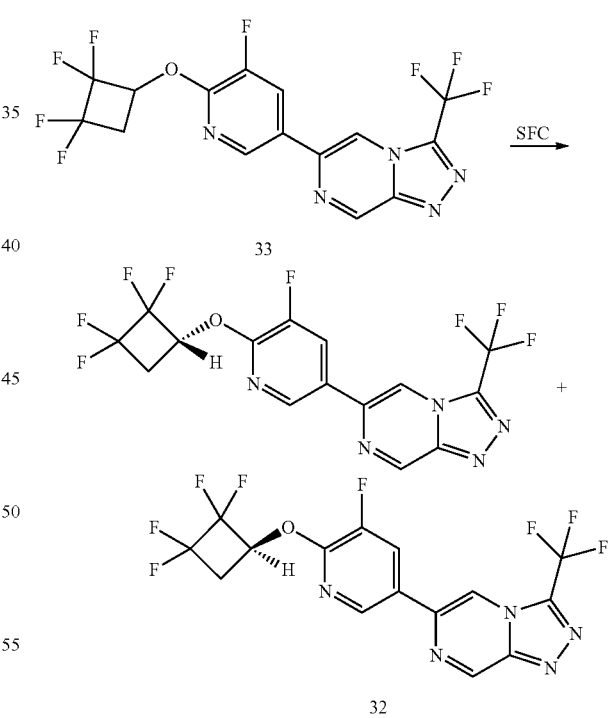

Compound 33 (70 mg, 0.16 mmol) was analyzed by SFC to show two peaks (Isomer 1, Peak 1: Rt=2.25 min, Isomer 2, Peak 2: Rt=2.54 min). Method: Column: ChiralCel OJ-H 150×4.6 mm I.D., 5um Mobile phase: A: CO$_2$ B: Ethanol (0.05% DEA) Gradient: from 5% to 40% of B in 5.5 min, then 5% of B for 1.5 min Flow rate: 2.5 mL/min Column temperature: 40° C. Note: the enantiomers were randomly assigned.

Compound 33 was separated by SFC (DAICEL CHIRAL-CEL OJ-H (250 mm×30 mm, 5 μm); A=CO₂ and B=EtOH (0.1% NH₃H₂O); 38° C.; 50 mL/min; 10% B; 7 min run; 7 injections, Rt of peak 1=4.4 min, Rt of peak 2=5.7 min) to give Isomer 1 (19.79 mg, 46.50 mmol) (Peak 1, Rt=2.25 min in SFC) as a solid and Isomer 2 (14.90 mg, 35 μmol) (Peak 2: Rt=2.54 min in SFC) as a solid.

Isomer 1 (19.79 mg, 46.50 mmol) (Peak 1, Rt=2.25 min in SFC). $^1$H NMR (CDCl₃, 400 MHz) $\delta_H$=9.60 (d, 1H), 8.55 (d, 1H), 8.43 (s, 1H), 8.11 (dd, 1H), 5.64-5.52 (m, 1H), 3.20-3.05 (m, 1H), 2.92-2.77 (m, 1H). LCMS R$_t$=1.10 min in 2 min chromatography, MS ESI calcd. for C₁₅H₈F₈N₅O [M+H]⁺ 426.1, found 426.0.

Isomer 2 (14.90 mg, 35 μmol) (Peak 2: Rt=2.54 min in SFC). $^1$H NMR (CDCl₃, 400 MHz) $\delta_H$=9.60 (d, 1H), 8.55 (d, 1H), 8.42 (s, 1H), 8.11 (dd, 1H), 5.64-5.53 (m, 1H), 3.21-3.06 (m, 1H), 2.92-2.76 (m, 1H). LCMS R$_t$=1.09 min in 2 min chromatography, MS ESI calcd. for C₁₅H₈F₈N₅O [M+H]⁺ 426.1, found 425.9.

Example 34: 6-[5-fluoro-6-(2,2,2-trifluoro-1,1-dimethyl-ethoxy)-3-pyridyl]-3-(trifluoromethyl)-[1,2,4]triazolo[4,3-b]pyridazine

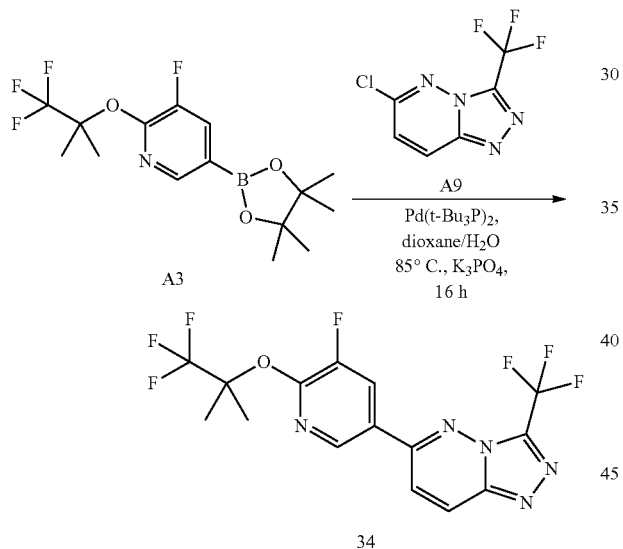

1H), 1.91 (s, 6H). LCMS R$_t$=1.23 min in 2 min chromatography, MS ESI calcd. for C₁₅H₁₁F₇N₅O [M+H]⁺ 410.1, found 410.0.

Example 35: 6-[6-(2,2,2-trifluoro-1,1-dimethyl-ethoxy)-3-pyridyl]-3-(trifluoromethyl)-[1,2,4]triazolo[4,3-a]pyrazine

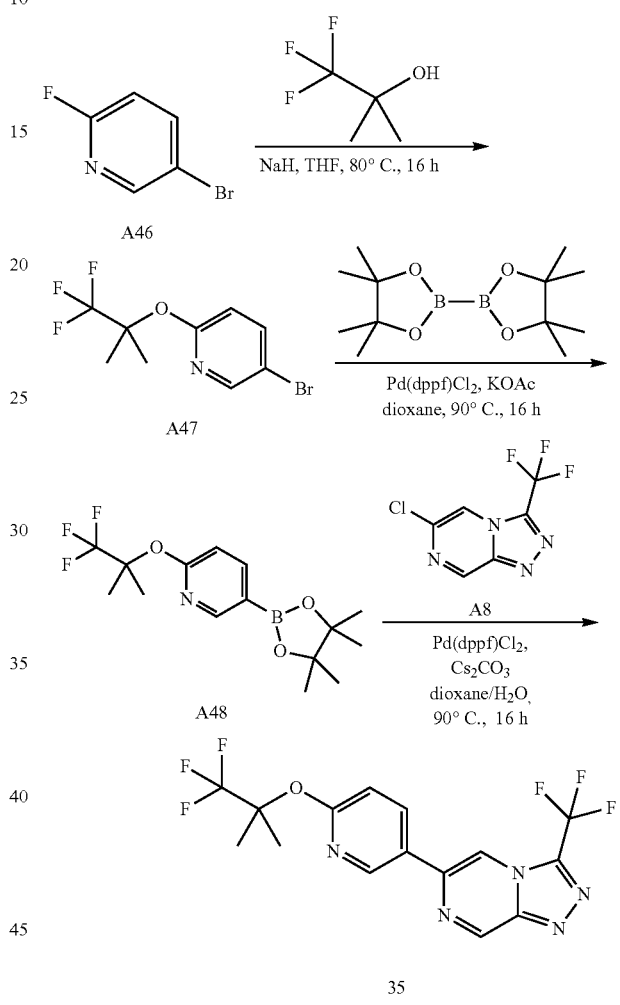

A mixture of 6-chloro-3-(trifluoromethyl)-[1,2,4]triazolo[4,3-b]pyridazine (100 mg, 0.45 mmol), Pd(t-Bu₃P)₂ (34.44 mg, 0.07 mmol), K₃PO₄ (190.78 mg, 0.90 mmol), and 3-fluoro-5-(4,4,5,5-tetramethyl-1,3,2-dioxaborolan-2-yl)-2-(2,2,2-trifluoro-1,1-dimethyl-ethoxy)pyridine (235.31 mg, 0.67 mmol) in Water (0.20 mL) and 1,4-Dioxane (2 mL) was stirred at 85° C. for 16 hours. After cooling to room temperature, the mixture was concentrated to the residue. The residue was diluted with H₂O (20 mL) and extracted with EtOAc (20 mL×2). The combined organic phase was washed with brine (10 mL), dried over Na₂SO₄, filtered and concentrated to give the crude product. The crude product was purified by Prep-HPLC (Waters Xbridge (150 mm×25 mm, 10 μm) A=H₂O (10 mM NH₄HCO₃) and B=CH₃CN; 65-95% B over 7 minutes) to give the product (106.57 mg, 0.26 mmol, 58% yield) as a solid. $^1$H NMR (400 MHz, CDCl₃) 8.57 (d, 1H), 8.35 (d, 1H), 8.08 (dd, 1H), 7.73 (d, Synthesis of A47: To a solution of 1,1,1-trifluoro-2-methyl-propan-2-ol (2.18 g, 17.05 mmol) in THF (20 mL) was added NaH (0.68 g, 17.05 mmol, 60% in oil). The mixture was stirred at 25° C. for 1 hour. Then 5-bromo-2-fluoro-pyridine (3.0 g, 17.05 mmol) was added and the mixture was stirred at 80° C. for 16 hours. After cooling to room temperature, the reaction was quenched with H₂O (20 mL), concentrated and diluted with H₂O (20 mL), then extracted with EtOAc (20 mL×3). The combined organic phase was washed with brine (30 mL), dried over Na₂SO₄, filtered and concentrated to give the crude product. The crude product was purified with flash chromatography on silica gel (EtOAc in PE=0% to 10%) to give the product (2.0 g, 5.98 mmol) as an oil. LCMS R$_t$=1.46 min in 2.0 min chromatography, 10-80AB, MS ESI calcd. for C₉H₁₀BrF₃NO [M+H]⁺ 284.0, found 283.8.

Synthesis of A48: A mixture of 5-bromo-2-(2,2,2-trifluoro-1,1-dimethyl-ethoxy)pyridine (2.0 g, 7.04 mmol), 4,4, 5,5-tetramethyl-2-(4,4,5,5-tetramethyl-1,3,2-dioxaborolan-2-yl)-1,3,2-dioxaborolane (2681.8 mg, 10.56 mmol), KOAc (1381.91 mg, 14.08 mmol) and Pd(dppf)Cl$_2$ (515.15 mg, 0.70 mmol) in 1,4-dioxane (40 mL) was stirred at 85° C. for 16 hours under a N$_2$ atmosphere. After cooling to room temperature, the reaction mixture was concentrated and diluted with H$_2$O (20 mL), then extracted with EtOAc (30 mL×3). The combined organic phase was washed with brine (40 mL), dried over Na$_2$SO$_4$, filtered and concentrated to give the crude product. The crude product was purified with flash chromatography on silica gel (EtOAc in PE=0% to 2%) to give the impure product (3.4 g, 7.33 mmol) as an oil. $^1$H NMR (CDCl$_3$, 400 MHz) δ=8.43 (d, 1H), 7.86 (m, 1H), 6.66 (d, 1H), 1.74 (s, 6H), 1.26 (s, 12H).

Synthesis of Compound 35: A mixture of 6-chloro-3-(trifluoromethyl)-[1,2,4]triazolo[4,3-a]pyrazine (100 mg, 0.45 mmol), 5-(4,4,5,5-tetramethyl-1,3,2-dioxaborolan-2-yl)-2-(2,2,2-trifluoro-1,1-dimethyl-ethoxy)pyridine (297.57 mg, 0.54 mmol), Pd(dppf)Cl$_2$ (49.31 mg, 0.07 mmol), Cs$_2$CO$_3$ (292.77 mg, 0.90 mmol) in 1,4-dioxane (10 mL) and water (1 mL) was stirred at 90° C. for 16 hours. After cooling to room temperature, the reaction mixture was concentrated and diluted with H$_2$O (20 mL), and then extracted with DCM (30 mL×3). The combined organic phase was washed with brine (30 mL), dried over Na$_2$SO$_4$, filtered and concentrated to give the crude product. The crude product was purified by prep-HPLC (Boston Prime C18 (150 mm×30 mm, 5 μm) A=H$_2$O (0.05% NH$_4$OH) and B=CH$_3$CN; 17-47% B over 8 min) to give the product (37.13 mg, 0.09 mmol, 21% yield) as a solid. $^1$H NMR (400 MHz, CDCl$_3$) δ$_H$=9.61 (d, 1H), 8.76 (d, 1H), 8.39 (s, 1H), 8.21 (dd, 1H), 6.96 (d, 1H), 1.89 (s, 6H). LCMS R$_t$=1.34 min in 2.0 min chromatography, 10-80AB, MS ESI calcd. for C$_{15}$H$_{12}$F$_6$N$_5$O [M+H]$^+$ 392.1, found 392.0.

Example 36: 3-(trifluoromethyl)-6-[6-[(1R)-2,2,2-trifluoro-1-methyl-ethoxy]-3-pyridyl]-[1,2,4]triazolo[4,3-a]pyrazine

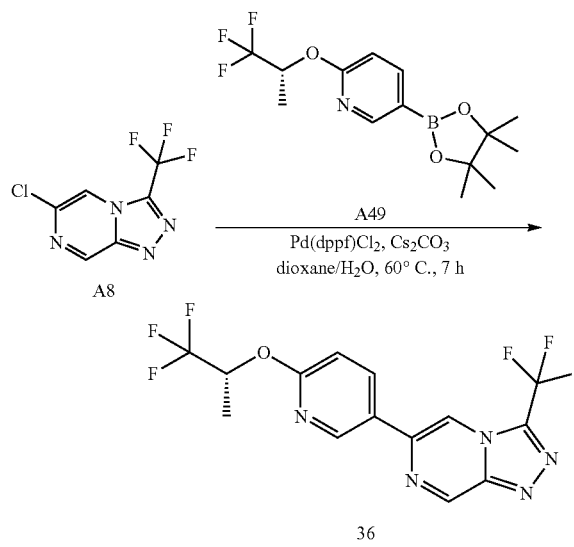

A mixture of 6-chloro-3-(trifluoromethyl)-[1,2,4]triazolo[4,3-a]pyrazine (300 mg, 1.35 mmol), 5-(4,4,5,5-tetramethyl-1,3,2-dioxaborolan-2-yl)-2-[(1R)-2,2,2-trifluoro-1-methyl-ethoxy]pyridine (512.94 mg, 1.62 mmol), Pd(dppf)Cl$_2$ (147.94 mg, 0.20 mmol) and Cs$_2$CO$_3$ (878.32 mg, 2.7 mmol) in 1,4-dioxane (20 mL) and water (2 mL) was stirred at 60° C. for 7 hours under N$_2$. After cooling to room temperature, the mixture was diluted with H$_2$O (30 mL), and then extracted with EtOAc (30 mL×2). The combined organic phase was washed with water (30 mL) and brine (30 mL), dried over Na$_2$SO$_4$, filtered and concentrated to give the crude product. The crude product was purified by flash chromatography on silica gel (EtOAc in PE=0% to 10% to 30%) to give the product (167.8 mg, 444.9 μmol, 33% yield) as a solid. $^1$H NMR (400 MHz, CDCl$_3$) δ$_H$=9.60 (d, 1H), 8.75 (s, 1H), 8.38 (s, 1H), 8.27-8.17 (m, 1H), 7.00 (d, 1H), 5.95-5.81 (m, 1H), 1.55 (d, 3H). LCMS R$_t$=1.27 min in 2.0 min chromatography, 10-80AB, MS ESI calcd. for C$_{14}$H$_{10}$F$_6$N$_5$O [M+H]$^+$ 378.1, found 378.0.

Example 37: 3-(trifluoromethyl)-6-[6-[(1S)-2,2,2-trifluoro-1-methyl-ethoxy]-3-pyridyl]-[1,2,4]triazolo[4,3-a]pyrazine

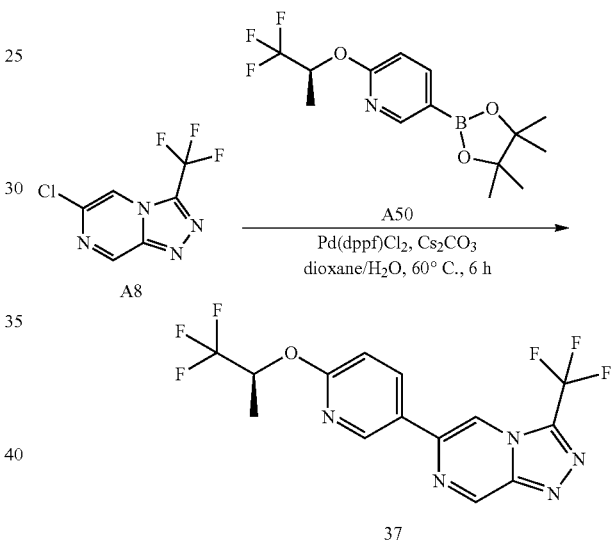

A mixture of 6-chloro-3-(trifluoromethyl)-[1,2,4]triazolo[4,3-a]pyrazine (400 mg, 1.8 mmol), 5-(4,4,5,5-tetramethyl-1,3,2-dioxaborolan-2-yl)-2-[(1S)-2,2,2-trifluoro-1-methyl-ethoxy]pyridine (683.92 mg, 2.16 mmol), Pd(dppf)Cl$_2$ (197.26 mg, 0.27 mmol) and Cs$_2$CO$_3$ (1.17 g, 3.59 mmol) in 1,4-dioxane (5 mL) and water (0.50 mL) was stirred at 60° C. for 6 hours under N$_2$. After cooling to room temperature, the mixture was filtered through Celite, and eluted with EtOAc (5 mL×2), and the filtrate was diluted with sat. NH$_4$Cl (30 mL). The mixture was extracted with EtOAc (20 mL×2), and the combined organic phase was washed with water (50 mL) and brine (50 mL), dried over Na$_2$SO$_4$, filtered and concentrated to give the crude product. The crude product was purified by flash chromatography on silica gel (EtOAc in PE=0% to 50%), then triturated from n-hexane/DCM (10:1, 6 mL) to give the product (283.61 mg, 0.74 mmol, 41% yield) as a solid. $^1$H NMR (400 MHz, CDCl$_3$)$^{δH}$=9.60 (d, 1H), 8.78-8.73 (m, 1H), 8.38 (d, 1H), 8.23 (dd, 1H), 7.00 (dd, 1H), 5.94-5.83 (m, 1H), 1.55 (d, 3H). LCMS R$_t$=1.27 min in 2.0 min chromatography, 10-80AB, MS ESI calcd. for C$_{14}$H$_{10}$F$_6$N$_5$O [M+H]$^+$ 378.1, found 378.1.

Example 38: 6-[5-fluoro-6-[(1S)-2,2,2-trifluoro-1-methyl-ethoxy]-3-pyridyl]-5-methyl-3-(trifluoromethyl)-[1,2,4]triazolo[4,3-a]pyrazine

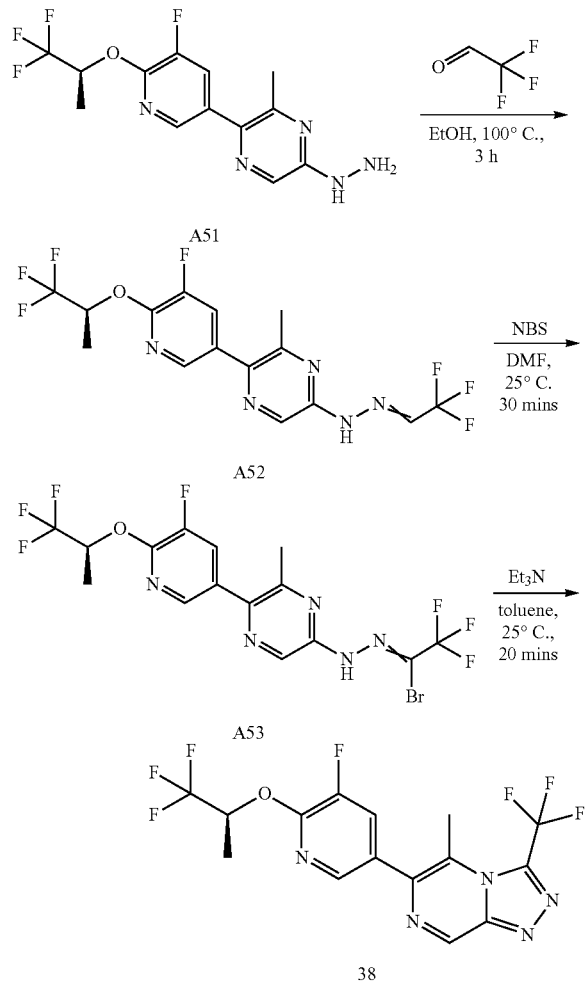

Synthesis of A52: A mixture of [5-[5-fluoro-6-[(1S)-2,2,2-trifluoro-1-methyl-ethoxy]-3-pyridyl]-6-methyl-pyrazin-2-yl]hydrazine (200 mg, 0.60 mmol) and 2,2,2-trifluoroacetaldehyde (1 mL, 0.60 mmol, 75% wt) in ethanol (1 mL) was stirred at 100° C. for 3 hours. After cooling to room temperature, the mixture was concentrated under reduced pressure. The residue was diluted with H$_2$O (20 mL) and extracted with EtOAc (20 mL). The combined organic phase was washed with brine (10 mL), dried over anhydrous Na$_2$SO$_4$, filtered and concentrated to afford a crude product (300 mg, 0.73 mmol) as an oil. LCMS R$_t$=0.97 min in 1.5 min chromatography, 5-95AB, MS ESI calcd. for C$_{15}$H$_{13}$F$_7$N$_5$O [M+H]$^+$ 412.0, found 412.0.

Synthesis of A53: To a solution of 5-[5-fluoro-6-[(1S)-2,2,2-trifluoro-1-methyl-ethoxy]-3-pyridyl]-6-methyl-N-(2,2,2-trifluoroethylideneamino)pyrazin-2-amine (300 mg, 0.73 mmol) in DMF (3 mL) was added NBS (142.81 mg, 0.80 mmol). The mixture was stirred at 25° C. for 30 min. The mixture was diluted with EtOAc (20 mL) and washed with H$_2$O (10 mL×2) and brine (20 mL), dried over anhydrous Na$_2$SO$_4$, filtered and concentrated to give a crude product (400 mg, 0.31 mmol) as an oil. LCMS R$_t$=1.04 min in 1.5 min chromatography, 5-95AB, MS ESI calcd. for C$_{15}$H$_{12}$BrF$_7$N$_5$O [M+H+2]$^+$492.0, found 492.0.

Synthesis of Compound 38: To a solution of 2,2,2-trifluoro-N-[5-[5-fluoro-6-[(1S)-2,2,2-trifluoro-1-methyl-ethoxy]-3-pyridyl]-6-methyl-pyrazin-2-yl]ethanehydrazonoyl bromide (400 mg, 0.82 mmol) in toluene (4 mL) was added Et$_3$N (0.56 mL, 4.08 mmol). The mixture was stirred at 25° C. for 20 min. The mixture was diluted with EtOAc (20 mL) and washed with H$_2$O (20 mL) and brine (20 mL), dried over anhydrous Na$_2$SO$_4$, filtered and concentrated. The crude product was purified by flash chromatography on silica gel (EtOAc in PE=0% to 30% to 50%) and by prep-TLC (silica gel, PE:EtOAc=2:1) to give the product (35.6 mg, 0.09 mmol, 11% yield) as an oil. $^1$H NMR (400 MHz, CDCl$_3$) δ$_H$=9.47 (s, 1H), 8.11 (d, 1H), 7.70 (dd, 1H), 5.95-5.83 (m, 1H), 2.89 (s, 3H), 1.61 (d, 3H). LCMS R$_t$=1.25 min in 2 min chromatography, 10-80AB, MS ESI calcd. for C$_{15}$H$_{11}$F$_7$N$_5$O [M+H]$^+$ 410.1, found 409.9.

Example 39: 6-[5-fluoro-6-[(1R)-2,2,2-trifluoro-1-methyl-ethoxy]-3-pyridyl]-5-methyl-3-(trifluoromethyl)-[1,2,4]triazolo[4,3-a]pyrazine

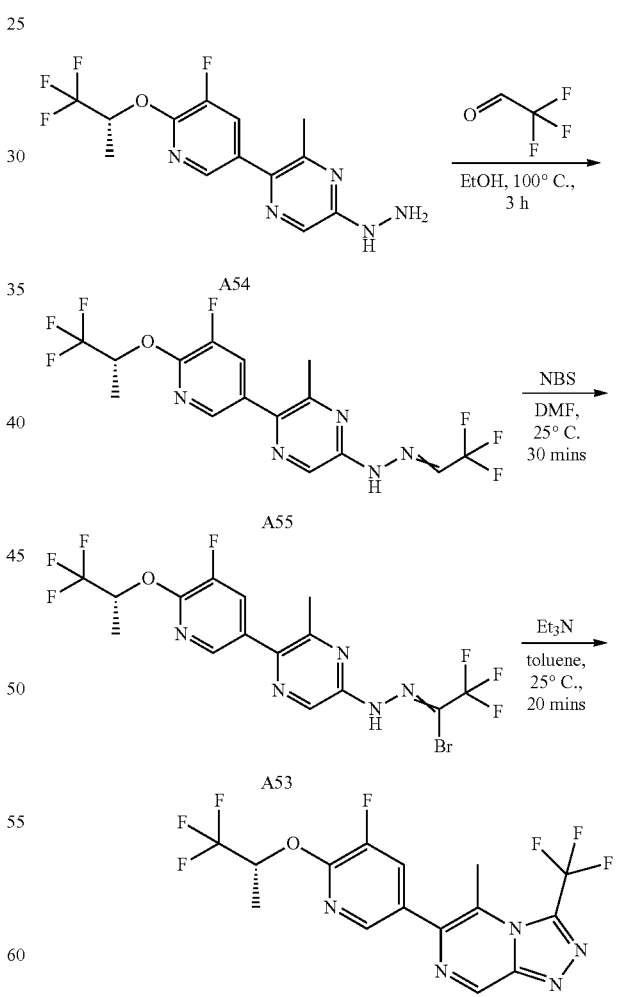

Synthesis of A55: A mixture of [5-[5-fluoro-6-[(1R)-2,2,2-trifluoro-1-methyl-ethoxy]-3-pyridyl]-6-methyl-pyrazin-2-yl]hydrazine (280 mg, 0.85 mmol) and 2,2,2-trifluoroacetaldehyde (110.47 mg, 0.85 mmol) in ethanol (1 mL) was stirred at 100° C. for 3 hours. After cooling to room temperature, the mixture was diluted with EtOAc (20 mL) and washed with $H_2O$ (10 mL) and brine (10 mL), dried over anhydrous $Na_2SO_4$, filtered and concentrated to give the crude product (350 mg, 0.75 mmol) as an oil. LCMS $R_t$=0.97 min in 1.5 min chromatography, 5-95AB, MS ESI calcd. for $C_{15}H_{13}F_7N_5O$ $[M+H]^+$ 412.1, found 412.2.

Synthesis of A56: To a solution of 5-[5-fluoro-6-[(1R)-2,2,2-trifluoro-1-methyl-ethoxy]-3-pyridyl]-6-methyl-N-(2,2,2-trifluoroethylideneamino)pyrazin-2-amine (350 mg, 0.85 mmol) in DMF (5 mL) was added NBS (166.61 mg, 0.94 mmol). The mixture was stirred at 25° C. for 30 min. The mixture was diluted with EtOAc (50 mL), washed with $H_2O$ (10×2 mL) and brine (20 mL), dried over anhydrous $Na_2SO_4$, filtered and concentrated to give the crude product (420 mg, 0.79 mmol) as an oil. LCMS $R_t$=1.06 min in 1.5 min chromatography, 5-95AB, MS ESI calcd. for $C_{15}H_{12}BrF_7N_5O$ $[M+H+2]^+$ 492.0, found 492.1.

Synthesis of Compound 39: To a solution of 2,2,2-trifluoro-N-[5-[5-fluoro-6-[(1R)-2,2,2-trifluoro-1-methyl-ethoxy]-3-pyridyl]-6-methyl-pyrazin-2-yl]ethanehydrazonoyl bromide (420 mg, 0.86 mmol) in toluene (3 mL) was added $Et_3N$ (0.59 mL, 4.28 mmol). The mixture was stirred at 25° C. for 30 min. The mixture was diluted with EtOAc (30 mL), washed with $H_2O$ (20 mL) and brine (20 mL), dried over anhydrous $Na_2SO_4$, filtered and concentrated. The crude product was purified by prep-TLC (silica gel, PE:EtOAc=10:1) to give partially purified product. The impure product was further purified by prep-HPLC [Boston Prime C18 (150 mm×30 mm, 5 μm) A=$H_2O$ (0.05% $NH_4OH$) and B=$CH_3CN$; 50-70% B over 9 min)] to give the product (97.00 mg, 0.24 mmol, 28% yield) as a solid. $^1H$ NMR (400 MHz, $CDCl_3$)$^{\delta H}$=9.47 (s, 1H), 8.12 (d, 1H), 7.70 (dd, 1H), 5.97-5.85 (m, 1H), 2.89 (s, 3H), 1.62-1.60 (m, 3H). LCMS $R_t$=1.30 min in 2.0 min chromatography, 10-80AB, MS ESI calcd. for $C_{15}H_{11}F_7N_5O$ $[M+H]^+$ 410.1, found 410.1.

Example 40: 6-[5-fluoro-6-(2,2,2-trifluoro-1,1-dimethyl-ethoxy)-3-pyridyl]-7-methyl-3-(trifluoromethyl)-[1,2,4]triazolo[4,3-b]pyridazine

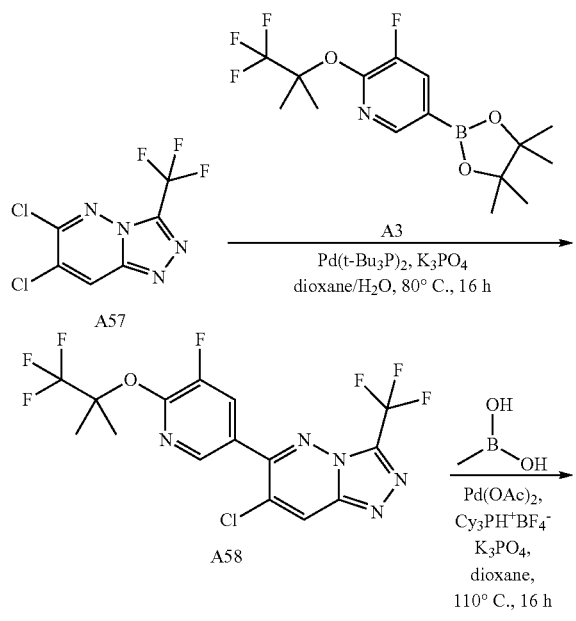

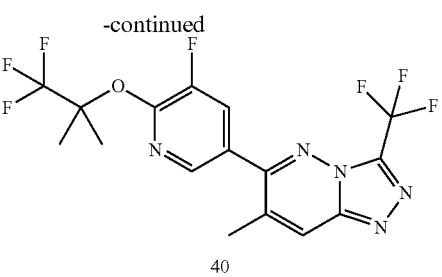

Synthesis of A58: A mixture of 6,7-dichloro-3-(trifluoromethyl)-[1,2,4]triazolo[4,3-b]pyridazine (300 mg, 1.17 mmol) and [5-fluoro-6-(2,2,2-trifluoro-1,1-dimethyl-ethoxy)-3-pyridyl]boronic acid (280.5 mg, 1.05 mmol) and $K_3PO_4$ (495.64 mg, 2.33 mmol) and $Pd(t-Bu_3P)_2$ (89.48 mg, 0.18 mmol) in 1,4-dioxane (15 mL) and water (1.5 mL) was stirred at 80° C. under $N_2$ for 16 hours to give a suspension. After cooling to room temperature, the mixture was filtered through Celite. The filtrate was concentrated, and the residue was diluted with water (20 mL) and extracted with EtOAc (20 mL×2). The combined organic layer was washed with water (10 mL×2) and brine (15 mL×2), dried over anhydrous $Na_2SO_4$, filtered and concentrated. The crude product was purified by flash chromatography on silica gel (EtOAc in PE=0% to 5% to 10%) to give the product (100 mg, 146.9 μmol, 13% yield) as an oil. LCMS $R_t$=0.97 min in 1.5 min chromatography, 5-95AB, MS ESI calcd. for $C_{15}H_{10}ClF_7N_5O$ $[M+H]^+$ 444.1, found 444.1.

Synthesis of Compound 40: A mixture of 7-chloro-6-[5-fluoro-6-(2,2,2-trifluoro-1,1-dimethyl-ethoxy)-3-pyridyl]-3-(trifluoromethyl)-[1,2,4]triazolo[4,3-b]pyridazine (100 mg, 0.23 mmol) and methylboronic acid (269.82 mg, 4.51 mmol) and $K_3PO_4$ (0.48 g, 2.25 mmol) and $Cy_3PH^+BF_4^-$ (41.5 mg, 0.11 mmol) and $Pd(OAc)_2$ (10.12 mg, 0.05 mmol) in 1,4-dioxane (10 mL) was stirred at 110° C. for 16 hours under $N_2$. After cooling to room temperature, the mixture was diluted with $H_2O$ (30 mL) and the aqueous layer was extracted with EtOAc (50 mL×2). The combined organic phase was washed with water (20 mL×2) and brine (20 mL), dried over anhydrous $Na_2SO_4$, filtered and concentrated. The crude product was purified by prep-TLC (silica gel, PE:EtOAc=3:1) to give the impure product. Analytical SFC: (Daicel CHIRALCEL OD-3 (150 mm×4.6 mm, 3 μm), Mobile phase: A: $CO_2$, B: ethanol (0.05% DEA), Gradient: from 5% to 40% of B in 5 min and hold 40% of B for 0.5 min, then 5% of B for 1.5 min. Flow rate: 2.5 mL/min, Column temp: 35° C.) showed two peaks at 3.10 min (84.5%) and 4.25 min (14.7%).

The product was purified by SFC (Daicel CHIRALCEL OD-H (250 mm×30 mm, 5 μm); A=$CO_2$ and B=EtOH (0.1% $NH_3 \cdot H_2O$); 35° C.; 60 mL/min; 30% B; 8 min run; 7 injections, Rt of peak 1=4.5 min) to give the product (12.66 mg, 29.8 μmol, 13% yield) as a solid. $^1H$ NMR (400 MHz, $CDCl_3$) $\delta_H$=8.18 (d, 1H), 8.13 (s, 1H), 7.64 (dd, 1H), 2.54 (s, 3H), 1.93 (s, 6H). LCMS $R_t$=1.26 min in 2.0 min chromatography, 10-80AB, MS ESI calcd. for $C_{16}H_{13}F_7N_5O$ $[M+H]^+$ 424.1, found 423.9.

Example 41: 7-chloro-6-[5-fluoro-6-(2,2,2-trifluoro-1,1-dimethyl-ethoxy)-3-pyridyl]-3-(trifluoromethyl)-[1,2,4]triazolo[4,3-b]pyridazine

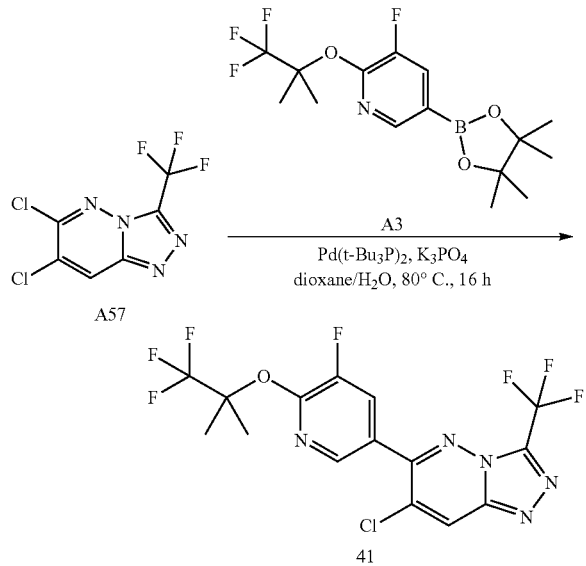

A mixture of 6,7-dichloro-3-(trifluoromethyl)-[1,2,4]triazolo[4,3-b]pyridazine (100 mg, 0.39 mmol) and [5-fluoro-6-(2,2,2-trifluoro-1,1-dimethyl-ethoxy)-3-pyridyl]boronic acid (93.5 mg, 0.35 mmol) and $K_3PO_4$ (165.21 mg, 0.78 mmol) and $Pd(t-Bu_3P)_2$ (29.83 mg, 0.06 mmol) in 1,4-dioxane (15 mL) and water (1.5 mL) was stirred at 80° C. under $N_2$ for 16 hours. After cooling to room temperature, the mixture was filtered through Celite. The filtrate was concentrated under reduced pressure. The residue was diluted with water (20 mL) and the aqueous layer was extracted with EtOAc (20 mL×2). The combined organic layer was washed with water (10 mL×2) and brine (15 mL×2), dried over anhydrous $Na_2SO_4$, filtered and concentrated. The crude product was purified by flash chromatography on silica gel (EtOAc in PE=0% to 5% to 10%) to give the impure product. The impure product was further purified by prep-HPLC [(Waters XBridge (150 mm×25 mm, 5 μm) A=$H_2O$ (10 mM $NH_4HCO_3$) and B=$CH_3CN$; 55-81% B over 8 min)] to give the product (26.5 mg, 59.8 μmol, 15% yield) as an oil. $^1H$ NMR (400 MHz, $CDCl_3$) $\delta_H$=8.41 (s, 1H), 8.34 (d, 1H), 7.80 (dd, 1H), 1.92 (s, 6H). LCMS $R_t$=1.37 min in 2.0 min chromatography, 10-80AB, MS ESI calcd. for $C_{15}H_{10}ClF_7N_5O$ [M+H]$^+$ 444.0, found 444.0.

Example 42: 7-chloro-6-[5-fluoro-6-[(1R)-2,2,2-trifluoro-1-methyl-ethoxy]-3-pyridyl]-3-(trifluoromethyl)-[1,2,4]triazolo[4,3-b]pyridazine

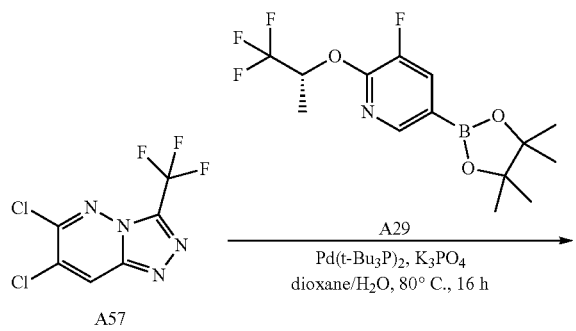

-continued

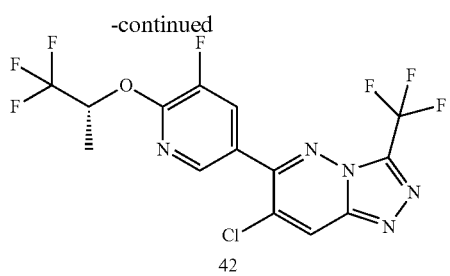

A mixture of 6,7-dichloro-3-(trifluoromethyl)-[1,2,4]triazolo[4,3-b]pyridazine (300 mg, 1.17 mmol) and (R)-3-fluoro-5-(4,4,5,5-tetramethyl-1,3,2-dioxaborolan-2-yl)-2-((1,1,1-trifluoropropan-2-yl)oxy)pyridine (265.76 mg, 1.05 mmol) and $K_3PO_4$ (495.64 mg, 2.33 mmol) and $Pd(t-Bu_3P)_2$ (89.48 mg, 0.18 mmol) in 1,4-dioxane (15 mL) and water (1.5 mL) was stirred at 80° C. under $N_2$ for 16 hours. After cooling to room temperature, the mixture was filtered through Celite. The filtrate was concentrated under reduced pressure. The residue was diluted with water (20 mL) and the aqueous layer was extracted with EtOAc (20 mL×2). The combined organic layer was washed with water (10 mL×2) and brine (15 mL×2), dried over anhydrous $Na_2SO_4$, filtered and concentrated. The crude product was purified by chromatography flash column on silica gel (EtOAc in PE=0% to 5% to 10%) to give the impure product. The impure product was further purified by prep-TLC (silica gel, PE:EtOAc=3:1) to give the product (25.24 mg, 58.2 μmol, 5% yield) as an oil. $^1H$ NMR (400 MHz, $CDCl_3$) $\delta_H$=8.42 (s, 1H), 8.36 (d, 1H), 7.84 (dd, 1H), 5.97-5.88 (m, 1H), 1.62 (d, 3H). LCMS $R_t$=1.33 min in 2.0 min chromatography, 10-80AB, MS ESI calcd. for $C_{14}H_8ClF_7N_5O$ [M+H]$^+$ 430.0, found 430.0.

Example 43: 7-chloro-6-[5-fluoro-6-[(1S)-2,2,2-trifluoro-1-methyl-ethoxy]-3-pyridyl]-3-(trifluoromethyl)-[1,2,4]triazolo[4,3-b]pyridazine

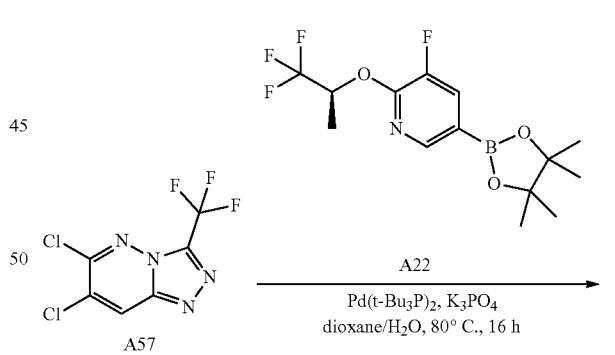

A mixture of 6,7-dichloro-3-(trifluoromethyl)-[1,2,4]triazolo[4,3-b]pyridazine (300 mg, 1.17 mmol) and (S)-3-fluoro-5-(4,4,5,5-tetramethyl-1,3,2-dioxaborolan-2-yl)-2-

((1,1,1-trifluoropropan-2-yl)oxy)pyridine (265.76 mg, 1.05 mmol) and $K_3PO_4$ (495.64 mg, 2.33 mmol) and $Pd(t-Bu_3P)_2$ (89.48 mg, 0.18 mmol) in 1,4-dioxane (15 mL) and water (1.5 mL) was stirred at 80° C. under $N_2$ for 16 hours. After cooling to room temperature, the mixture was filtered through Celite. The filtrate was concentrated under reduced pressure. The residue was diluted with water (20 mL) and extracted with EtOAc (20 mL×2). The combined organic layer was washed with water (10 mL×2) and brine (15 mL×2), dried over anhydrous $Na_2SO_4$, filtered and concentrated. The crude product was purified by flash chromatography on silica gel (EtOAc in PE=0% to 5% to 10%) to give the impure product (150 mg). 50 mg of the impure product was further purified by prep-HPLC [(Boston Green ODS (150 mm×30 mm, 5 μm); A=$H_2O$ (0.075% TFA) and B=$CH_3CN$; 63-93% B over 8 min)]. The fractions were combined, basified with saturated $NaHCO_3$ solution (10 mL), extracted with EtOAc (10 mL) and concentrated to give the product (26.05 mg, 60.6 mmol, 5% yield) as an oil. $^1$H NMR (400 MHz, $CDCl_3+D_2O$) $\delta_H$=8.42 (s, 1H), 8.36 (d, 1H), 7.84 (d, 1H), 5.96-5.85 (m, 1H), 1.62 (d, 3H). LCMS $R_t$=1.33 min in 2.0 min chromatography, 10-80AB, MS ESI calcd. for $C_{14}H_8ClF_7N_5O$ [M+H]$^+$ 430.0, found 430.0.

Example 44: (S)-6-(5-fluoro-6-((1,1,1-trifluoropropan-2-yl)oxy)pyridin-3-yl)-7-methyl-3-(trifluoromethyl)-[1,2,4]triazolo[4,3-b]pyridazine

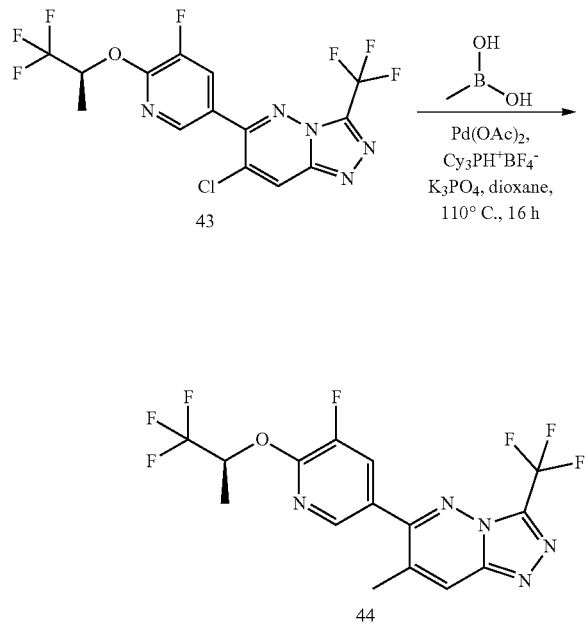

A mixture of (S)-7-chloro-6-(5-fluoro-6-((1,1,1-trifluoropropan-2-yl)oxy)pyridin-3-yl)-3-(trifluoromethyl)-[1,2,4]triazolo[4,3-b]pyridazine (100 mg, 0.23 mmol), methylboronic acid (269.82 mg, 4.51 mmol), $K_3PO_4$ (478.47 mg, 2.25 mmol), $Cy_3PH^+BF_4^-$ (41.5 mg, 0.11 mmol) and $Pd(OAc)_2$ (10.12 mg, 0.05 mmol) in 1,4-dioxane (10 mL) was stirred at 110° C. for 16 hours under $N_2$. After cooling to room temperature, the mixture was diluted with $H_2O$ (30 mL) and the aqueous layer was extracted with EtOAc (50 mL×2). The combined organic phase was washed with water (20 mL×2) and brine (20 mL), dried over anhydrous $Na_2SO_4$, filtered and concentrated. The crude product was purified by prep-TLC (silica gel, PE:EtOAc=3:1) to give the impure product. Analytical SFC: (Daicel CHIRALCEL OD-3 (150 mm×4.6 mm, 3 μm), Mobile phase: A: $CO_2$ B: ethanol (0.05% DEA), Gradient: from 5% to 40% of B over 5 min and hold 40% of B for 2.5 min, then 5% of B for 1.5 min, Flow rate: 2.5 mL/min, Column temp: 35° C.) showed two main peaks at Rt=3.03 min (89.8%) and Rt=4.04 min (10.3%). The product was purified by SFC (Daicel CHIRALCEL OD-H (250 mm×30 mm, 5 μm); A=$CO_2$ and B=MeOH (0.1% $NH_3 \cdot H_2O$); 38° C.; 50 mL/min; 30% B; 8 min run; 3 injections, Rt of peak 1=5.0 min) to give the product (9.35 mg, 22.8 mmol, 10% yield) as a solid. $^1$H NMR (400 MHz, $CDCl_3$) $\delta_H$=8.19 (d, 1H), 8.12 (d, 1H), 7.67 (dd, 1H), 5.98-5.84 (m, 1H), 2.53 (d, 3H), 1.62 (d, 3H). LCMS $R_t$=1.30 min in 2.0 min chromatography, 10-80AB, MS ESI calcd. for $C_{15}H_{11}F_7N_5O$ [M+H]$^+$ 410.1, found 410.0.

Example 45: (R)-6-(5-fluoro-6-((1,1,1-trifluoropropan-2-yl)oxy)pyridin-3-yl)-7-methyl-3-(trifluoromethyl)-[1,2,4]triazolo[4,3-b]pyridazine

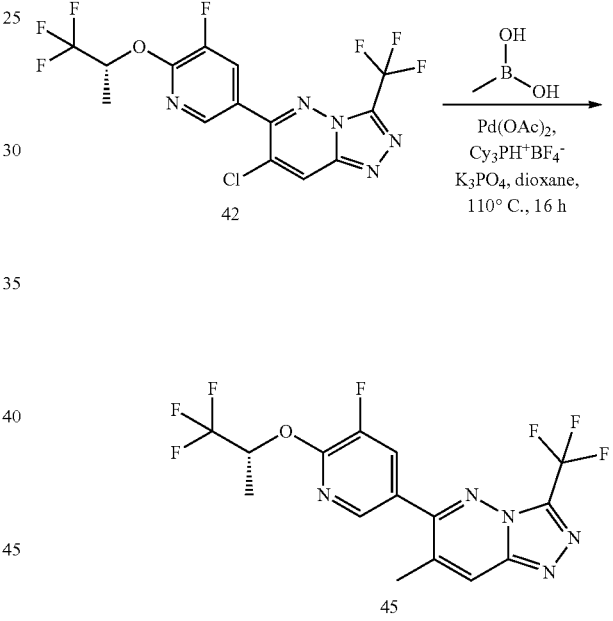

A mixture of (R)-7-chloro-6-(5-fluoro-6-((1,1,1-trifluoropropan-2-yl)oxy)pyridin-3-yl)-3-(trifluoromethyl)-[1,2,4] triazolo[4,3-b]pyridazine (140 mg, 0.32 mmol), methylboronic acid (377.74 mg, 6.31 mmol), $K_3PO_4$ (669.85 mg, 3.16 mmol), $Cy_3PH^+BF_4^-$ (58.09 mg, 0.16 mmol) and $Pd(OAc)_2$ (14.17 mg, 0.06 mmol) in 1,4-dioxane (10 mL) was stirred at 110° C. for 16 hours under $N_2$. After cooling to room temperature, the mixture was diluted with $H_2O$ (30 mL) and the aqueous layer was extracted with EtOAc (50 mL×2). The combined organic phase was washed with water (20 mL×2) and brine (20 mL), dried over anhydrous $Na_2SO_4$, filtered and concentrated. The crude product was purified by prep-TLC (silica gel, PE:EtOAc=3:1) to give the product (21.45 mg, 52.3 mmol, 16% yield) as a solid. $^1$H NMR (400 MHz, $CDCl_3$) $\delta_H$=8.19 (d, 1H), 8.12 (s, 1H), 7.67 (dd, 1H), 5.97-5.86 (m, 1H), 2.53 (s, 3H), 1.61 (d, 3H). LCMS $R_t$=1.30 min in 2.0 min chromatography, 10-80AB, MS ESI calcd. for $C_{15}H_{11}F_7N_5O$ [M+H]$^+$ 410.1, found 410.1.

Example 46: (S)-7-chloro-3-(trifluoromethyl)-6-(6-((1,1,1-trifluoropropan-2-yl)oxy)pyridin-3-yl)-[1,2,4]triazolo[4,3-b]pyridazine

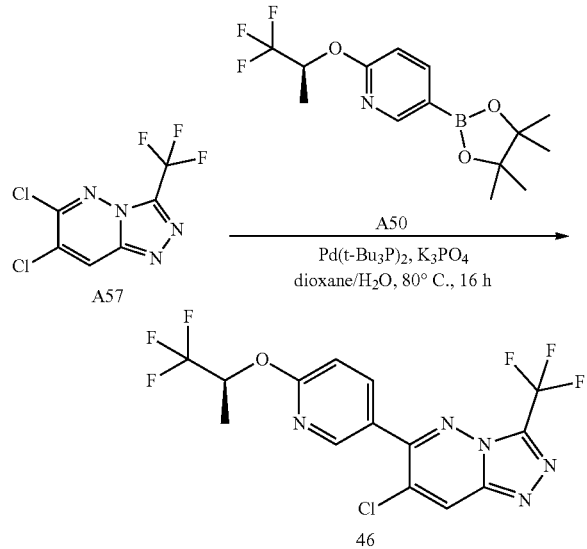

A mixture of 6,7-dichloro-3-(trifluoromethyl)-[1,2,4]triazolo[4,3-b]pyridazine (500 mg, 1.95 mmol), $K_3PO_4$ (826.07 mg, 3.89 mmol), Pd(t-$Bu_3P)_2$ (149.14 mg, 0.29 mmol) and 5-(4,4,5,5-tetramethyl-1,3,2-dioxaborolan-2-yl)-2-[(1S)-2,2,2-trifluoro-1-methyl-ethoxy]pyridine (616.95 mg, 1.95 mmol) in 1,4-dioxane (15 mL) and water (3 mL) was stirred at 80° C. under $N_2$ for 16 hours. After cooling to room temperature, the mixture was diluted with $NH_4Cl$ (30 mL), and the mixture was extracted with EtOAc (30 mL×2). The combined organic phase was washed with water (50 mL) and brine (50 mL), dried over $Na_2SO_4$, filtered and concentrated to give the crude product. The crude product was purified by flash chromatography on silica gel (EtOAc in PE=0% to 60% to 90%) to give the impure product, the impure product was purified by prep-TLC (silica gel, PE:EtOAc=1:1) to give the product (9.0 mg, 21.9 µmol, 9% yield) as a solid. $^1$H NMR (400 MHz, $CDCl_3$+$D_2O$) $\delta_H$=8.56 (d, 1H), 8.39 (s, 1H), 8.05 (dd, 1H), 7.01 (d, 1H), 5.93-5.85 (m, 1H), 1.57 (d, 3H). LCMS $R_t$=1.26 min in 2.0 min chromatography, 10-80AB, MS ESI calcd. for $C_{14}H_9ClF_6N_5O$ [M+H]$^+$ 412.0, found 411.8.

Example 47: (R)-7-chloro-3-(trifluoromethyl)-6-(6-((1,1,1-trifluoropropan-2-yl)oxy)pyridin-3-yl)-[1,2,4]triazolo[4,3-b]pyridazine

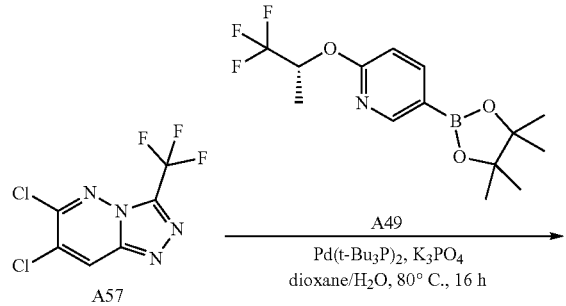

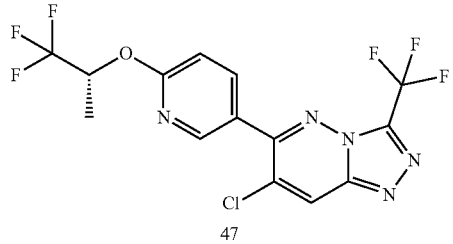

A mixture of 6,7-dichloro-3-(trifluoromethyl)-[1,2,4]triazolo[4,3-b]pyridazine (200 mg, 0.78 mmol), Pd(t-$Bu_3P)_2$ (59.66 mg, 0.12 mmol), (R)-5-(4,4,5,5-tetramethyl-1,3,2-dioxaborolan-2-yl)-2-((1,1,1-trifluoropropan-2-yl)oxy)pyridine (246.78 mg, 0.78 mmol) and $K_3PO_4$ (330.43 mg, 1.56 mmol) in 1,4-dioxane (15 mL) and water (3 mL) was stirred at 80° C. under $N_2$ for 16 hours. After cooling to room temperature, the mixture was filtered through Celite. The filtrate was concentrated to give a residue. The residue was diluted with water (20 mL), extracted with EtOAc (20 mL×2). The combined organic layer was washed with brine (15 mL×2), dried over anhydrous $Na_2SO_4$, filtered and concentrated to give the crude product. The crude product was purified by flash column chromatography on silica gel (EtOAc in PE=0% to 5% to 10%) to give the impure product. The impure product was purified by prep-TLC (silica gel, PE:EtOAc=3:1) and prep-HPLC (Waters XBridge (150 mm×25 mm, 5 µm) A=$H_2O$ (10 mM $NH_4HCO_3$) and B=$CH_3CN$; 50-80% B over 10 min) to give the product (21.21 mg, 0.05 mmol, 6% yield) as an oil. $^1$H NMR (400 MHz, $CDCl_3$) $\delta_H$=8.56 (d, 1H), 8.39 (s, 1H), 8.05 (dd, 1H), 7.01 (d, 1H), 5.90-5.82 (m, 1H), 1.56 (d, 3H). LCMS $R_t$=1.27 min in 2 min chromatography, 10-80AB, MS ESI calcd. for $C_{14}H_9ClF_6N_5O$ [M+H]$^+$ 412.0, found 411.9.

Example 48: (S)-7-methyl-3-(trifluoromethyl)-6-(6-((1,1,1-trifluoropropan-2-yl)oxy)pyridin-3-yl)-[1,2,4]triazolo[4,3-b]pyridazine

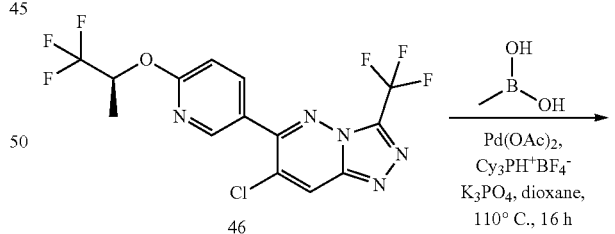

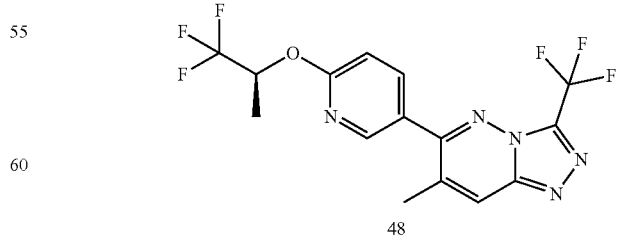

A mixture of (S)-7-chloro-3-(trifluoromethyl)-6-(6-((1,1,1-trifluoropropan-2-yl)oxy)pyridin-3-yl)-[1,2,4]triazolo[4,3-b]pyridazine (300 mg, 0.73 mmol), $Cy_3PH^+BF_4^-$ (134.17 mg, 0.36 mmol), K$_3$PO$_4$ (1.55 g, 7.29 mmol), Pd(OAc)$_2$ (32.72 mg, 0.15 mmol) and methylboronic acid (872.4 mg, 14.57 mmol) in 1,4-dioxane (10 mL) was stirred at 110° C. for 16 hours under N$_2$.

After cooling to room temperature, the mixture was diluted with H$_2$O (30 mL), and the mixture was extracted with EtOAc (30 mL×2). The combined organic phase was washed with water (50 mL) and brine (50 mL), dried over Na$_2$SO$_4$, filtered and concentrated to give the crude product. The crude product was purified by flash chromatography on silica gel (EtOAc in PE=0% to 40%) to give the impure product. Analytical SFC: The impure product was analyzed by SFC to show one main peak (Rt=3.06 min). Method: Column: Daicel CHIRALCEL OD-3 (150 mm×4.6 mm, 3 μm), Mobile phase: A: CO$_2$ B: ethanol (0.05% DEA), Gradient: from 5% to 40% of B over 5 min and hold 40% for 2.5 min, then 5% of B for 2.5 min, Flow rate: 2.5 mL/min, Column temp: 35° C., ABPR: 1500 psi. The product was purified by SFC (Daicel CHIRALCEL OD-H (250 mm×30 mm, 5 μm); A=CO$_2$ and B=0.1% NH$_3$·H$_2$O-EtOH; 38° C.; 60 mL/min; 25% B; 9 min run; 5 injections, Rt of peak 1=5.4 min) to give the product (36.1 mg, 92.1 μmol, 12% yield) as a solid. $^1$H NMR (400 MHz, CDCl$_3$) $\delta_H$=8.40 (d, 1H), 8.09 (d, 1H), 7.88 (dd, 1H), 7.01 (d, 1H), 5.88 (m, 1H), 2.51 (d, 3H), 1.56 (d, 3H). LCMS R$_t$=1.21 min in 2.0 min chromatography, 10-80AB, MS ESI calcd. for C$_{15}$H$_{12}$F$_6$N$_5$O [M+H]$^+$ 392.1, found 392.0.

Example 49: (R)-7-methyl-3-(trifluoromethyl)-6-(6-(((1,1,1-trifluoropropan-2-yl)oxy)pyridin-3-yl)-[1,2,4]triazolo[4,3-b]pyridazine

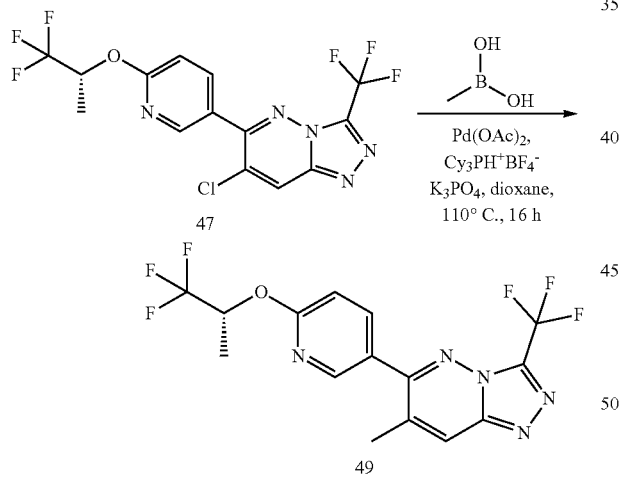

A mixture of (R)-7-chloro-3-(trifluoromethyl)-6-(6-(((1,1,1-trifluoropropan-2-yl)oxy)pyridin-3-yl)-[1,2,4]triazolo[4,3-b]pyridazine (260 mg, 0.63 mmol), Cy$_3$PH$^+$BF$_4^-$ (116.28 mg, 0.32 mmol), Pd(OAc)$_2$ (28.36 mg, 0.13 mmol), methylboronic acid (7756.08 mg, 12.63 mmol) and K$_3$PO$_4$ (11341.8 mg, 6.32 mmol) in 1,4-dioxane (10 mL) was stirred at 110° C. for 16 hours under N$_2$. After cooling to room temperature, the mixture was concentrated, and the mixture was diluted with H$_2$O (15 mL) and extracted with EtOAc (15 mL×2). The combined organic phase was washed with brine (20 mL), dried over Na$_2$SO$_4$, filtered and concentrated to give the crude product. The crude product was purified by flash chromatography on silica gel (EtOAc in PE=0% to 30% to 50%) to give the impure product. Analytical SFC: The impure product was analyzed by SFC (Daicel CHIRALCEL OJ-3 (150 mm×4.6 mm, 3 μm), Mobile phase: A: CO$_2$ B: ethanol (0.05% DEA), Gradient: from 5% to 40% of B over 5 min and from 40% to 5% of B over 0.5 min, hold 5% of B for 1.5 min, Flow rate: 2.5 mL/min Column temp: 35° C.) to show one main peaks at 1.81 min. The product was purified by SFC (Daicel CHIRALCEL OJ-H (250 mm×30 mm, 5 μm); A=CO$_2$ and B=0.1% NH$_3$·H$_2$O-EtOH; 38° C.; 50 mL/min; 10% B; 9 min run; 7 injections, Rt of peak 1=4.4 min) to give the product (10.06 mg, 0.03 mmol, 34% yield) as a solid. The ee % value was checked by SFC (Column: Daicel CHIRALPAK AS-H (250 mm×4.6 mm, 5 μm), Mobile phase: A: hexane (0.1% DEA) B: IPA Isocratic: A:B=90:10, Flow rate: 1 mL/min Column temp: 25° C.) to show ee=96.5%. $^1$H NMR (400 MHz, CDCl$_3$) $\delta_H$=8.40 (d, 1H), 8.10 (d, 1H), 7.87 (dd, 1H), 7.04-6.97 (m, 1H), 5.99-5.82 (m, 1H), 2.51 (d, 3H), 1.56 (d, 3H). LCMS R$_t$=1.32 min in 2 min chromatography, 10-80AB, MS ESI calcd. for C$_{15}$H$_{12}$F$_6$N$_5$O [M+H]$^+$ 392.1, found 392.0.

Example 50: 7-chloro-6-[6-(2,2,2-trifluoro-1,1-dimethyl-ethoxy)-3-pyridyl]-3-(trifluoromethyl)-[1,2,4]triazolo[4,3-b]pyridazine

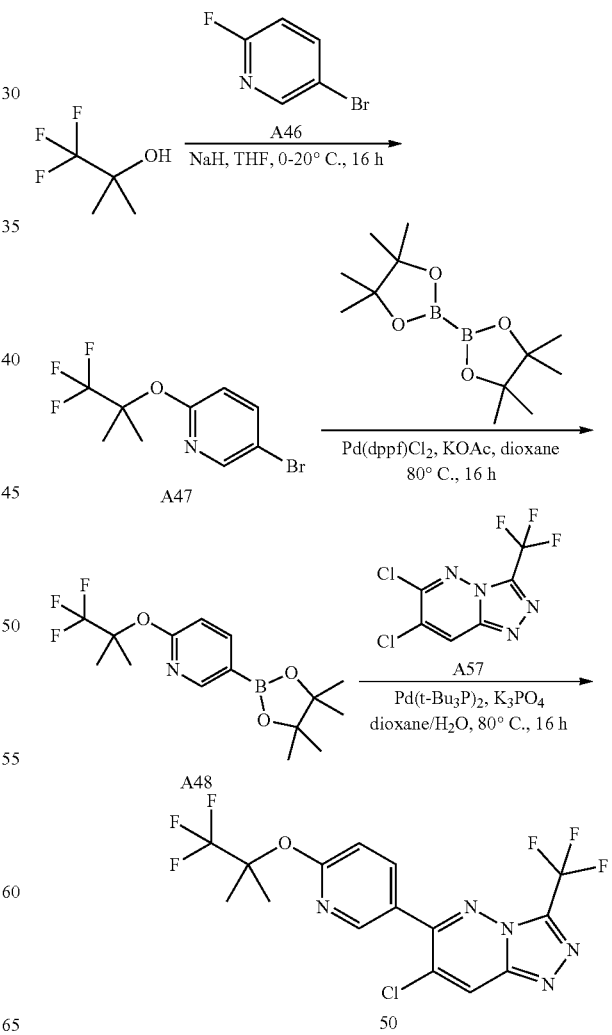

Synthesis of A47: To a solution of 1,1,1-trifluoro-2-methyl-propan-2-ol (41.81 g, 326.38 mmol) in THF (200 mL) was added NaH (19.55 g, 488.66 mmol, 60% in oil) slowly at 0° C. To the mixture was added 5-bromo-2-fluoropyridine (43 g, 244.33 mmol). The resulting mixture was stirred at 80° C. for 16 hours. The mixture was cooled to room temperature. Saturated NH$_4$Cl aqueous (100 mL) was added to the mixture. The mixture was concentrated to remove most of the THF and then extracted with EtOAc (100 mL×2). The combined organic phase was washed with brine (100 mL), dried over anhydrous Na$_2$SO$_4$, filtered and concentrated to give the crude product. The crude product was purified by chromatography flash column on silica gel (PE) to give the product (30.5 g, 107.37 mmol, 43% yield) as an oil. $^1$H NMR (CDCl$_3$ 400 MHz) $\delta_H$=8.18 (d, 1H), 7.67 (dd, 1H), 6.69 (d, 1H), 1.78 (s, 6H).

Synthesis of A48: A mixture of 5-bromo-2-(2,2,2-trifluoro-1,1-dimethyl-ethoxy)pyridine (30.5 g, 107.37 mmol), 4,4,5,5-tetramethyl-2-(4,4,5,5-tetramethyl-1,3,2-dioxaborolan-2-yl)-1,3,2-dioxaborolane (40.9 g, 161.05 mmol), KOAc (21.07 g, 214.74 mmol) and Pd(dppf)Cl$_2$ (7.86 g, 10.74 mmol) in 1,4-dioxane (150 mL) was stirred at 80° C. for 16 hours under N$_2$ atmosphere. The mixture was cooled to room temperature. The reaction was concentrated and diluted with H$_2$O (150 mL), then extracted with EtOAc (200 mL×3). The combined organic phase was washed with brine (150 mL), dried over Na$_2$SO$_4$, filtered and concentrated to give the crude product. The crude product was purified with flash chromatography on silica gel (EtOAc in PE=0% to 2%) to give the product (33.0 g, 79.73 mmol, 74% yield) as a solid. LCMS R$_t$=1.06 min in 1.5 min chromatography, 5-95AB, MS ESI calcd. for C$_{15}$H$_{22}$BF$_3$NO$_3$ [M+H]$^+$ 332.2, found 332.2.

Synthesis of Compound 50: A mixture of 6,7-dichloro-3-(trifluoromethyl)-[1,2,4]triazolo[4,3-b]pyridazine (455 mg, 1.77 mmol), 5-(4,4,5,5-tetramethyl-1,3,2-dioxaborolan-2-yl)-2-(2,2,2-trifluoro-1,1-dimethyl-ethoxy)pyridine (425.42 mg, 1.59 mmol), K$_3$PO$_4$ (751.72 mg, 3.54 mmol) and Pd(t-Bu$_3$P)$_2$ (135.72 mg, 0.27 mmol) in 1,4-dioxane (15 mL) and water (1.5 mL) was stirred at 80° C. under N$_2$ for 16 hours. The mixture was cooled to room temperature and filtered through Celite. The filtrate was concentrated to give a residue. The residue was diluted with H$_2$O (20 mL), extracted with EtOAc (20 mL×2). The combined organic layer was washed with H$_2$O (10 mL×2), brine (15 mL×2), dried over anhydrous Na$_2$SO$_4$, filtered and concentrated to give the crude product. The crude product was purified by flash column chromatography on silica gel (EtOAc in PE=0% to 5% to 10%) to give the impure product (170 mg). The impure product was further purified by prep-HPLC (Waters XBridge (150 mm×25 mm, 5 μm) A=H$_2$O (10 mM NH$_4$HCO$_3$) and B=CH$_3$CN; 50-80% B over 8 min) to give the product (38.75 mg, 91.0 μmol, 5% yield) as a colorless oil. $^1$H NMR (CDCl$_3$ 400 MHz) $\delta_H$=8.54 (d, 1H), 8.38 (s, 1H), 8.00 (dd, 1H), 6.94 (d, 1H), 1.90 (s, 6H). LCMS R$_t$=1.34 min in 2.0 min chromatography, 10-80AB, MS ESI calcd. for C$_{15}$H$_{11}$ClF$_6$N$_5$O [M+H]$^+$ 426.0, found 426.1.

Example 51: 7-methyl-6-[6-(2,2,2-trifluoro-1,1-dimethyl-ethoxy)-3-pyridyl]-3-(trifluoromethyl)-[1,2,4]triazolo[4,3-b]pyridazine

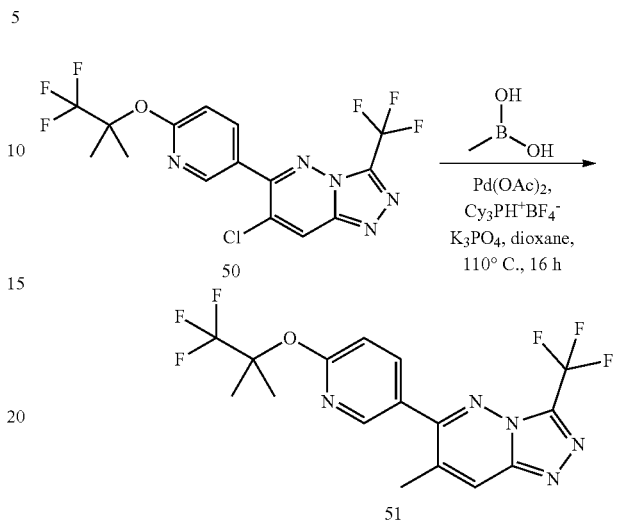

A mixture of 7-chloro-6-[5-fluoro-6-(2,2,2-trifluoro-1,1-dimethyl-ethoxy)-3-pyridyl]-3-(trifluoromethyl)-[1,2,4]triazolo[4,3-b]pyridazine (90 mg, 0.21 mmol), methylboronic acid (242.83 mg, 4.06 mmol), K$_3$PO$_4$ (430.62 mg, 2.03 mmol), Cy$_3$PH$^+$BF$_4^-$ (37.35 mg, 0.10 mmol) and Pd(OAc)$_2$ (9.11 mg, 0.04 mmol) in 1,4-dioxane (10 mL) was stirred at 110° C. for 16 hours under N$_2$. The mixture was cooled to room temperature. The mixture was diluted with H$_2$O (30 mL) and the mixture was extracted with EtOAc (50 mL×2). The combined organic phase was washed with water (20 mL×2) and brine (20 mL), dried over Na$_2$SO$_4$, filtered and concentrated to give a residue. The residue was purified by prep-TLC (silica gel, PE:EtOAc=3:1) to give the product. Analytical SFC: Analysis by SFC (Daicel CHIRALCEL OD-3 (150 mm×4.6 mm, 3 μm), Mobile phase: ethanol (0.05% DEA) in CO$_2$, Gradient: from 5% to 40% of B in 5 min and from 40% to 5% of B for 0.5 min, hold 5% of B for 1.5 min, Flow rate: 2.5 mL/min Column temp: 35° C.) showed the main peak (peak 1: Rt=3.08 min). The product was purified by SFC (Daicel CHIRALCEL OD-H (250 mm×30 mm, μm); A=CO$_2$ and B=0.1% NH$_3$·H$_2$O-EtOH; 38° C.; 60 mL/min; 30% B; 8 min run; 5 injections, Rt of peak 1=4.6 min) to give the product (27.1 mg, 66.9 μmol, 32% yield) as a solid. $^1$H NMR (CDCl$_3$ 400 MHz) $\delta_H$=8.38 (d, 1H), 8.09 (d, 1H), 7.82 (dd, 1H), 6.95 (d, 1H), 2.51 (d, 3H), 1.89 (s, 6H). LCMS R$_t$=1.31 min in 2.0 min chromatography, 10-80AB, MS ESI calcd. for C$_{16}$H$_{14}$F$_6$N$_5$O [M+H]$^+$ 406.1, found 406.1.

Example 52: 6-(6-(3,3-difluorocyclobutoxy)pyridin-3-yl)-3-(difluoromethyl)-[1,2,4]triazolo [4,3-a]pyrazine

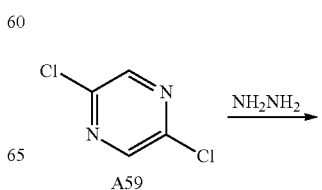

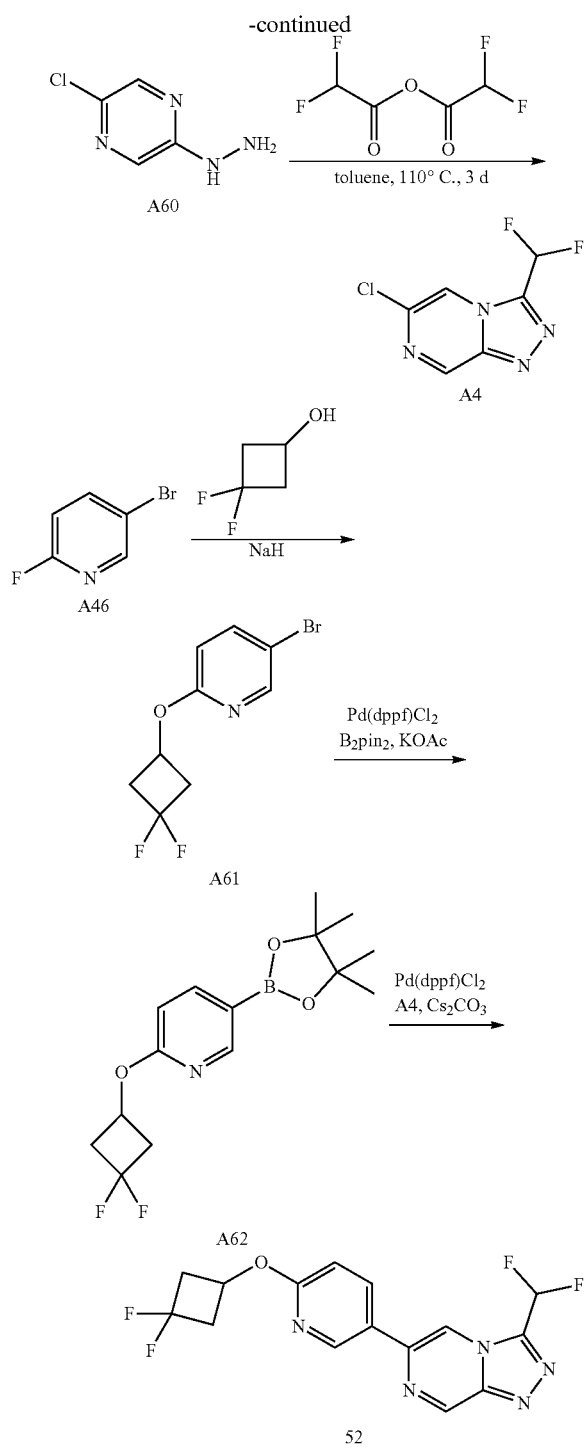

at room temperature. The reaction mixture was heated at 110° C. for 3 days. The reaction was cooled to room temperature and concentrated to give a residue. The residue was treated with water (30 mL) and extracted with ethyl acetate (2×30 mL). The organic layer was washed with brine (25 mL), dried over anhydrous $Na_2SO_4$ and concentrated. The crude product was purified by column chromatography on silica gel with 80% EtOAc/PE to afford the product (300 mg, 1.47 mmol, 7% yield). LCMS: 205.1 (M+H), Rt 1.31 min Column: ZORBAX XDB C-18 (50×4.6 mm), 3.5 μm Mobile Phase: A: 0.1% HCOOH in water:ACN (95:5), B: ACN; Flow Rate: 1.5 mL/min Synthesis of A61: To a stirred solution of 3,3-difluorocyclobutanol (1.2 g, 11.1 mmol) and 5-bromo-2-fluoro-pyridine (1.5 g, 8.52 mmol) in 1,4-dioxane (15 mL) at 0° C. was added KO$^t$Bu (1.9 g, 17.05 mmol) in small portions. The reaction mixture was slowly warmed to room temperature and stirred for 6 hours. The reaction mixture was treated with ice water (30 mL) and extracted with ethyl acetate (2×30 mL). The organic layer was washed with brine (30 mL), dried over anhydrous $Na_2SO_4$ and concentrated to afford the product (1.6 g) which was used for the next step without further purification. LCMS: 264.0 (M+H) and 266.0 (M+2+H), Rt 2.63 min Column: ZORBAX XDB C-18 (50×4.6 mm), 3.5 μm Mobile Phase: A: 0.1% HCOOH in water:ACN (95:5), B: ACN; Flow Rate: 1.5 mL/min Synthesis of A62: To a stirred solution of 5-bromo-2-(3,3-difluorocyclobutoxy)pyridine (1.6 g, 6.06 mmol) and bis(pinacolato)diboron (2.0 g, 7.88 mmol) in 1,4-dioxane (32.0 mL) was added potassium acetate (1.78 g, 18.2 mmol). Pd(dppf)Cl$_2$·DCM (0.49 g, 0.61 mmol) was added to the reaction mixture under nitrogen atmosphere and heated at 80° C. for 12 hours. The reaction mixture was cooled to room temperature, filtered through Celite and concentrated under reduced pressure. The crude compound was purified by column chromatography on silica gel with 5% ethyl acetate/PE to afford the product (1.82 g, 5.8 mmol, 96% yield) LCMS: 312.2 (M+H), Rt 2.87 min Column: ZORBAX XDB C-18 (50×4.6 mm), 3.5 μm Mobile Phase: A: 0.1% HCOOH in water:ACN (95:5), B: ACN; Flow Rate: 1.5 mL/min Synthesis of Compound 52: To a stirred solution of 6-chloro-3-(difluoromethyl)-[1,2,4]triazolo[4,3-a]pyrazine (200 mg, 0.98 mmol) and 2-(3,3-difluorocyclobutoxy)-5-(4,4,5,5-tetramethyl-1,3,2-dioxaborolan-2-yl)pyridine (365 mg, 1.17 mmol) in 1,4-dioxane (4.5 mL) was added water (0.5 mL) and Cs$_2$CO$_3$ (637 mg, 1.96 mmol). Pd(dppf)Cl$_2$·DCM (80 mg, 0.1 mmol) was added to the reaction mixture under nitrogen atmosphere and heated at 80° C. for 16 hours. The reaction mixture was cooled to room temperature, filtered through Celite and concentrated under reduced pressure. The crude compound was purified by preparative HPLC to afford a solid (153 mg, 0.43 mmol, 44% yield). Prep. HPLC method: Rt 9.2; Column: Atlantis C-18 (150×19 mm), 5.0 μm; Mobile phase: 0.1% TFA in water/acetonitrile; Flow Rate: 15.0 mL/min. HPLC: Rt 4.17 min, 99.4% Column: XBridge C8 (50×4.6) mm, 3.5 μm Mobile phase: A: 0.1% TFA in water, B: 0.1% TFA in ACN; Flow Rate: 2.0 mL/min. LCMS: 354.1 (M+H), Rt 2.10 min, 99.9% Column: ZORBAX XDB C-18 (50×4.6 mm), 3.5 μm Mobile Phase: A: 0.1% HCOOH in water:ACN (95:5), B: ACN; Flow Rate: 1.5 mL/min. $^1$H NMR (400 MHz, CD$_3$OD): δ 9.53 (d, 1H), 8.90 (d, 1H), 8.80 (d, 1H), 8.38 (dd, 1H), 7.59 (t, 1H), 6.98 (dd, 1H), 5.25-5.19 (m, 1H), 3.20-3.12 (m, 2H), 2.81-2.71 (m, 2H).

Synthesis of A60: To a stirred solution of 2,5-dichloropyrazine (20.0 g, 134.2 mmol) in ethanol (200 mL) was added hydrazine hydrate (20.16 g, 402.74 mmol) and heated to 80° C. for 12 hours. The reaction mixture was cooled to room temperature and treated with ice water. The precipitated solid was filtered, washed with water and dried to give the product (16.0 g) as a solid which was used for the next step without further purification.

Synthesis of A4: To a stirred solution of 2-chloro-5-hydrazineylpyrazine (3.0 g, 20.75 mmol) in toluene (30 mL) was added difluoroacetic anhydride (2.85 mL, 22.83 mmol)

Example 53: Synthesis of A49

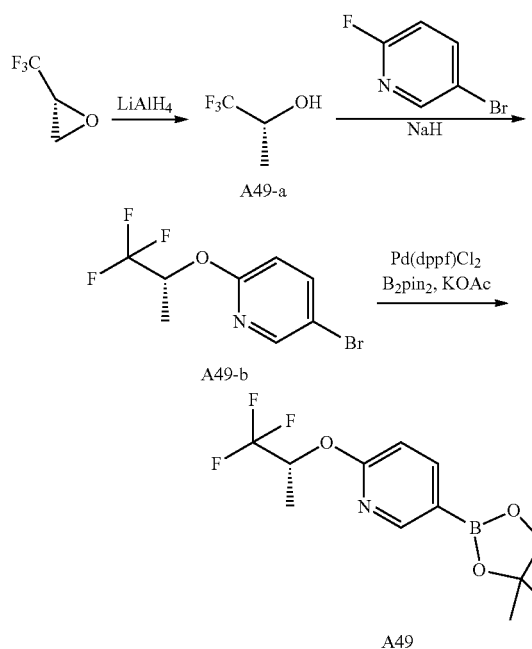

Synthesis of A49-a: To a solution of (R)-2-(trifluoromethyl)oxirane (2.2 g, 19.63 mmol) in THF (20.0 mL) was added LiAlH$_4$ (2.0 M in THF, 4.91 mL, 9.82 mmol) dropwise at 0° C. The reaction mixture was slowly warmed to room temperature and stirred for 3 hours. The reaction mixture was cooled to 0° C. and treated with sat Na$_2$SO$_4$ solution (2.0 mL). The reaction mixture was filtered through Celite, the filtrate was dried over Na$_2$SO$_4$ and used for the next step as a solution in THF.

Synthesis of A49-b: To a solution of A49-a (30.68 mmol) in THF was added NaH (1.84 g, 46 mmol) portion wise at 0° C. and stirred for 30 min. 5-bromo-2-fluoro-pyridine (4.32 g, 24.55 mmol) was added to the reaction mixture slowly at 0° C. The reaction mixture was slowly warmed to room temperature and stirred for 3 hours. The reaction mixture was cooled to 10° C., treated with ice water (10 mL) and extracted with ethyl acetate (2×50 mL). The organic layer was washed with brine (40 mL), dried over Na$_2$SO$_4$ and concentrated. The crude product was purified by column chromatography on silica gel with 20% EtOAc/PE to afford the product (3.1 g, 11.5 mmol, 37% yield) as a colourless liquid. LCMS: 270.0 (M+H) and 272.0 (M+2+H), Rt 2.78 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A49: To a stirred solution of A49-b (3.1 g, 11.5 mmol) and bis(pinacolato)diboron (3.79 g, 14.92 mmol) in 1,4-dioxane (35.0 mL) was added potassium acetate (2.25 g, 22.96 mmol). Pd(dppf)Cl$_2$-DCM (1.41 g, 1.72 mmol) was added to the reaction mixture under nitrogen atmosphere and heated at 90° C. for 12 hours. The reaction mixture was cooled to room temperature, filtered through Celite and concentrated under reduced pressure. The crude compound was purified by column chromatography on silica gel with 6% ethyl acetate/PE to afford the product (2.8 g, 8.83 mmol, 76% yield) as a solid. LCMS: 318.0 (M+H), Rt 4.04 min Column: ZORBAX Extend (50×4.6 mm), 5 μm Mobile Phase: A: 10 mM Ammonium acetate in water, B: ACN; Flow Rate: 1.2 mL/min.

Example 54: Synthesis of A50

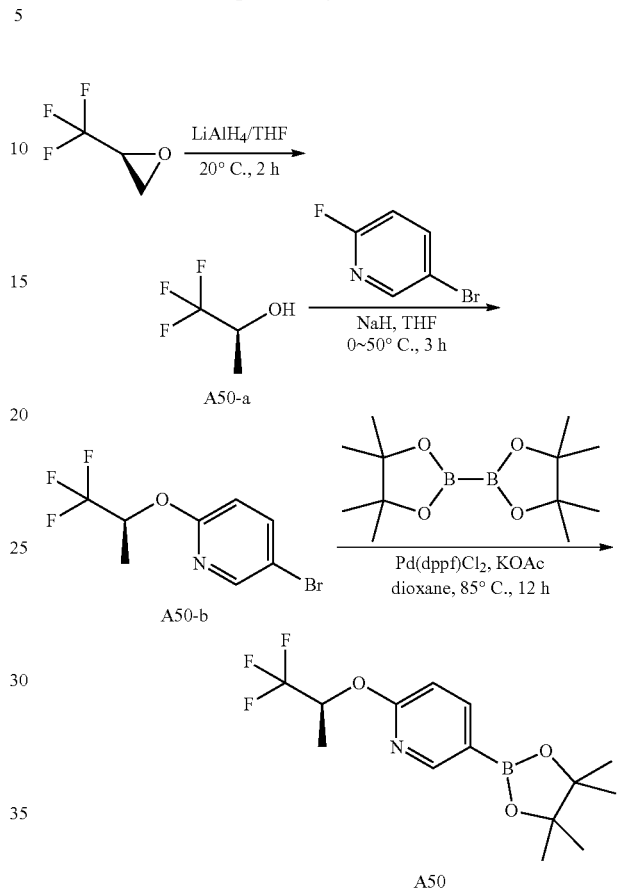

Synthesis of A50-a: To a mixture of (2S)-2-(trifluoromethyl)oxirane (3 g, 26.77 mmol) in THF (25 mL) was added LiAlH$_4$ (0.5 g, 13.2 mmol) at 0° C. under N$_2$ over 30 minutes, then the mixture was stirred at 20° C. for 2 hours. After cooling to 0° C., the mixture was quenched with water (0.9 g), the mixture was stirred at 35° C. for 30 minutes. The mixture was filtered through Celite, eluted with THF (20 mL×2), the organic phase was washed with brine (20 mL×2) and dried over Na$_2$SO$_4$, filtered to give the crude product (3 g, 26.3 mmol, 98% yield) as a solution in THF, which was used directly without any further purification.

Synthesis of A50-b: To a solution of (2S)-1,1,1-trifluoropropan-2-ol in THF (50 mL) was added NaH (0.8 g, 19.94 mmol) at 0° C. over 20 minutes, and the mixture was stirred at 0° C. for 40 minutes. Then to the mixture was added 5-bromo-2-fluoro-pyridine (2.7 g, 15.34 mmol), and the mixture was stirred at 50° C. for 2 hours. The mixture was quenched with sat. NH$_4$Cl (40 mL), extracted with EtOAc (60 mL), the combined organic phase was washed with brine (40 mL×2), dried over Na$_2$SO$_4$, filtered and concentrated to give the crude product (3.48 g, 9.29 mmol, 61% yield) as an oil. LCMS R$_t$=0.95 min in 1.5 min chromatography, 5-95AB, MS ESI calcd. for C$_8$H$_8$BrF$_3$NO [M+H]$^+$ 270.0, found 269.9.

Synthesis of A50: A mixture of 5-bromo-2-[(1S)-2,2,2-trifluoro-1-methyl-ethoxy]pyridine (3.48 g, 12.89 mmol), 4,4,5,5-tetramethyl-2-(4,4,5,5-tetramethyl-1,3,2-dioxaborolan-2-yl)-1,3,2-dioxaborolane (4.91 g, 19.33 mmol), KOAc (2.53 g, 25.77 mmol) and Pd(dppf)Cl$_2$ (1.13 g, 1.55 mmol) in 1,4-Dioxane (35 mL) was stirred at 85° C. for 12 hours under N$_2$. After cooling to room temperature, the mixture was concentrated to give a residue. The residue was diluted with H$_2$O (30 mL), and the mixture was extracted with EtOAc (40 mL×2). The combined organic phase was washed with water (40 mL) and brine (40 mL), dried over Na$_2$SO$_4$, filtered and concentrated to give the crude product. The crude product was purified by flash chromatography on silica gel (EtOAc in PE=0% to 1%) to give the product (3 g, 5.72 mmol, 44% yield) as an oil. 1H NMR (DMSO-d$_6$, 400 MHz) δ$_H$=8.42 (d, 1H), 7.96 (dd, 1H), 6.93 (d, 1H), 6.00-5.93 (m, 1H), 1.45 (d, 3H), 1.30 (s, 12H). LCMS R$_t$=1.02 min in 1.5 min chromatography, 5-95AB, MS ESI calcd. for C$_{14}$H$_{20}$BF$_3$NO$_3$ [M+H]$^+$ 318.1, found 318.1.

Example 55: Synthesis of A51

Synthesis of A51: A mixture of 5-chloro-2-[5-fluoro-6-[(1S)-2,2,2-trifluoro-1-methyl-ethoxy]-3-pyridyl]-3-methyl-pyrazine (1.1 g, 3.28 mmol) and hydrazine (1.05 g, 32.83 mmol) in MeCN (20 mL) was heated to 90° C. and stirred for 16 hours. After cooling to room temperature, the reaction mixture was concentrated. The mixture was diluted with H$_2$O (20 mL), extracted with EtOAc (20 mL×2). The combined organic phase was washed with brine (20 mL), dried over Na$_2$SO$_4$, filtered and concentrated to give the crude product. The crude product was triturated from PE (5 mL) to give the product (800 mg, 2.41 mmol, 68% yield) as a solid. The crude product was used into the next step without further purification. LCMS R$_t$=0.75 min in 1.5 min chromatography, 5-95AB, MS ESI calcd. for C$_{13}$H$_{14}$F$_4$N$_5$O [M+H]$^+$ 332.1, found 332.1.

Example 56: Synthesis of A54

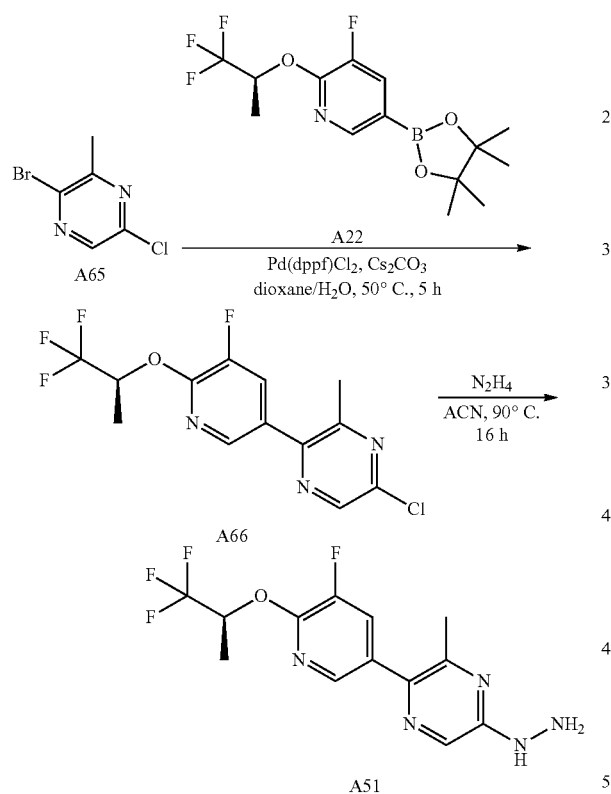

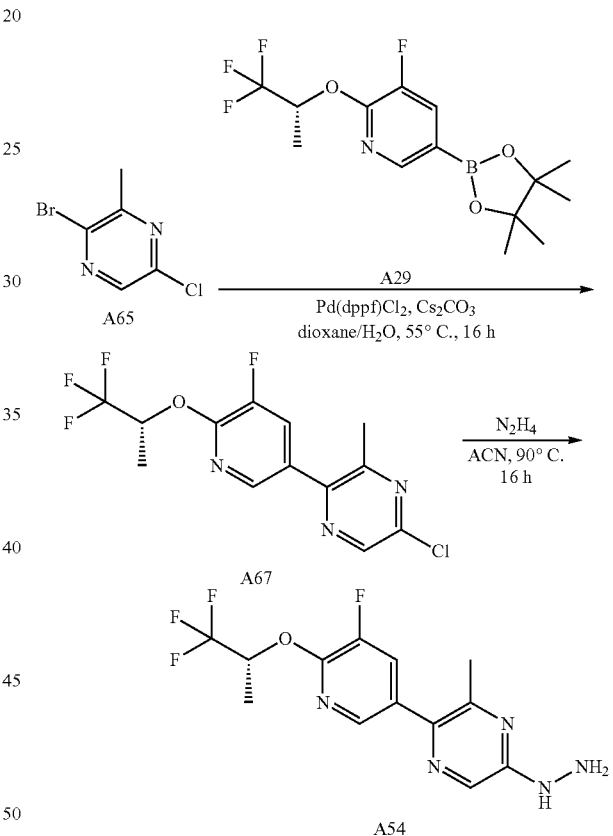

Synthesis of A66: A mixture of 2-bromo-5-chloro-3-methyl-pyrazine (900 mg, 4.34 mmol), 3-fluoro-5-(4,4,5,5-tetramethyl-1,3,2-dioxaborolan-2-yl)-2-[(1S)-2,2,2-trifluoro-1-methyl-ethoxy]pyridine (1.31 g, 3.9 mmol), Pd(dppf)Cl$_2$ (0.48 g, 0.65 mmol) and Cs$_2$CO$_3$ (2.83 g, 8.68 mmol) in 1,4-Dioxane (40 mL) and Water (8 mL) was stirred under N$_2$ at 50° C. for 5 hours. The mixture was cooled to room temperature, diluted with EtOAc (30 mL), filtered through silica gel and eluted with EtOAc (20 mL), and the filtrate was concentrated to give the crude product. The product was purified by flash chromatography on silica gel (EtOAc in PE=0% to 3%) to give the product (1100 mg, 2.83 mmol, 65% yield) as a solid. LCMS R$_t$=1.41 min in 1.5 min chromatography, 10-80AB, MS ESI calcd. for C$_{13}$H$_{11}$ClF$_4$N$_3$O [M+H]$^+$ 336.0, found 336.0.

Synthesis of A67: A mixture of 2-bromo-5-chloro-3-methyl-pyrazine (900 mg, 4.34 mmol), 3-fluoro-5-(4,4,5,5-tetramethyl-1,3,2-dioxaborolan-2-yl)-2-[(1R)-2,2,2-trifluoro-1-methyl-ethoxy]pyridine (1.31 g, 3.9 mmol), Pd(dppf)Cl$_2$ (0.48 g, 0.65 mmol) and Cs$_2$CO$_3$ (2.83 g, 8.68 mmol) in 1,4-Dioxane (40 mL) and water (8 mL) was stirred under N$_2$ at 55° C. for 16 hours. The mixture was cooled to room temperature, diluted with EtOAc (50 mL), filtered with silica gel, eluted with EtOAc (20 mL) and concentrated to give the crude product. The product was purified by flash chromatography on silica gel (EtOAc in PE=0% to 20%) yielding the product (930 mg, 2.62 mmol, 60% yield) as a colorless oil. LCMS R$_t$=0.95 min in 1.5 min chromatography, 5-95AB, MS ESI calcd. for C$_{13}$H$_{11}$ClF$_4$N$_3$O [M+H]$^+$ 336.0, found 336.1.

Synthesis of A54: A mixture of hydrazine (1775.89 mg, 55.41 mmol) and 5-chloro-2-[5-fluoro-6-[(1R)-2,2,2-trifluoro-1-methyl-ethoxy]-3-pyridyl]-3-methyl-pyrazine (930 mg, 2.77 mmol) in CH$_3$CN (10 mL) was stirred at 90° C. for 16 hours. After cooling to room temperature, the reaction was quenched with sat. NH$_4$Cl (30 mL), and the mixture was extracted with EtOAc (40 mL×2). The combined organic phase was washed with water (30 mL) and brine (30 mL), dried over Na$_2$SO$_4$, filtered and concentrated to give the crude product (980 mg, 2.45 mmol, 89% yield) as a solid. LCMS R$_t$=0.75 min in 1.5 min chromatography, 5-95AB, MS ESI calcd. for C$_{13}$H$_{14}$F$_4$N$_5$O [M+H]$^+$ 332.1, found 332.2.

Example 57: Synthesis of A30

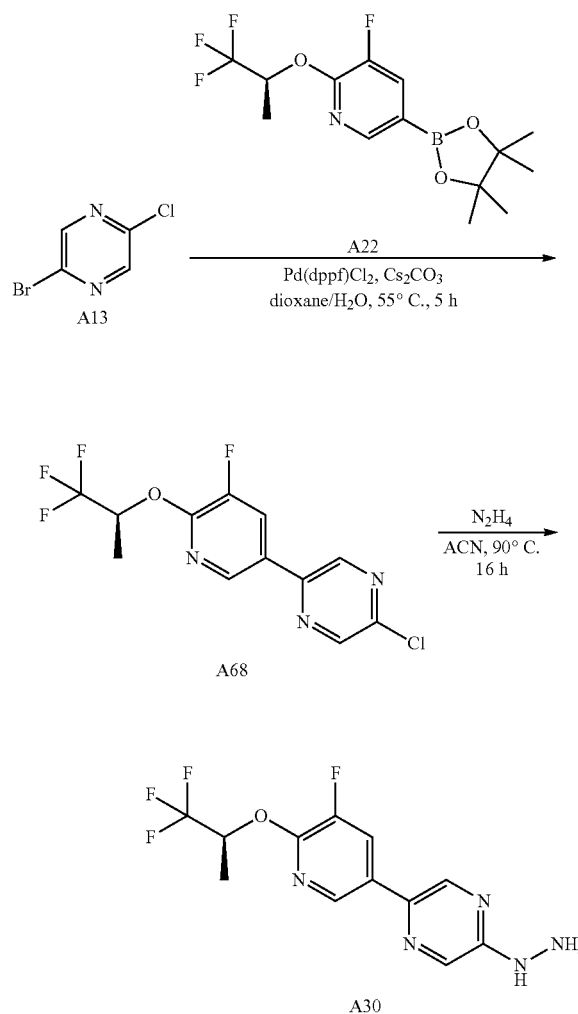

Synthesis of A68: A mixture of 2-bromo-5-chloro-pyrazine (1 g, 5.17 mmol), 3-fluoro-5-(4,4,5,5-tetramethyl-1,3,2-dioxaborolan-2-yl)-2-[(1S)-2,2,2-trifluoro-1-methyl-ethoxy]pyridine (1.73 g, 5.17 mmol), Cs$_2$CO$_3$ (3.37 g, 10.34 mmol) and Pd(dppf)Cl$_2$ (567.41 mg, 0.78 mmol) in 1,4-Dioxane (100 mL) and Water (10 mL) was stirred at 55° C. under N$_2$ for 5 hours. From LCMS, desired MS was observed and no starting material was remained. The solution was cooled to room temperature and concentrated to give a residue. To the residue was added water (50 mL), extracted with EtOAc (50 mL×2). The combined organic phase was washed with water (50 mL), brine (50 mL×2), dried over anhydrous Na$_2$SO$_4$, filtered and concentrated to give the crude product. The crude product was purified by flash chromatography column on silica gel (EtOAc in PE=0% to 5%) to give the product (1.4 g, 4.35 mmol, 84% yield) as a solid. $^1$H NMR (DMSO-d$_6$, 400 MHz) δ$_H$=9.18 (s, 1H), 8.91-8.74 (m, 2H), 8.46 (dd, 1H), 6.05-5.99 (m, 1H), 1.53 (d, 3H).

Synthesis of A30: A solution of 2-chloro-5-[5-fluoro-6-[(1S)-2,2,2-trifluoro-1-methyl-ethoxy]-3-pyridyl]pyrazine (1.4 g, 4.35 mmol) and hydrazine (697.48 mg, 21.76 mmol) in MeCN (100 mL) was stirred at 90° C. for 16 hours to give a colorless solution. After cooling to room temperature, the solution was concentrated to give a residue. To the residue was added water (50 mL), extracted with EtOAc (50 mL×2). The combined organic phase was washed with brine (50 mL), dried over anhydrous Na$_2$SO$_4$, filtered and concentrated to give the crude product (1.3 g, 4.10 mmol) as a solid. LCMS R$_t$=0.72 min in 1.5 min chromatography, 5-95AB, MS ESI calcd. for C$_{12}$H$_{12}$F$_4$N$_5$O [M+H]$^+$ 318.1, found 318.1.

Details for the synthesis of certain intermediates and starting materials may be found in PCT/US2017/063533 and PCT/US2018/000224, the contents of which are incorporated herein by reference.

Example 58: Biological Activity

Functional characterization of exemplary compounds to modulate voltage gated sodium currents was accomplished using the PatchXpress™ high throughput electrophysiology platforms (Molecular Devices, Sunnyvale, CA). HEK-293 cells expressing recombinant sodium channels were grown in DMEM/high-glucose Dulbecco's modified, 10% FBS, 2 mM sodium pyruvate, and G418. Nav channel expressing cells were grown to 50%-80% confluency and harvested by trypsinization. Trypsinized cells were washed and resuspended in extracellular buffer at a concentration of 1×106 cells/ml. The onboard liquid handling facility of the PatchXpress was used for dispensing cells and application of test compounds. Nav late currents were evoked by the application of ATX-II, 300 nM. Currents were evoked by depolarizing pulses to 0 mV for 200 ms from a non-inactivating holding potential (e.g., −120 mV to −150 mV) at a frequency of 0.1 Hz. Late current amplitude and stability were determined by analyzing the mean current amplitude over the 175-195 msec region of the 200 msec test pulse. Following steady state block with exemplary compounds (e.g., as described herein) at 1 μM, a Na$^+$ free solution containing an impermeant cation (e.g., Choline or NDMG) was added for determination of the 0 current level. Late current amplitudes for each test condition were determined from the mean of the 175-195 msec region of the 200 msec test pulse. Percent inhibition of steady state currents was calculated as (compound−baseline)/(control−baseline)*100, where control represents INaL recorded in the absence of compound. Results from this assay are summarized in Table 1 below. In this table, "A" indicates inhibition of less than 50% and "B" indicates inhibition of 50% to 75%; and "C" indicates inhibition of greater than 75%.

TABLE 1

| Compound | INaL v1.6 % Inhibition |
|---|---|
| 1 | C |
| 2 | A |
| 3 | C |
| 4 | B |
| 5 | C |
| 6 | C |
| 7 | C |
| 8 | B |
| 9 | C |
| 10 | B |

TABLE 1-continued

| Compound | INaL v1.6 % Inhibition |
|---|---|
| 11 (Isomer 1) | C |
| 11 (Isomer 2) | C |
| 12 | C |
| 13 (Isomer 1) | A |
| 13 (Isomer 2) | B |
| 14 | C |
| 15 | C |
| 16 (Isomer 1) | A |
| 16 (Isomer 2) | B |
| 17 | C |

TABLE 1-continued
| Compound | INaL v1.6 % Inhibition |
|---|---|
| 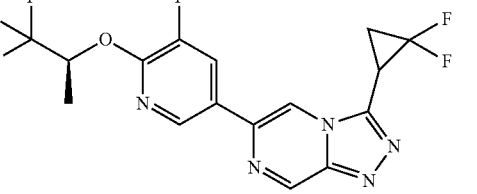 18 (Isomer 1) | A |
| 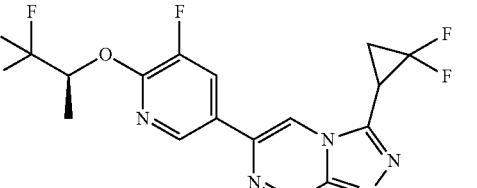 18 (Isomer 2) | B |
| 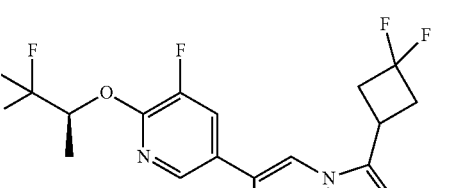 19 | B |
| 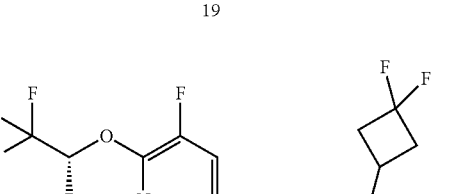 20 | A |
| 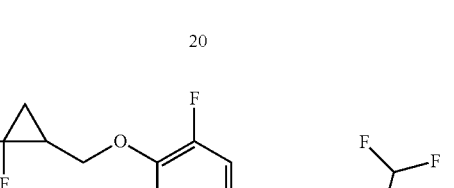 21 (Isomer 1) | B |
| 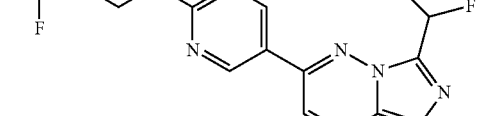 21 (Isomer 2) | A |
| 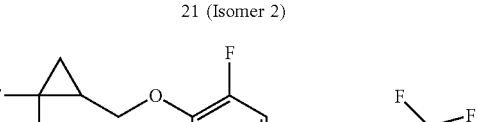 22 | A |
|  23 (Isomer 1) | B |
| 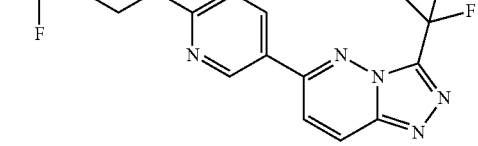 23 (Isomer 2) | B |
| 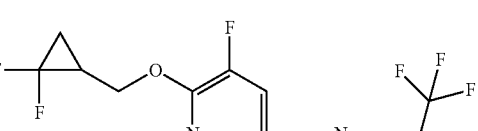 24 | B |
| 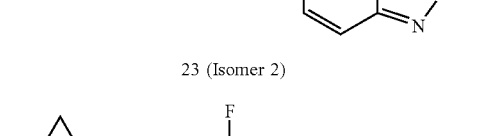 25 (Isomer 1) | C |

TABLE 1-continued
| Compound | INaL v1.6 % Inhibition |
|---|---|
| 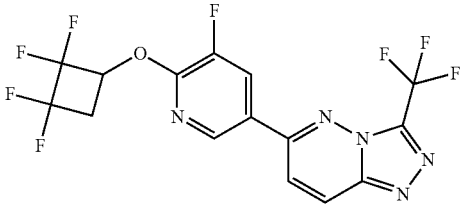 [SMILES: Fc1cc(-c2ccc3nnc(C(F)(F)F)n3n2)cnc1OC1CC(F)(F)C1(F)F]<br>25 (Isomer 2) | C |
| 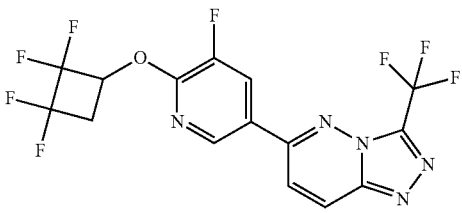 [SMILES: Fc1cc(-c2ccc3nnc(C(F)(F)F)n3n2)cnc1OC1CC(F)(F)C1(F)F]<br>26 | C |
| 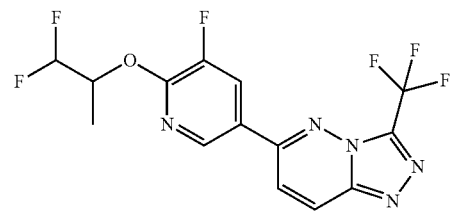 [SMILES: CC(Oc1ncc(-c2ccc3nnc(C(F)(F)F)n3n2)cc1F)C(F)F]<br>27 (Isomer 1) | B |
| 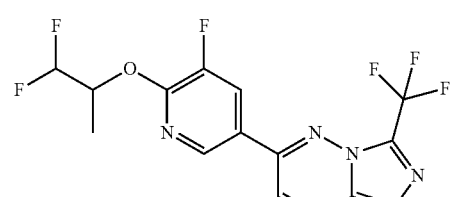<br>27 (Isomer 2) | B |
| 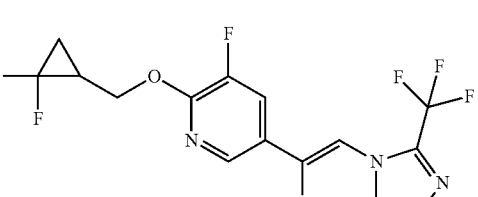<br>28 (Isomer 1) | B |
| 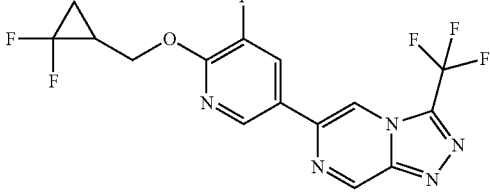<br>28 (Isomer 2) | B |
| 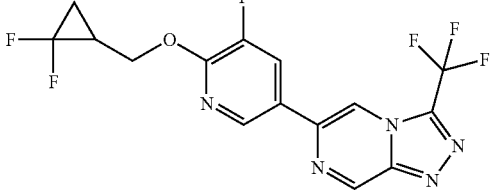<br>29 | B |
| 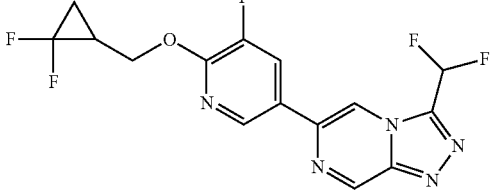<br>30 (Isomer 1) | A |
| 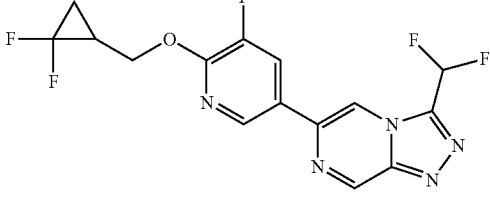<br>30 (Isomer 2) | A |
| 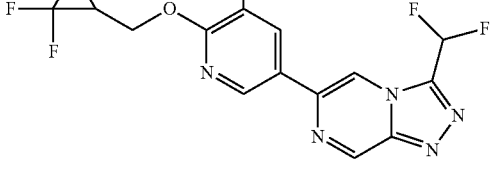<br>31 | A |
| 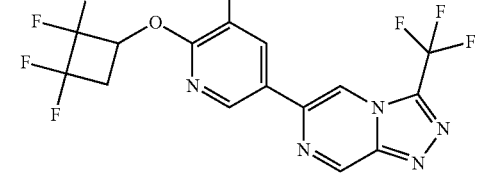<br>32 (Isomer 1) | C |

TABLE 1-continued

| Compound | INaL v1.6 % Inhibition |
|---|---|
| 32 (Isomer 2) | C |
| 33 | C |
| 34 | C |
| 35 | C |
| 36 | C |
| 37 | C |
| 38 | B |
| 39 | B |
| 40 | C |
| 41 | C |

TABLE 1-continued

| Compound | INaL v1.6 % Inhibition |
|---|---|
| 42 | B |
| 43 | B |
| 44 | C |
| 45 | B |
| 46 | C |
| 47 | B |
| 48 | C |
| 49 | B |
| 50 | C |
| 51 | B |
| 52 | B |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:
1. A method for modulating a voltage gated sodium ion channel current in a subject, wherein the method comprises administering to the subject in need thereof a therapeutically effective amount of a compound having Formula (I):

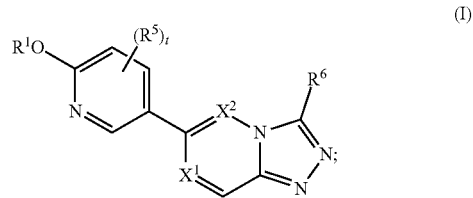

or a pharmaceutically acceptable salt or stereoisomer thereof,
wherein:
(i) $X^1$ is N; and
  $X^2$ is $CR^d$; or
(ii) $X^1$ is $CR^d$; and
  $X^2$ is N;
  $R^1$ is $CR^2R^3R^4$, monocyclic $C_{3-6}$ cycloalkyl, or monocyclic 4- to 7-membered heterocyclyl, wherein the $C_{3-6}$ cycloalkyl or 4- to 7-membered heterocyclyl is optionally substituted with one or more independently selected $R^a$ substituents;
  $R^2$ is $C_{1-4}$ haloalkyl or monocyclic $C_{3-6}$ cycloalkyl, wherein the $C_{3-6}$ cycloalkyl is optionally substituted with one or more independently selected $R^b$ substituents;
  $R^3$ is hydrogen, $C_{1-4}$ alkyl, or $C_{1-4}$ haloalkyl;
  $R^4$ is hydrogen, $C_{1-4}$ alkyl, or $C_{1-4}$ haloalkyl;
  $R^5$ is halo;
  $R^6$ is $C_{1-4}$ haloalkyl or monocyclic $C_{3-6}$ cycloalkyl, wherein the $C_{3-6}$ cycloalkyl is optionally substituted with one or more independently selected Re substituents;
  each $R^a$ is independently halo, $C_{1-4}$ alkyl, $C_{1-4}$ haloalkyl, $OC_{1-4}$ alkyl, or $OC_{1-4}$ haloalkyl;
  each $R^b$ is independently halo, $C_{1-4}$ alkyl, $C_{1-4}$ haloalkyl, $OC_{1-4}$ alkyl, or $OC_{1-4}$ haloalkyl;
  each $R^c$ is independently halo, $C_{1-4}$ alkyl, $C_{1-4}$ haloalkyl, $OC_{1-4}$ alkyl, or $OC_{1-4}$ haloalkyl;
  $R^d$ is hydrogen, halo, or $C_{1-4}$ alkyl; and
  t is 0, 1, or 2;
with the provisos that:
(1) when $R^3$ and $R^4$ are each independently hydrogen, then $R^6$ is not $CF_2Cl$, cyclopropyl, fluorocyclopropyl, difluorocyclopropyl, or difluorocyclobutyl;
(2) when $R^6$ is $CHF_2$ or $CF_3$, then $R^1$ is not difluorocyclobutyl;
(3) when $R^6$ is $CHF_2$ or $CF_3$ and $R^3$ and $R^4$ are each independently hydrogen, then $R^2$ is not $CF_3$;
(4) when $R^6$ is $CHF_2$ or $CF_3$, one of $R^3$ or $R^4$ is hydrogen, $X^1$ is N, and $X^2$ is CH, then $R^2$ is not $CF_3$; and
(5) when $R^6$ is $CF_3$, one of $R^3$ or $R^4$ is hydrogen, $X^1$ is CH, and $X^2$ is N, then $R^2$ is not $CF_3$.

2. The method of claim 1, wherein the subject has a condition selected from the group consisting of autosomal dominant nocturnal frontal lobe epilepsy, a benign familial neonatal-infantile seizure, cryptogenic pediatric partial epilepsy with an SCN3A mutation, focal epilepsy with an SCN3A mutation, generalized epilepsy with a febrile seizure, an infantile spasm, intractable childhood epilepsy with a generalized tonic-clonic seizure, a malignant migrating partial seizure of infancy, Dravet syndrome, sudden unexpected death in epilepsy (SUDEP), epileptic encephalopathy with an SCN1A mutation, epileptic encephalopathy with an SCN2A mutation, epileptic encephalopathy with an SCN8A mutation, early infantile epileptic encephalopathy, KCNQ2 epileptic encephalopathy, KCNT1 epileptic encephalopathy, and Rasmussen's encephalitis.

3. The method of claim 2, wherein the Dravet syndrome is Dravet syndrome with an SCN1A mutation.

4. The method of claim 1, wherein the subject has a condition selected from the group consisting of epilepsy, an epilepsy syndrome, epileptic encephalopathy, pain, and Rasmussen's encephalitis.

5. The method of claim 4, wherein the subject has pain.

6. The method of claim 5, wherein the pain is selected from the group consisting of cerebellar ataxia, a cluster headache, a migraine, neuropathic pain, and trigeminal neuralgia.

7. The method of claim 6, wherein the pain is a migraine.

8. The method of claim 7, wherein the migraine is a hemiplegic migraine.

9. The method of claim 8, wherein the hemiplegic migraine is a familial hemiplegic migraine.

10. The method of claim 9, wherein the familial hemiplegic migraine is familial hemiplegic migraine type 3.

11. The method of claim 1, wherein the compound is:

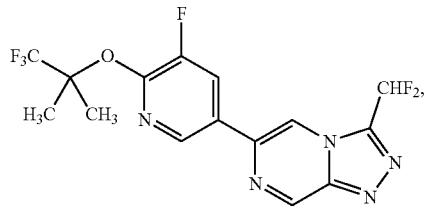 [SMILES: CC(C)(Oc1ncc(-c2cn3c(C(F)F)nnc3cn2)cc1F)C(F)(F)F]

or a pharmaceutically acceptable salt thereof.

12. The method of claim 1, wherein the compound is selected from the group consisting of:

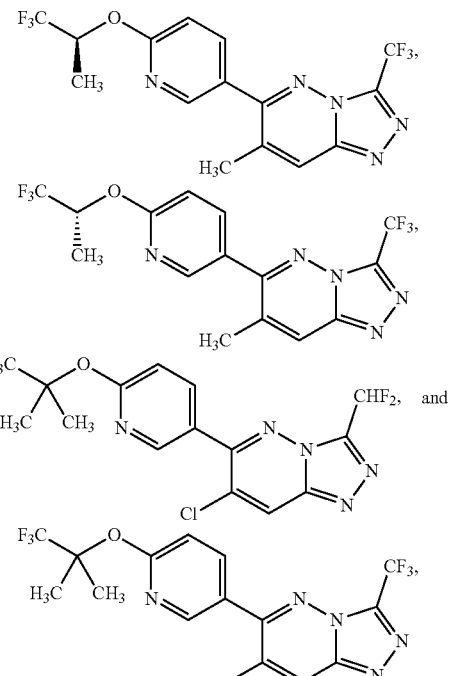

or a pharmaceutically acceptable salt thereof.

* * * * *

UNITED STATES PATENT AND TRADEMARK OFFICE
CERTIFICATE OF CORRECTION

PATENT NO. : 12,344,615 B2
APPLICATION NO. : 17/968465
DATED : July 1, 2025
INVENTOR(S) : Andrew Mark Griffin et al.

Page 1 of 1

It is certified that error appears in the above-identified patent and that said Letters Patent is hereby corrected as shown below:

In the Claims

In Column 118, Claim 1, Lines 5-15, please replace " 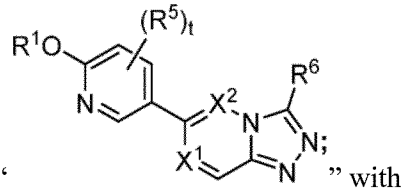 " with 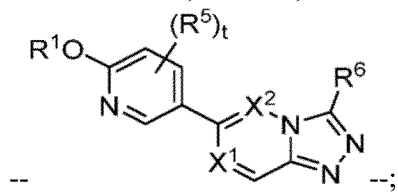 --;

In Column 118, Claim 1, Lines 37-38, please replace "with one or more independently selected Re substituents" with -- with one or more independently selected $R^c$ substituents --; and In Column 120, Claim 12, Lines 17-24, please replace " 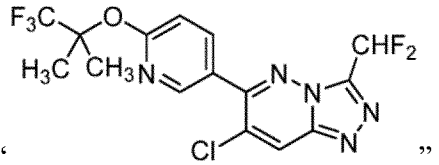 " with 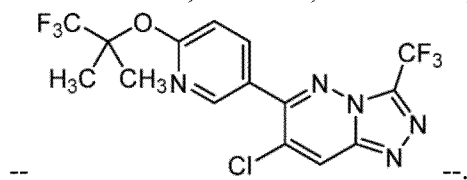 --.

Signed and Sealed this
Twenty-sixth Day of August, 2025

Coke Morgan Stewart
*Acting Director of the United States Patent and Trademark Office*